US011975111B2

(12) United States Patent
Shailubhai

(10) Patent No.: US 11,975,111 B2
(45) **Date of Patent: *May 7, 2024**

(54) DACTINOMYCIN COMPOSITIONS AND METHODS FOR THE TREATMENT OF MYELODYSPLASTIC SYNDROME AND ACUTE MYELOID LEUKEMIA

(71) Applicant: Tiziana Life Sciences PLC, London (GB)

(72) Inventor: Kunwar Shailubhai, Line Lexington, PA (US)

(73) Assignee: Tiziana Life Sciences PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/193,058

(22) Filed: Mar. 5, 2021

(65) Prior Publication Data

US 2021/0275463 A1 Sep. 9, 2021

Related U.S. Application Data

(62) Division of application No. 15/703,953, filed on Sep. 13, 2017, now Pat. No. 10,973,773.

(Continued)

(51) Int. Cl.

*A61K 9/51* (2006.01)
*A61K 9/00* (2006.01)

(Continued)

(52) U.S. Cl.

CPC .......... *A61K 9/5153* (2013.01); *A61K 9/0019* (2013.01); *A61K 31/7068* (2013.01);

(Continued)

(58) Field of Classification Search

CPC ...... A61K 47/24; A61K 45/06; A61K 9/0019; A61K 31/7068; A61K 38/12;

(Continued)

(56) References Cited

U.S. PATENT DOCUMENTS 4,994,281 A 2/1991 Muranishi et al.
6,322,805 B1 11/2001 Kim et al.

(Continued)

FOREIGN PATENT DOCUMENTS

CN 1887264 A 1/2007
EP 2 397 149 A1 12/2011

(Continued)

OTHER PUBLICATIONS

Czader et al., “Therapy-Related Myeloid Neoplasms”, Am J Clin Pathol, 2009 (132), 410-415. (Year: 2009).*

(Continued)

*Primary Examiner* — Jianfeng Song
(74) *Attorney, Agent, or Firm* — COOLEY LLP

(57) ABSTRACT

The disclosure provides compositions comprising dactinomycin, formulated for delivery by nanoparticle, and methods for treating a myelodysplastic syndrome (MDS) or cancer, for example, NPM1-mutated acute myeloid leukemia (AML), by administration of the compositions of the disclosure.

5 Claims, 39 Drawing Sheets

Related U.S. Application Data

(60) Provisional application No. 62/394,104, filed on Sep. 13, 2016, provisional application No. 62/444,330, filed on Jan. 9, 2017, provisional application No. 62/500,459, filed on May 2, 2017.

(51) Int. Cl.

| | |
|---|---|
| ***A61K 31/7068*** | (2006.01) |
| ***A61K 38/12*** | (2006.01) |
| ***A61K 45/06*** | (2006.01) |
| ***A61K 47/24*** | (2006.01) |

(52) U.S. Cl.

CPC .............. *A61K 38/12* (2013.01); *A61K 45/06* (2013.01); *A61K 47/24* (2013.01)

(58) Field of Classification Search

CPC ... A61K 9/5153; A61K 2300/00; A61P 43/00; A61P 35/00; A61P 35/02

See application file for complete search history.

(56) References Cited

U.S. PATENT DOCUMENTS

| | | | | |
|---|---|---|---|---|
| 6,685,917 | B2 | 2/2004 | Rosenthal et al. | |
| 7,713,440 | B2 | 5/2010 | Anderson | |
| 8,221,779 | B2 | 7/2012 | Jonas et al. | |
| 10,973,773 | B2 | 4/2021 | Shailubhai | |
| 2002/0156047 | A1 | 10/2002 | Zhao | |
| 2004/0023925 | A1 | 2/2004 | Chang et al. | |
| 2006/0111358 | A1 | 5/2006 | De Bont et al. | |
| 2010/0068285 | A1* | 3/2010 | Zale | A61K 9/107 977/773 |
| 2010/0286075 | A1 | 11/2010 | Lee et al. | |
| 2011/0262525 | A1* | 10/2011 | Wang | A61P 35/02 424/85.7 |
| 2011/0318420 | A1 | 12/2011 | Hu et al. | |
| 2014/0271489 | A1 | 9/2014 | Grinstaff et al. | |
| 2014/0294986 | A1 | 10/2014 | Liu et al. | |
| 2015/0064238 | A1 | 3/2015 | Lin et al. | |
| 2016/0206563 | A1 | 7/2016 | Jain | |

FOREIGN PATENT DOCUMENTS

| | | | |
|---|---|---|---|
| JP | H02193984 | A | 7/1990 |
| WO | WO 2006/089290 | A1 | 8/2006 |
| WO | WO 2009/070302 | A1 | 6/2009 |
| WO | WO 2009/073193 | A2 | 6/2009 |
| WO | WO 2011/157802 | A1 | 12/2011 |
| WO | WO 2013/012891 | A1 | 1/2013 |
| WO | WO 2015/101618 | A1 | 7/2015 |
| WO | WO 2017/016108 | A1 | 2/2017 |

OTHER PUBLICATIONS

Jahan et al., "Investigation and optimization of formulation parameters on preparation of target anti-CD205 tailored PLGA nanoparticle", International Journal of Nanomedicine, 2015 (10), 7371-7384. (Year: 2015).*

Olberding et al., "Actinomycin D synergistically enhances the efficacy of the BH3 mimetic ABT-37 by downregulating Mcl-1 expression", Cancer Biology & Therapy 10:9, 918-929; Nov. 1, 2010. (Year: 2010).*

Veal et al., "Pharmacokinetics of Dactinomycin in a pediatric Patient Population", Clin Cancer Res 2005;5893 11(16), 5893-5899, Aug. 15, 2005. (Year: 2005).*

Anderson, D. et al. "Drug Delivery: LyoCell® Technology—A Lipidic Drug Delivery System Based on Reverse Cubic and Hexagonal Phase Lyotropic Liquid Crystalline Nanoparticles", CRC Concise Encyclopedia of Nanotechnology, 2016, 5 pages.

Ashton S. et al. "Aurora kinase inhibitor nanoparticles target tumors with favorable therapeutic index in vivo", Science Translational Medicine, 2016, vol. 8, Issue 325, 12 pages.

Avgoustakis, K. et al. "Effect of copolymer composition on the characteristics, in vitro stability, and biodistribution of PLEA-mPEG nanoparticles", International Journal of Pharmaceutics, 2003, vol. 259, No. 1, pp. 115-126.

Avgoustakis, K. "Pegylated poly(lactide) and poly(lactide-co-glycolide) nanoparticles: Preparation, properties and possible applications in drug delivery", Current Drug Delivery, vol. 1, No. 4, 2004, pp. 321-333.

Bears, D. "Are Accurins the cure for Aurora kinase inhibitors?", Science Translational Medicine, 2016, vol. 8, Issue 325, 3 pages.

Brasseur F. et al. "Actinomycin D Adsorbed Polymethylcyanoacrylate Increased Efficiency Against an Experimental Tumor", European Journal of Cancer, 1980, vol. 16, p. 1441-1445.

Bundegaard, H., "Design of prodrugs: Bioreversible derivatives for various functional groups and chemical entities", Design of Prodrugs, 1985, p. 1-92.

Burger K. et al. "Chemotherapeutic Drugs Inhibit Ribosome Biogenesis at Various Levels", Journal of Biological Chemistry, 2010, vol. 285, p. 12416-12425.

Cancer Genome Atlas Research Network, "Genomic and epigenomic landscapes of adult de novo acute myeloid leukemia", New England Journal of Medicine, 2013, vol. 368, p. 2059-2074.

Capurso N. et al. "Development of a nanoparticulate formulation of retinoic acid that suppresses Th17 cells and upregulates regulatory T cells", Landes Bioscience, 2010, vol. 1, Issue 4, p. 335-340.

Chen, L et al. "Combining p53 stabilizers with metformin induces synergistic apoptosis through regulation of energy metabolism in castration-resistant prostate cancer", Cell Cycle 2016, vol. 15, No. 6, p. 840-849.

Cosmegen® for Injection, 2015, 6 pages.

Dlamini, Z. et al. "Abstract 1265: RbBP6 Isoform 3 (DWNN) is a p53 stabilizer in arsenic trioxide-induced apoptosis in human cancer cell lines", Proceedings: AACR 101st Annual Meeting, 2010, 2 pages.

Dohner, H. et al. "Acute Myeloid Leukemia", New England Journal of Medicine, 2015, vol. 373, p. 1136-1152.

Even, C. et al. "Actinomycin D, cisplatin, and etoposide regimen is associated with almost universal cure in patients with high-risk gestational trophoblastic neoplasia", European Journal of Cancer, 2014, vol. 50, p. 2082-2089.

Falini B. et al. "Dactinomycin in NPM1-Mutated Acute Myeloid Leukemia", New England Journal of Medicine, vol. 373, No. 12, 2015, pp. 1180-1182.

Falini B. et al. "Acute myeloid leukemia with mutated nucleophosmin (NPM1): any hope for a targeted therapy?" Blood Reviews, 2011, vol. 25, p. 247-254.

Falini B. et al. "Cytoplasmic nucleo-phosmin in acute myelogenous leukemia with a normal karyo-type" New England Journal of Medicine, 2005, vol. 352, p. 254-266.

Fathi A. T. et al. "The role of FLT3 inhibitors in the treatment of FLT3-mutated acute myeloid leukemia", Eur. J. Haematol. 2017, vol. 98, p. 330-336.

Figueroa, M. E. et al. "MDS and secondary AML display unique patterns and abundance of aberrant DNA methylation", Blood, 2009, vol. 114, No. 16, p. 3448-3458.

Flotho, C. et al. "The DNA methyltransferase inhibitors azacitidine, decitabine and zebularine exert differential effects on cancer gene expression in acute myeloid leukemia cells", Leukemia, 2009, vol. 23, p. 1019-1028.

Guo L. et al."Combination of TRAIL and actinomycin D liposomes enhances antitumor effect in non-small cell lung cancer", International Journal of Nanomedicine, 2012, vol. 7, p. 1449-1460.

He, C. et al. "Co-delivery of chemotherapeutics and proteins for synergistic therapy", Advanced Drug Delivery Reviews, vol. 98, 2016, pp. 64-76.

Hill et al. "Characterisation of the Clinical Pharmacokinetics of Actinomycin D and the Influence of ABCB1 Pharmacogenetic Variation on Actinomycin D Disposition in Children with Cancer", Clin Pharmacokinet, 2014, vol. 53, p. 741-751.

(56) References Cited

OTHER PUBLICATIONS

Hrkach J. et al. "Preclinical Development and Clinical Translation of a PSMA-Targeted Docetaxel Nanoparticle with a Differentiated Pharmacological Profile", Science Translational Medicine, 2012, vol. 4, Issue 128, 12 pages.
Ikeda et al. "Effect of the specific P53 stabilizer CBS9106 on multiple myeloma (MM)", Journal of Clinical Oncology, 2009 ASCO Annual Meeting Proceedings (Post-Meeting Edition), 2009, vol. 27, No. 15S, p. 8601.
Inaba M. et al. "Decreased Retention of Actinomycin D as the Basis for Crossresistance in Anthracycline-resistant Sublines of P388 Leukemia", Cancer Research, 1977, vol. 37, p. 4629-4634.
McCall, R. L. et al. "PLGA Nanoparticles Formed by Single- or Double-emulsion with Vitamin ETPGS", J Journal of Visualized Experiments, 2013, vol. 82, e51015, 8 pages.
Merkel O. et al. "Actinomycin D induces p53-independent cell death and prolongs survival in high-risk chronic lymphocytic leukemia", Leukemia, 2012, vol. 26, 2508-2516.
Oki, Y. et al. "Epigenetic Mechanisms in AML—A Target for Therapy" in Acute Myelogenous Leukemia Genetics, Biology and Therapy, Nagarajan, L. (Ed.), 2010, pp. 19-40.
Osathanondh R. et al. "Actinomycin D as the Primary Agent for Gestational Trophoblastic Desease", Cancer 1975, vol. 36, p. 863-866.
Pulkkinen, M. et al. "Three-step tumor targeting of paclitaxel using biotinylated PLA-PEG nanoparticles and avidin-biotin technology: Formulation development and in vitro anticancer activity", European Journal of Pharmaceutics and Biopharmaceutics vol. 70, No. 1, 2008, pp. 66-74.
Rahman, Y. et al. "Liposome-Encapsulated Actinomycin D: Potential in Cancer Chemotherapy", Proceedings of the Society for Experimental Biology and Medicine, vol. 146, No. 4, 1974, pp. 1173-1176.
Song, Y. H. et al. "A novel in situ hydrophobic ion paring (HIP) formulation strategy for clinical product selection of a nanoparticle drug delivery system", Journal of Controlled Release, 2016, vol. 229, p. 106-119.
Tassara, M. et al. "Valproic acid in combination with all-trans retinoic acid and intensive therapy for acute myeloid leukemia in older patients", Blood Journal, 2014, vol. 123, No. 26, p. 4027-4036.
Walsh et al. "Development of a physiologically based pharmacokinetic model of actinomycin D in children with cancer", British Journal of Clinical Pharmacology, 2016, 10 pages.
Xu H. et al. "Actinomycin D Decreases Mcl-1 Expression and Acts Synergistically with ABT-737 against Small Cell Lung Cancer Cell Lines", Clinical Cancer Research, 2010, vol. 16, No. 17, p. 4392-4400.
"Cubic Phase Particles in Drug Delivery", Particle Sciences Technical Brief, 2012, vol. 4.
Particle Sciences acquires rights to LyoCell technology, North America Research, 2012, 1 page.
Cui, F., et al., "A comparative in vitro evaluation of self-assembled PTX-PLA and PTX-MPEG-PLA nanoparticles", Nanoscale Res Lett, Jun. 2, 20137; 8(1): 301, 8 pages.
Dong, Y., et al., "Methoxy poly(ethylene glycol)-poly(lactide) (MPEG-PLA) nanoparticles for controlled delivery of anticancer drugs", Biomaterials, Jun. 2004; 25(14): 2843-9.

* cited by examiner

* ActD 0.05 μM (1 h/day incubation)

** ActD 12.5 μg/kg x 5 d

FIGURE 5

| Gene | Target (exon) |
|---|---|
| ABL1 | From 4 to 6 |
| ASXL1 | 12 |
| ATRX | From 8 to 10 and from 7 to 31 |
| BCOR | All exons |
| BCORL1 | All exons |
| BRAF | 15 |
| CALR | 9 |
| CBL | 8,9 |
| CBLB | 9,10 |
| CBLC | 9,10 |
| CDKN2A | All exons |
| CEBPA | All exons |
| CSF3R | From 14 to 17 |
| CUX1 | All exons |

| Gene | Target (exon) |
|---|---|
| DNMT3A | All exons |
| ETV6/TEL | All exons |
| EZH2 | All exons |
| FBXW7 | From 9 to 11 |
| FLT3 | 14,15,20 |
| GATA1 | 2 |
| GATA2 | From 2 to 6 |
| GNAS | 8, 9 |
| HRAS | 2, 3 |
| IDH1 | 4 |
| IDH2* | 4 * |
| IKZF1 | All exons |
| JAK2 | 12, 14 |
| JAK3 | 13 |

| Gene | Target (exon) |
|---|---|
| KDM6A | All exons |
| KIT | 2, Fro m 8 to 11, 13, 17 |
| KRAS | 2, 3 |
| MLL | From 5 to 8 |
| MPL | 10 |
| MYD88 | From 3 to 5 |
| NOTCH1 | From 26 to 28, 34 |
| NPM1* | 12 * |
| NRAS | 2, 3 |
| PDGFRA | 12, 14, 18 |
| PHF6 | All exons |
| PTEN | 5, 7 |
| PTPN11 | 3, 13 |

| Gene | Target (exon) |
|---|---|
| RAD21 | All exons |
| RUNX1 | All exons |
| SETBP1 | 4 (partial) |
| SF3B1 | From 13 to 16 |
| SMC1A | 2, 11, 16, 17 |
| SMC3 | 10, 13, 19, 23, 25, 28 |
| SRSF2 | 1 |
| STAG2* | All exons * |
| TET2 | From 3 to 11 |
| TP53 | From 2 to 11 |
| U2AF1 | 2, 6 |
| WT1 | 7, 9 |
| ZRSR2 | All exons |

* Patient M.M.: *NPM1*, *IDH2* and *STAG2* mutations disappeared after act-D.

FIGURE 8
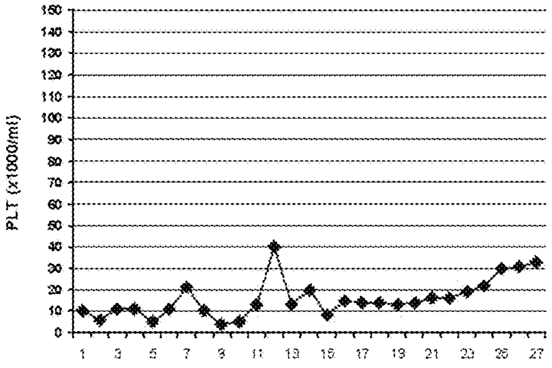
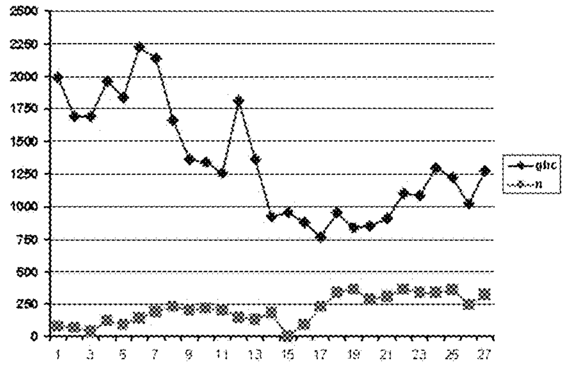

CBCs d + 46: WBC 4130/mm3, N 66%, Hb 7.7 g/dl, PLT 192.000/mm3
Epo dosage: 17,8 mUI/ml (inappropriate response)
Started on Darbopoetina

| | | | Diam. (nm) | % Intensity | Width (nm) |
|---|---|---|---|---|---|
| Z-Average (d.nm): | 176.9 | Peak 1: | 186.6 | 100.0 | 44.40 |
| PdI: | 0.040 | Peak 2: | 0.000 | 0.0 | 0.000 |
| Intercept: | 0.928 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 143.5 | Peak 1: | 169.0 | 100.0 | 66.02 |
| PdI: | 0.143 | Peak 2: | 0.000 | 0.0 | 0.000 |
| Intercept: | 0.930 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 192.4 | Peak 1: | 208.2 | 100.0 | 58.99 |
| PdI: | 0.072 | Peak 2: | 0.000 | 0.0 | 0.000 |
| Intercept: | 0.948 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 162.0 | Peak 1: | 173.7 | 100.0 | 46.15 |
| PdI: | 0.069 | Peak 2: | 0.000 | 0.0 | 0.000 |
| Intercept: | 0.946 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 182.4 | Peak 1: | 190.7 | 100.0 | 42.63 |
| PdI: | 0.022 | Peak 2: | 0.000 | 0.0 | 0.000 |
| Intercept: | 0.919 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 166.4 | Peak 1: | 168.1 | 100.0 | 41.96 |
| PdI: | 0.046 | Peak 2: | 0.000 | 0.0 | 0.000 |
| Intercept: | 0.949 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 143.4 | Peak 1: | 170.0 | 100.0 | 71.50 |
| PdI: | 0.147 | Peak 2: | 0.000 | 0.0 | 0.000 |
| Intercept: | 0.904 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 110.7 | Peak 1: | 124.7 | 100.0 | 43.77 |
| PdI: | 0.109 | Peak 2: | 0.000 | 0.0 | 0.000 |
| Intercept: | 0.961 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 123.1 | Peak 1: | 140.4 | 100.0 | 51.49 |
| PdI: | 0.118 | Peak 2: | 0.000 | 0.0 | 0.000 |
| Intercept: | 0.938 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 104.5 | Peak 1: | 120.1 | 100.0 | 46.19 |
| Pdl: | 0.124 | Peak 2: | 0.000 | 0.0 | 0.000 |
| Intercept: | 0.923 | Peak 3: | 0.000 | 0.0 | 0.000 |
| Result quality : | Good | | | | |

| | | | Diam. (nm) | % Intensity | Width (nm) |
|---|---|---|---|---|---|
| Z-Average (d.nm): | 110.7 | Peak 1: | 124.7 | 100.0 | 43.77 |
| PdI: | 0.100 | Peak 2: | 0.000 | 0.0 | 0.000 |
| Intercept: | 0.981 | Peak 3: | 0.000 | 0.0 | 0.000 |
| Result quality : | Good | | | | |

DACTINOMYCIN COMPOSITIONS AND METHODS FOR THE TREATMENT OF MYELODYSPLASTIC SYNDROME AND ACUTE MYELOID LEUKEMIA

RELATED APPLICATIONS

This application is a division of U.S. application Ser. No. 15/703,953, filed Sep. 13, 2017, now U.S. Pat. No. 10,973, 773, which claims the benefit of, and priority to, U.S. provisional application No. 62/394,104, filed Sep. 13, 2016, U.S. provisional application No. 62/444,330, filed Jan. 9, 2017, and U.S. provisional application No. 62/500,459, filed May 2, 2017, the contents of each of which are incorporated herein by reference in their entireties.

FIELD OF THE DISCLOSURE

The disclosure is directed to the field of molecular biology as it relates to genetic screening, diagnosing and treating patients having myelodysplastic syndrome or cancer.

BACKGROUND

NPM1-mutated acute myeloid leukemia (AML) is a distinct leukemia entity that accounts for one third of cases of AML in adults.

Myelodysplastic syndrome (MDS) encompasses a group of diverse bone marrow disorders affecting either red blood cells, white blood cells, and platelets in bone marrow. Progenitor stem cells that fail to mature and may accumulate in the bone marrow or have a shortened life span resulting in fewer than normal mature blood cells in the circulation. MDS has an incidence of approximately 4-5 per 100,000 of the population, increasing to 20-50 per 100,000 after age 60. MDS progresses to acute myeloid leukemia (AML) in approximately 30% of the cases.

There is a long-felt yet unmet need for effective treatments for MDS and AML, including NPM1-mutated AML.

SUMMARY

The disclosure provides for a composition comprising a therapeutically effective amount of dactinomycin encapsulated in nanoparticles comprising PLA-mPEG, wherein the nanoparticles have an average size of about 100 nm to about 200 nm.

In one embodiment, the PLA-mPEG comprises about 5% mPEG to about 50% mPEG by weight (e.g. 25%).

In one embodiment, the PLA-mPEG comprises about 15% mPEG to about 35% mPEG by weight (e.g. 25%).

In one embodiment, the molecular weight of the PLA-mPEG is about 25,000 Da to about 35,000 Da.

In one embodiment, the molecular weight of the PLA-mPEG is about 30,000 Da.

The disclosure provides for a composition comprising a therapeutically effective amount of dactinomycin encapsulated in nanoparticles comprising PLA-mPEG, wherein the molecular weight of the PLA-mPEG is about 25,000 Da to about 35,000 Da.

In one embodiment, the molecular weight of the PLA-mPEG is about 30,000 Da.

In one embodiment, the PLA-mPEG comprises about 5% mPEG to about 50% mPEG by weight (e.g. 25%).

In one embodiment, the PLA-mPEG comprises about 15% mPEG to about 35% mPEG by weight (e.g. 25%).

In one embodiment, the nanoparticles have an average size of about 100 nm to about 200 nm.

The disclosure provides for a composition comprising a therapeutically effective amount of dactinomycin encapsulated in nanoparticles comprising PLGA-mPEG, wherein the nanoparticles have an average size of about 100 nm to about 200 nm.

In one embodiment, the PLGA has a lactic acid:glycolic acid molar ratio of about 40:60 to about 60:40.

In one embodiment, the PLGA has a lactic acid:glycolic acid molar ratio of about 50:50.

In one embodiment, the PLGA-mPEG comprises about 5% mPEG to about 50% mPEG by weight (e.g. 35%).

In one embodiment, the PLA-mPEG comprises about 25% mPEG to about 45% mPEG by weight (e.g. 35%).

In one embodiment, the molecular weight of the PLGA-mPEG is about 17,000 Da to about 27,000 Da.

In one embodiment, the molecular weight of the PLGA-mPEG is about 22,000 Da.

The disclosure provides for a composition comprising a therapeutically effective amount of dactinomycin encapsulated in nanoparticles comprising PLGA-mPEG, wherein the molecular weight of the PLGA-mPEG is about 17,000 Da to about 27,000 Da.

In one embodiment, the molecular weight of the PLGA-mPEG is about 22,000 Da.

In one embodiment, the PLGA has a lactic acid:glycolic acid molar ratio of about 40:60 ratio to about 60:40.

In one embodiment, the PLGA has a lactic acid:glycolic acid molar ratio of about 50:50.

In one embodiment, the PLGA-mPEG comprises about 5% mPEG to about 50% mPEG by weight (e.g. 35%).

In one embodiment, the PLA-mPEG comprises about 25% mPEG to about 45% mPEG by weight (e.g. 35%).

In one embodiment, the nanoparticles have an average size of about 100 nm to about 200 nm.

The disclosure provides for a composition comprising a therapeutically effective amount of dactinomycin encapsulated in nanoparticles comprising poly(lactic acid) (PLA), wherein the nanoparticles have an average size of about 100 nm to about 200 nm.

In one embodiment, the PLA is ester terminated.

In one embodiment, the molecular weight of the PLA is between about 10,000 Da to about 18,000 Da.

In one embodiment, the PLA is acid terminated.

In one embodiment, the molecular weight of the PLA is about 18,000 Da to about 24,000 Da.

The disclosure provides for a composition comprising a therapeutically effective amount of dactinomycin encapsulated in nanoparticles comprising poly(lactic acid) (PLA), wherein the molecular weight of the PLA is between about 10,000 Da to about 18,000 Da.

In one embodiment, the PLA is ester terminated.

In one embodiment, the nanoparticles have an average size of about 100 nm to about 200 nm.

The disclosure provides for a composition comprising a therapeutically effective amount of dactinomycin encapsulated in nanoparticles comprising poly(lactic acid) (PLA), wherein the molecular weight of the PLA is between about 18,000 Da to about 24,000 Da.

In one embodiment, the PLA is acid terminated.

In one embodiment, the nanoparticles have an average size of about 100 nm to about 200 nm.

The present disclosure provides compositions comprising a therapeutically effective amount of dactinomycin encapsulated in nanoparticles comprising one or more polymers further comprising a surfactant.

In one embodiment, the surfactant comprises about 0.1% to about 5% by weight of each nanoparticle.

In one embodiment, the surfactant is polyvinyl alcohol.

The present disclosure provides compositions comprising a therapeutically effective amount of dactinomycin encapsulated in nanoparticles comprising one or more polymers, where the nanoparticles have an average size of about 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, 120 nm, 121 nm, 122 nm, 123 nm, 124 nm, 125 nm, 126 nm, 127 nm, 128 nm, 129 nm, 130 nm, 131 nm, 132 nm, 133 nm, 134 nm, 135 nm, 136 nm, 137 nm, 138 nm, 139 nm, 140 nm, 141 nm, 142 nm, 143 nm, 144 nm, 145 nm, 146 nm, 147 nm, 148 nm, 149 nm, 150 nm, 151 nm, 152 nm, 153 nm, 154 nm, 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, or 200 nm.

The present disclosure provides compositions comprising a therapeutically effective amount of dactinomycin encapsulated in nanoparticles comprising one or more polymers, where the nanoparticles have an average size of about 100 nm to about 110 nm, about 105 nm to about 115 nm, about 110 nm to about 120 nm, about 115 nm to about 125 nm, about 120 nm to about 130 nm, about 125 nm to about 135 nm, about 130 nm to about 140 nm, about 135 nm to about 145 nm, about 130 nm to about 140 nm, about 135 nm to about 145 nm, about 140 nm to about 150 nm, about 145 nm to about 155 nm, about 150 nm to about 160 nm, about 155 nm to about 165 nm, about 160 nm to about 170 nm, about 165 nm to about 175 nm, about 170 nm to about 180 nm, about 175 nm to about 185 nm, about 180 nm to about 190 nm, about 185 nm to about 195 nm, or about 190 nm to about 200 nm.

The present disclosure provides compositions comprising a therapeutically effective amount of dactinomycin encapsulated in nanoparticles comprising one or more polymers, where the composition comprises about 5% by weight to about 15% by weight dactinomycin.

The present disclosure provides for a method for treating a myelodysplastic syndrome (MDS) in a subject in need thereof comprising administering to the subject a therapeutically effective amount of any of the compositions comprising a therapeutically effective amount of dactinomycin encapsulated in nanoparticles comprising one or more polymers described herein.

The present disclosure provides for a method for treating cancer in a subject in need thereof comprising administering to the subject a therapeutically effective amount of any of the compositions comprising a therapeutically effective amount of dactinomycin encapsulated in nanoparticles comprising one or more polymers described herein.

In one embodiment, the cancer is acute myeloid leukemia (AML), chronic lymphocytic leukemia (CLL), colorectal cancer, neuroendocrine cancer, esophageal cancer, and/or gastrointestinal stromal tumor (GIST).

The present disclosure provides for a method for treating a myelodysplastic syndrome (MDS) in a subject in need thereof comprising administering to the subject a therapeutically effective amount of any of the compositions comprising a therapeutically effective amount of dactinomycin encapsulated in nanoparticles comprising one or more polymers described herein, where the method further comprises administering a therapeutically effective amount of at least one additional chemotherapeutic drug selected from the group consisting of a topoisomerase inhibitor, a platinum-based therapy, an anthracycline antibiotic, a taxane, a tyrosine kinase inhibitor, a nucleoside analog, a FMS-like tyrosine kinase 3 (FLT3) inhibitor, and a hyper methylation inhibitor, wherein the molar ratio of the topoisomerase inhibitor, platinum-based therapy, anthracycline antibiotic, taxane, tyrosine kinase inhibitor, nucleoside analog, FLT3 inhibitor, and hyper methylation inhibitor to dactinomycin is 7:1, 6:1, 5:1, 4:1, 3:1, 2:1, 1:1, <1:1 or any ratio in between.

The present disclosure provides for a method for treating cancer in a subject in need thereof comprising administering to the subject a therapeutically effective amount of any of the compositions comprising a therapeutically effective amount of dactinomycin encapsulated in nanoparticles comprising one or more polymers described herein, where the method further comprises administering a therapeutically effective amount of at least one additional chemotherapeutic drug selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor, wherein the molar ratio of the topoisomerase inhibitor, platinum-based therapy, anthracycline antibiotic, taxane, tyrosine kinase inhibitor, nucleoside analog, FLT3 inhibitor, and hyper methylation inhibitor to dactinomycin is 7:1, 6:1, 5:1, 4:1, 3:1, 2:1, 1:1, <1:1 or any ratio in between.

Any of the compositions described herein are suitable for use in treating cancer, (e.g., acute myeloid leukemia (AML), chronic lymphocytic leukemia (CLL), colorectal cancer, neuroendocrine cancer, esophageal cancer, and/or gastrointestinal stromal tumor (GIST)) and/or for use in treating MDS in a subject. Any of the compositions of the disclosure are administered to the subject systemically, intravenously, by infusion, or orally.

Any of the compositions of the disclosure are administered to the subject once daily, once a week, twice a week, or once every 3 weeks.

In some embodiments, any of the compositions of the disclosure are administered to the subject once daily, once a week, twice a week, or once every 3 weeks, where the treatment further comprises a drug holiday of one, two, three, or four weeks between dosing periods or doses.

Any of the compositions of the disclosure are administered to the subject once or twice over a period of 1, 2, or 3 weeks.

In some embodiments, any of the compositions of the disclosure are administered to the subject once or twice over a period of 1, 2, or 3 weeks, where the treatment further comprises a drug holiday of one, two, three, or four weeks between dosing periods or doses.

In one embodiment, the methods of the disclosure include those where the subject suffers from or is at risk for developing mucositis.

The methods of the disclosure include those where the subject is being treated concurrently for symptoms of mucositis with one or more anti-inflammatory agents and/or antioxidants.

The methods of the disclosure include those where the subject is pre-treated for symptoms of mucositis with one or more anti-inflammatory agents and/or antioxidants prior to administration of any of the compositions described herein.

In one embodiment, the compositions and methods of the disclosure include those where the therapeutically effective amount of dactinomycin results in an $AUC_\infty$ of about 0.05 to about 2.0 mg*min/L.

In one embodiment, the compositions and methods of the disclosure include those where the therapeutically effective amount of dactinomycin results in an AUC of about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 10.25, 1.30, 1.35, 1.40, 1.45, 1.50, 1.55, 1.60, 1.65, 1.70, 1.75, 1.80, 1.85, 1.90, 1.95, or 2.0 mg*min/L.

In one embodiment, the compositions and methods of the disclosure include those where the therapeutically effective amount of dactinomycin results in an $AUC_{\infty}$ of about 0.05 to about 1.0 mg*min/L.

In one embodiment, the compositions and methods of the disclosure include those where the therapeutically effective amount of dactinomycin results in a $C_{max}$ of about 1 ng/mL to about 30 ng/mL.

In one embodiment, the compositions and methods of the disclosure include those where the therapeutically effective amount of dactinomycin results in a $C_{max}$ of about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30 ng/mL.

In one embodiment, the compositions and methods of the disclosure include those where the therapeutically effective amount of dactinomycin results in a $C_{max}$ of about 1 ng/mL to about 20 ng/mL.

In one embodiment, the compositions and methods of the disclosure include those where the therapeutically effective amount of dactinomycin results in a $C_{max}$ of about 1 ng/mL to about 5 ng/mL, about 5 ng/mL to about 10 ng/mL, about 10 ng/mL to about 15 ng/mL, or about 15 ng/mL to about 20 ng/mL.

In one embodiment, the compositions and methods of the disclosure include those where about 60% to about 90% of the dactinomycin is released from the nanoparticles after 2, 3, 4 or 5 days.

In one embodiment, the compositions and methods of the disclosure include those where about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the dactinomycin is released from the nanoparticles after 2, 3, 4, or 5 days.

In one embodiment, the compositions and methods of the disclosure include those where about 60% to about 90% of the dactinomycin is released from the nanoparticles after 3 days.

In one embodiment, the compositions and methods of the disclosure include those where about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the dactinomycin is released from the nanoparticles after 3 days.

In one embodiment, the compositions and methods of the disclosure include those where about 70% to about 80% of the dactinomycin is released from the nanoparticles after 2, 3, 4, or 5 days.

In one embodiment, the compositions and methods of the disclosure include those where about 70% to about 80% of the dactinomycin is released from the nanoparticles after 3 days.

The present disclosure also provides for a process for preparing any of the compositions of the disclosure, comprising:

(i) adding a solution of dactinomycin in organic solvent to a solution of the polymer in organic solvent until the polymer:API ratio is 10:1 ratio (weight/weight);

(ii) vortexing the solution from (i) until homogeneous (iii) adding the solution from (ii) dropwise into a water phase containing 2% (w/w) polyvinyl alcohol, with a molecular weight of 9,000-10,000 Da, 80% hydrolyzed, while said water phase was on high vortex, until the ratio of the solution from (ii) to the water phase was about 1:7, by volume, forming a nanoparticle emulsion;

(iv) vortexing the emulsion from (iii);

(v) sonicating the emulsion from (iv) for several minutes at 0° C. followed by pouring the emulsion into a stirring water phase solution containing 2% (w/w) polyvinyl alcohol, and continue stirring until organic solvent evaporates; and, optionally:

(vi) purifying the composition by centrifugation for about 30 minutes at 14,000× rpm;

(vii) discarding the supernatant from (vi), followed by washing the resulting nanoparticles with $ddH_2O$, centrifugation for 30 minutes at 14,000× rpm;

(viii) resuspending the product from (viii) in $ddH_2O$ followed by centrifugation for 5 minutes at 3500× rpm; and (ix) collecting the supernatant from (viii) and then concentrating by an Amicon® Ultra Centrifugal filter (50 kD cut-off), followed by centrifugation for 10 minutes at 14,000× rpm to remove free dactinomycin.

In one embodiment, the process for preparing any of the compositions of the disclosure, the amount of free dactinomycin in the composition is less than 5%, 4%, 3%, 2%, or 1% by weight of the amount of dactinomycin encapsulated in nanoparticles.

This disclosure provides for dactinomycin compositions, i.e., compositions comprising dactinomycin, for example, dactinomycin encapsulated in or associated with a nanoparticle. As used herein, dactinomycin may also interchangeably be referred to as actinomycin-D, act-D, actD, act D, or the like.

The disclosure provides a method for treating cancer in a subject in need thereof comprising administering to the subject a therapeutically effective amount of a composition of the disclosure. In certain embodiments, the cancer may be acute myeloid leukemia (AML), chronic lymphocytic leukemia (CLL), colorectal cancer, neuroendocrine cancer, esophageal cancer, or gastrointestinal stromal tumor (GIST). In certain embodiments, the cancer may be acute myeloid leukemia (AML). In certain embodiments, the AML may be NPM1-mutated AML or wild type AML. In certain embodiments, the AML may be NPM1-mutated AML.

The disclosure provides a method for treating a myelodysplastic syndrome (MDS) in a subject in need thereof comprising administering to the subject a therapeutically effective amount of a composition of the disclosure.

In certain embodiments, the method may further comprise administering a therapeutically effective amount of one or more additional chemotherapeutic drugs selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor. In certain embodiments, the topoisomerase inhibitor may comprise etoposide. In certain embodiments, the platinum-based therapy may comprise cisplatin. In certain embodiments, the anthracycline may comprise daunorubicin, doxorubicin, epirubicin, or idarubicin. In certain embodiments, the taxane may comprise paclitaxel or docetaxel. In certain embodiments, the tyrosine kinase inhibitor may comprise imatinib. In certain embodiments, the nucleoside analog may comprise cytarabine, gemcitabine or capecitabine. In certain embodiments, the FLT3 inhibitor may comprise Rydapt® (midostaurin), sorafenib, lestaurtinib, quizartinib, ponatinib, crenolanib, or gliteritinib, In certain embodiments, the hyper methylation inhibitor may comprise azacitidine, decitabine, and zebularine.

In certain embodiments the molar ratio of the topoisomerase inhibitor, platinum-based therapy, anthracycline antibiotic, taxane, tyrosine kinase inhibitor, or nucleoside analog to dactinomycin is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or any ratio in between. In certain embodiments the molar ratio is 10:1, 9:1, 8:1, 7:1, 6:1, 5:1, 4:1, 3:1, 2:1, 1:1 or any ratio in between. In certain embodiments the molar ratio is 7:1, 6:1, 5:1, 4:1, 3:1 or any ratio in between. In certain embodiments the molar ratio is about 5:1. In certain embodiments the molar ratio is 5:1.

The disclosure provides a method for treating a myelodysplastic syndrome (MDS) and/or a method for treating cancer in a subject in need thereof comprising administering to the subject a therapeutically effective amount of a composition of the disclosure and at least east one of etoposide, citosine-arabinoside (ara-C, cytarabine), and oxaliplatinum.

The disclosure provides a method for treating a myelodysplastic syndrome (MDS) and/or a method for treating cancer in a subject in need thereof comprising administering to the subject a therapeutically effective amount of a composition of the disclosure and cytarabine.

Compositions of the disclosure may further comprise a therapeutically effective amount of an anti-inflammatory agent, an antioxidant, or a combination thereof. Methods of the disclosure may further comprise administering to the subject a therapeutically effective amount of an anti-inflammatory agent, an antioxidant, or a combination thereof.

Anti-inflammatory agents of the disclosure may comprise pentoxifylline and/or nonsteroidal anti-inflammatory drugs (NSAIDs).

Antioxidants of the disclosure may comprise vitamin C, N-acetyl cysteine, amifostine, or retinoic acid (e.g., all trans-retinoic acid). In certain embodiments, antioxidants of the disclosure may comprise vitamin C, retinoic acid (e.g., all trans-retinoic acid), or combination thereof.

In certain embodiments, the anti-inflammatory agent may comprise pentoxifylline and/or NSAIDs and the antioxidant may comprise vitamin C or retinoic acid (e.g., all trans-retinoic acid). In certain embodiments, the anti-inflammatory agent may comprise pentoxifylline and/or NSAIDs, and the antioxidant may comprise vitamin C, retinoic acid (e.g., all trans-retinoic acid), or a combination thereof.

In certain embodiments, the molar ratio of the anti-inflammatory agent, antioxidant, or combination thereof, to dactinomycin is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or any ratio in between.

Methods of the disclosure comprise administration of a composition of the disclosure, e.g., a composition comprising a therapeutically effective amount of dactinomycin encapsulated in nanoparticles, and at least one of (a) the anti-inflammatory agent, (b) the antioxidant, and (c) the combination of the anti-inflammatory agent and the antioxidant; wherein the dactinomycin and the anti-inflammatory agent, antioxidant, or any combination thereof are administered simultaneously.

Methods of the disclosure comprise administration of a composition of the disclosure, e.g., a composition comprising a therapeutically effective amount of dactinomycin encapsulated in nanoparticles, and at least one of (a) the anti-inflammatory agent, (b) the antioxidant, and (c) the combination of the anti-inflammatory agent and the antioxidant; wherein the dactinomycin and the anti-inflammatory agent, antioxidant, or any combinations thereof are administered sequentially.

Compositions of the disclosure comprising dactinomycin may be administered to the subject systemically. In certain embodiments, compositions of the disclosure comprising dactinomycin may be administered intravenously or by infusion. In certain embodiments, compositions of the disclosure comprising dactinomycin may be administered orally. In certain embodiments, compositions of the disclosure comprising dactinomycin may be administered in the form of a tablet or capsule.

Compositions of the disclosure comprising dactinomycin, e.g., a composition comprising a therapeutically effective amount of dactinomycin encapsulated in nanoparticles, may be administered in a therapeutically effective amount of the composition of between 1 and 30 μg/kg/day, inclusive of the endpoints. In certain embodiments, compositions of the disclosure comprising dactinomycin may be administered in a therapeutically effective amount of the composition of between 10 and 20 μg/kg/day or between 10 and 15 μg/kg/day, inclusive of the endpoints.

In certain embodiments, compositions of the disclosure comprising dactinomycin may be administered in a therapeutically effective amount of the composition of about 1 μg/kg/day, 2 μg/kg/day, 3 μg/kg/day, 4 μg/kg/day, 5 μg/kg/day, 6 μg/kg/day, 7 μg/kg/day, 8 μg/kg/day, 9 μg/kg/day, 10 μg/kg/day, 11 μg/kg/day, 12 μg/kg/day, 13 μg/kg/day, 14 μg/kg/day, 15 μg/kg/day, 16 μg/kg/day, 17 μg/kg/day, 18 μg/kg/day, 19 μg/kg/day, 20 μg/kg/day, 21 μg/kg/day, 22 μg/kg/day, 23 μg/kg/day, 24 μg/kg/day, 25 μg/kg/day, 26 μg/kg/day, 27 μg/kg/day, 28 μg/kg/day, 29 μg/kg/day, or 30 μg/kg/day.

Compositions of the disclosure comprising dactinomycin, e.g., a composition comprising a therapeutically effective amount of dactinomycin encapsulated in nanoparticles, may be administered in a therapeutically effective amount of the composition of about 5 μg/kg/day to about 15 μg/kg/day. In certain embodiments, compositions of the disclosure comprising dactinomycin may be administered in a therapeutically effective amount of the composition of 5 μg/kg/day to 15 μg/kg/day. In certain embodiments, compositions of the disclosure comprising dactinomycin may be administered in a therapeutically effective amount of the composition of about 12.5 μg/kg/day. In certain embodiments, compositions of the disclosure comprising dactinomycin may be administered in a therapeutically effective amount of the composition of 12.5 μg/kg/day.

Compositions of the disclosure comprising dactinomycin a composition comprising a therapeutically effective amount of dactinomycin encapsulated in nanoparticles, may be administered once a day. In a certain embodiment, compositions of the disclosure comprising dactinomycin may be administered twice a day.

Compositions of the disclosure comprising dactinomycin, e.g., a composition comprising a therapeutically effective amount of dactinomycin encapsulated in nanoparticles, may be administered twice a week. In a certain embodiment, compositions of the disclosure comprising dactinomycin may be administered once a week. In a certain embodiment, compositions of the disclosure comprising dactinomycin may be administered once every two weeks.

The total dose administered over a course of treatment will be depend on the amount administered per dose, the frequency of the administration, and/or the duration of the treatment period.

For example, if the amount of the composition administered is 10 μg/kg/day, the frequency of the dose is once a day, and the duration of the treatment period is one week, the total dose administered will be 70 μg/kg.

For example, if the amount of the composition administered is 10 μg/kg/day, the frequency of the dose is twice a week (e.g., on days 1 and 4), and the duration of the treatment period is one week, the total dose administered will be 70 μg/kg, provided twice during the week in a 35 μg/kg dose.

For example, if the amount of the composition administered is 10 μg/kg/day, the frequency of the dose is once a week, and the duration of the treatment period is one week, the total dose administered will be 70 μg/kg, provided once during the week in a 70 μg/kg dose.

For example, if the amount of the composition administered is 10 μg/kg/day, the frequency of the dose is once every two weeks, and the duration of the treatment period is two weeks, the total dose administered will be 140 μg/kg, provided once during the two week period.

Determination of the total dose administered to the subject is within the routine level of skill in the art.

Compositions of the disclosure comprising dactinomycin, e.g., a composition comprising a therapeutically effective amount of dactinomycin encapsulated in nanoparticles, may be administered for at least one cycle. In certain embodiments, compositions of the disclosure comprising dactinomycin may be administered for at least two cycles. A cycle, in one aspect of the disclosure, may comprise 5 consecutive days of treatment with the compositions of the disclosure. In one embodiment, a cycle may comprise treatment with the compositions of the disclosure daily, twice a week, once a week, or once every two weeks.

In certain embodiments, the treatment further comprises a drug holiday of one, two, three, four, or more weeks between doses and/or treatment cycles 8. In one embodiment, the drug holiday between two consecutive treatment cycles may be at least two weeks. In one embodiment, the drug holiday between two consecutive treatment cycles may be at least four weeks.

The methods of this disclosure may further comprise the step of administering a blood transfusion to the subject. In certain embodiments, a composition of the disclosure comprising dactinomycin, e.g., a composition comprising a therapeutically effective amount of dactinomycin encapsulated in nanoparticles, and a blood transfusion may be administered simultaneously. Alternatively, a composition of the disclosure comprising dactinomycin and a blood transfusion may be administered sequentially. In certain embodiments, a composition of the disclosure comprising dactinomycin may be administered before the blood transfusion. For example, a cycle of administration of the composition comprising dactinomycin may be completed and the blood transfusion may be administered after the cycle of dactinomycin therapy or between two cycles of dactinomycin therapy. In certain embodiments, a blood transfusion may be administered following at least one cycle of treatment with a composition of the disclosure comprising dactinomycin.

Subjects of the disclosure may have mucositis prior to or following initiation of treatment with dactinomycin. Subjects of the disclosure may be predisposed to develop or at risk of developing mucositis. In certain embodiments in which a subject already has or may develop mucositis, the therapeutically effective amount of a composition comprising dactinomycin or a therapeutically effective amount of dactinomycin may be an amount sufficient to treat cancer (e.g. AML or NPM1-mutated AML) without inducing or exacerbating mucositis in the subject.

In certain embodiments in which a subject already has or may develop mucositis, the therapeutically effective amount of a composition comprising dactinomycin or a therapeutically effective amount of dactinomycin may be an amount sufficient to treat myelodysplastic syndrome (MDS) without inducing or exacerbating mucositis in the subject.

In certain embodiments in which a subject may develop or be susceptible to mucositis, the method of the disclosure comprises concurrent treatment of the subject for symptoms of mucositis with one or more anti-inflammatory agents and/or antioxidants.

In certain embodiments in which a subject already has mucositis, the method of the disclosure comprises pretreatment of the subject for symptoms of mucositis with one or more anti-inflammatory agents and/or antioxidants prior to administration of any of the compositions described herein.

According to methods of the disclosure, compositions of the disclosure comprising dactinomycin may be administered as a preferred, frontline therapy, for subjects having newly diagnosed and/or previously untreated AML. In certain embodiments, the subject may be unfit for intensive chemotherapy. In certain embodiments, the subject may be at least 50 years of age. In certain embodiments, the subject may be at least 60 years of age. In certain embodiments, the subject may be at least 70 years of age. In certain embodiments, subjects who may be unfit for intensive chemotherapy include, but are not limited to, subjects who may have a compromised immune system, a blood disorder, an intestinal disorder, or an infection.

According to methods of the disclosure, a subject did not respond to another cancer therapy prior to administration of the dactinomycin compositions of the disclosure. In certain embodiments, the other cancer therapy comprises azacitidine. In certain embodiments, a subject may relapse after the other cancer therapy. In certain embodiments, upon treatment with any of the dactinomycin compositions of the disclosure, a subject may subsequently enter remission. In certain embodiments, the term remission includes morphological and/or molecular remission.

In certain embodiments, the therapeutically effective amount of dactinomycin encapsulated in nanoparticles results in a $C_{max}$ between 1 ng/mL and 30 ng/mL, inclusive of the endpoints. For example, the therapeutically effective amount of dactinomycin encapsulated in nanoparticles results in a $C_{max}$ of about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, or 30 ng/mL.

In certain embodiments, the therapeutically effective amount of dactinomycin encapsulated in and/or associated with nanoparticles results in a $C_{max}$ between 1 ng/mL and 20 ng/mL, inclusive of the endpoints.

In certain embodiments, the therapeutically effective amount of dactinomycin encapsulated in and/or associated with nanoparticles is between 10 and 15 ng/mL.

In certain embodiments, the therapeutically effective amount of dactinomycin encapsulated in and/or associated with nanoparticles results in an $AUC_{\infty}$ of about 0.05 to about 2.0 mg*min/L. In one embodiment, the therapeutically effective amount of dactinomycin encapsulated in and/or associated with nanoparticles results in an $AUC_{\infty}$ of about 0.05 to about 1.0 mg*min/L.

This disclosure provides a composition comprising a therapeutically effective amount of dactinomycin, wherein the dactinomycin is encapsulated in and/or associated with nanoparticles, further comprising a therapeutically effective amount of one or more additional chemotherapeutic drugs selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor, wherein the chemotherapeutic drug is encapsulated in and/or associated with nanoparticles.

This disclosure provides a composition comprising a therapeutically effective amount of dactinomycin, wherein the dactinomycin is encapsulated in and/or associated with nanoparticles, further comprising a therapeutically effective amount of one or more additional chemotherapeutic drugs selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor, wherein the chemotherapeutic drug is encapsulated in and/or associated with to a nanoparticle, wherein the topoisomerase inhibitor may comprise etoposide; the platinum-based therapy may comprise cisplatin; the anthracycline may comprise daunorubicin, doxorubicin, epirubicin, or idarubicin; the taxane may comprise paclitaxel or docetaxel; the tyrosine kinase inhibitor may comprise imatinib; the nucleoside analog may comprise cytarabine, gemcitabine or capecitabine; the FLT3 inhibitor may comprise Rydapt® (midostaurin), sorafenib, lestaurtinib, quizartinib, ponatinib, crenolanib, or gliteritinib; and/or the hyper methylation inhibitor may comprise azacitidine, decitabine, and zebularine.

This disclosure provides a composition comprising a therapeutically effective amount of dactinomycin, wherein the dactinomycin is encapsulated in and/or associated with nanoparticles, further comprising a therapeutically effective amount of a chemotherapeutic drug selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor, wherein the molar ratio of the topoisomerase inhibitor, platinum-based therapy, anthracycline antibiotic, taxane, tyrosine kinase inhibitor, or nucleoside analog to dactinomycin is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or any ratio in between. In certain embodiments the molar ratio is 10:1, 9:1, 8:1, 7:1, 6:1, 5:1, 4:1, 3:1, 2:1, 1:1 or any ratio in between. In certain embodiments the molar ratio is 7:1, 6:1, 5:1, 4:1, 3:1 or any ratio in between. In certain embodiments the molar ratio is about 5:1. In certain embodiments the molar ratio is 5:1.

The disclosure provides a composition comprising a therapeutically effective amount of dactinomycin and etoposide, wherein the dactinomycin and etoposide are encapsulated in and/or associated with nanoparticles, and wherein the therapeutically effective amount etoposide results in a $C_{max}$ of less than 50 μg/mL. In certain embodiments, the therapeutically effective amount of etoposide encapsulated in and/or associated with nanoparticles results in a $C_{max}$ of between 1 and 50 μg/mL, inclusive of the endpoints.

In certain embodiments, the therapeutically effective amount of etoposide are encapsulated in and/or associated with nanoparticles is between 30 and 45 mg/kg/day.

In certain embodiments, the therapeutically effective amount of etoposide are encapsulated in and/or associate with nanoparticles results in an $AUC_{\infty}$ of about 50 to about 60 μg*hour/mL/hour.

This disclosure provides a composition comprising a therapeutically effective amount of dactinomycin and etoposide, wherein the dactinomycin and etoposide are encapsulated in nanoparticles, wherein the molar ratio of the etoposide to dactinomycin is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or any ratio in between. In certain embodiments the molar ratio is 10:1, 9:1, 8:1, 7:1, 6:1, 5:1, 4:1, 3:1, 2:1, 1:1 or any ratio in between. In certain embodiments the molar ratio is 7:1, 6:1, 5:1, 4:1, 3:1 or any ratio in between. In certain embodiments the molar ratio is about 5:1. In certain embodiments the molar ratio is 5:1.

The disclosure provides a method for treating a myelodysplastic syndrome (MDS) and/or a method for treating or cancer in a subject in need thereof comprising administering to the subject a therapeutically effective amount of any composition described herein, for example, e.g., a composition comprising a therapeutically effective amount of dactinomycin encapsulated in nanoparticles. In certain embodiments, the cancer is acute myeloid leukemia (AML), chronic lymphocytic leukemia (CLL), colorectal cancer, neuroendocrine cancer, esophageal cancer, or gastrointestinal stromal tumor (GIST). In one embodiment, the cancer is acute myeloid leukemia (AML). In a preferred embodiment, the cancer is NPM1-mutated AML.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the compositions is administered once every week. In certain embodiments, the composition is administered twice every week. In certain embodiments, the compositions are administered once every two weeks. In certain embodiments, the compositions are administered once every month.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the compositions is administered once every week, twice every week, once every two weeks, or once every month, wherein the composition is administered again after a drug holiday of one, two, three, four, or more weeks. In one embodiment, the drug holiday between two consecutive treatment cycles may be at least two weeks. In one embodiment, the drug holiday between two consecutive treatment cycles may be at least four weeks.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering to the subject a therapeutically effective amount of an anti-inflammatory agent, an antioxidant, or a combination thereof. In certain embodiments, the anti-inflammatory agent comprises pentoxifylline and/or NSAIDs. In certain embodiments, the antioxidant comprises vitamin C and/or retinoic acid (e.g., all trans-retinoic acid). In certain embodiments, the anti-inflammatory agent comprises pentoxifylline and/or NSAIDs, and the antioxidant comprises vitamin C or retinoic acid (e.g., all trans-retinoic acid).

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering to the subject a therapeutically effective amount of an anti-inflammatory agent, an antioxidant, or a combination thereof, wherein the molar ratio of the anti-inflammatory agent, antioxidant, or combination thereof, to dactinomycin is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or any ratio in between.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering to the subject a therapeutically effective amount of an anti-inflammatory agent, an antioxidant, or a combination thereof, wherein the composition and at least one of (a) the anti-inflammatory agent,
(b) the antioxidant, and
(c) the combination of the anti-inflammatory agent and the antioxidant; wherein the dactinomycin and the anti-inflammatory agent, antioxidant, or combination thereof are administered simultaneously.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering to the subject a therapeutically effective amount of an anti-inflammatory agent, an antioxidant, or a combination thereof, wherein the composition and at least one of (a) the anti-inflammatory agent,
(b) the antioxidant, and
(c) the combination of the anti-inflammatory agent and the antioxidant; wherein the dactinomycin and the anti-inflammatory agent, antioxidant, or combination thereof are administered sequentially.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the composition further comprises a pharmaceutically acceptable carrier.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the composition further comprises a pharmaceutically acceptable carrier and the composition is administered systemically. In certain embodiments, the composition is administered intravenously. In certain embodiments, the composition is administered by infusion.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the composition further comprises a pharmaceutically acceptable carrier and the composition is administered orally. In certain embodiments, the composition is in the form of a tablet. In certain embodiments, the composition is in the form of a capsule.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering a blood transfusion to the subject. In certain embodiments, the composition and the blood transfusion are administered simultaneously. In certain embodiments, the composition and the blood transfusion are administered sequentially. In certain embodiments, the composition is administered before the blood transfusion. In certain embodiments, the blood transfusion is administered following the at least one cycle of treatment with the composition.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the subject has mucositis. In one embodiment, the treatment further comprises treatment with at least one additional chemotherapeutic drug selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the subject may develop or is susceptible to mucositis. In one embodiment, the treatment further comprises treatment with at least one additional chemotherapeutic drug selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the subject is at least 50 years of age. In a certain embodiment, the subject is at least 60 years of age. In a certain embodiment, the subject is at least 70 years of age.

The disclosure provides a method for treating cancer in a subject in need thereof comprising administering to the subject a therapeutically effective amount of any composition described herein, e.g., a composition comprising a therapeutically effective amount of dactinomycin encapsulated in nanoparticles, wherein the subject did not respond to another cancer therapy prior to administration of the composition. In certain embodiments, the other cancer therapy is azacitidine.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the subject relapsed after the other cancer therapy. In certain embodiments, the other cancer therapy is azacitidine. In certain embodiments, the remission is morphological remission. In certain embodiments, the remission is molecular remission.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering a therapeutically effective amount of one or more additional chemotherapeutic drugs selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor.

In certain embodiments, the platinum-based therapy comprises cisplatin.

In certain embodiments, the anthracycline comprises daunorubicin, doxorubicin, epirubicin, or idarubicin.

In certain embodiments, the taxane comprises paclitaxel or docetaxel.

In certain embodiments, the nucleoside analog comprises cytarabine, gemcitabine or capecitabine.

In certain embodiments, the FLT3 inhibitor comprises Rydapt® (midostaurin), sorafenib, lestaurtinib, quizartinib, ponatinib, crenolanib, or gliteritinib, In certain embodiments, the hyper methylation inhibitor comprises azacitidine, decitabine, and zebularine.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering a therapeutically effective amount of at least one additional chemotherapeutic drug selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor, wherein the molar ratio of the topoisomerase inhibitor, platinum-based therapy, anthracycline antibiotic, taxane, tyrosine kinase inhibitor, nucleoside analog, FLT3 inhibitor, or hyper methylation inhibitor to dactinomycin is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 or any ratio in between. In certain embodiments the molar ratio is 10:1, 9:1, 8:1, 7:1, 6:1, 5:1, 4:1, 3:1, 2:1, 1:1 or any ratio in between. In certain embodiments the molar ratio is 7:1, 6:1, 5:1, 4:1, 3:1 or any ratio in between. In certain embodiments the molar ratio is about 5:1. In certain embodiments the molar ratio is 5:1.

The disclosure provides a method for treating a myelodysplastic syndrome (MDS) and/or a method for treating cancer in a subject in need thereof comprising administering to the subject a therapeutically effective amount of any composition described herein, e.g., a composition comprising a therapeutically effective amount of dactinomycin encapsulated in nanoparticles, wherein the method further comprises administering to the subject retinoic acid (e.g., all trans-retinoic acid), valproic acid, a histone deacteylase inhibitor, a proteasome inhibitor, a farnesyltransferase inhibitor, a p53 stabilizer, or any combination thereof.

The disclosure provides a method for treating a myelodysplastic syndrome (MDS) and/or a method for treating cancer in a subject in need thereof comprising administering to the subject a therapeutically effective amount of a composition comprising dactinomycin, e.g., a composition comprising a therapeutically effective amount of dactinomycin encapsulated in nanoparticles.

The disclosure provides compositions and methods for the treatment of AML, and, in particular, the treatment of NPM1-mutated AML that addresses the underlying pathology in addition to the clinical symptoms of AML. (Döhner, H. et al. *N. Engl. J. Med.* 2015, 373: 1136-1152.)

The disclosure provides a method for treating acute myeloid leukemia (AML) in a subject in need thereof comprising administering to the subject a therapeutically effective amount of a composition comprising dactinomycin, e.g., a composition comprising a therapeutically effective amount of dactinomycin encapsulated in nanoparticles, In preferred methods, the AML is NPM1-mutated AML. In certain embodiments, the NPM1-mutated AML does not have FLT3 internal tandem duplication repeats.

According to the methods of the disclosure, a therapeutically effective amount of the composition is between 1 and 30 μg/kg/day or between 1 and 20 μg/kg/day, inclusive of the endpoints. Low dosages are effective over longer periods of time. For example, a dose of 1 μg/kg/day may be used for a long-term daily and/or maintenance dosage to prevent relapse. High dosages may be used safely for shorter periods of time. For example, 30 μg/kg/day may be used for one day when followed by a decreased dosage or a period of non-treatment, for example, a period of two-weeks of non-treatment between single-day treatment cycles. Alternatively, a high dose may be used to quickly increase or spike the blood plasma levels above a minimum effective threshold when followed the next day or following a non-treatment period with a lower dose to maintain blood plasma concentration of the dactinomycin. In certain embodiments of the methods of the disclosure, the therapeutically effective amount of the composition is about 5 μg/kg/day to about 15 μg/kg/day or is 5 μg/kg/day to 15 μg/kg/day. Alternatively, the therapeutically effective amount of the composition is about 12.5 μg/kg/day or is 12.5 μg/kg/day. The therapeutically effective amount of the composition may be administered once per day or at least once per day, twice a week, once every week, or once every two weeks.

According to methods of the disclosure, a composition comprising a therapeutically effective amount of dactinomycin encapsulated in nanoparticles may be administered as a preferred, frontline therapy, for subjects having newly diagnosed and/or previously untreated AML who are unfit for intensive chemotherapy or the elderly (i.e. subjects 60 year of age or older). Subjects who may be unfit for intensive chemotherapy include, but are not limited, to subject who have a compromised immune system, a blood disorder, an intestinal disorder, or an infection.

According to methods of the disclosure, a subject treated with a dactinomycin composition e.g., a composition comprising a therapeutically effective amount of dactinomycin encapsulated in nanoparticles, may subsequently enter remission. As used herein, the term remission includes morphological and/or molecular remission.

Any of the methods of the disclosure may further comprise administering to the subject retinoic acid (e.g., all trans-retinoic acid), valproic acid, a histone deacteylase inhibitor, a proteasome inhibitor, a farnesyltransferase inhibitor, a p53 stabilizer, or any combination thereof.

This disclosure provides for a composition comprising a therapeutically effective amount of dactinomycin, e.g., a composition comprising a therapeutically effective amount of dactinomycin encapsulated in nanoparticles, wherein the therapeutically effective amount of dactinomycin is about 15 μg/kg/day or is 15 μg/kg/day.

This disclosure provides for a method for treating a myelodysplastic syndrome (MDS) and/or a method for treating cancer in a subject in need thereof comprising administering to the subject a composition comprising a therapeutically effective amount of dactinomycin, e.g., a composition comprising a therapeutically effective amount of dactinomycin encapsulated in nanoparticles, wherein the therapeutically effective amount of dactinomycin is about 15 μg/kg/day or is 15 μg/kg/day.

BRIEF DESCRIPTION OF THE DRAWINGS

FIG. 5 is a chart showing sequencing by the TruSight Myeloid Panel.—mutated genes (*). Patient M.M. NMP1, IDH2 and STAG2 mutations not detected after act-D.

FIG. 8 is a pair of graphs depicting hematological recovery following one cycle of dactinomycin treatment.

(FIG. 28A: 100DL mPEG 5000 (25%); FIG. 28B: Resomer® 5050DLG mPEG 5000 (35%); FIG. 28C: Resomer® R 203 H; FIG. 28D: Resomer® R 202 S).

DETAILED DESCRIPTION

Figure 1A:
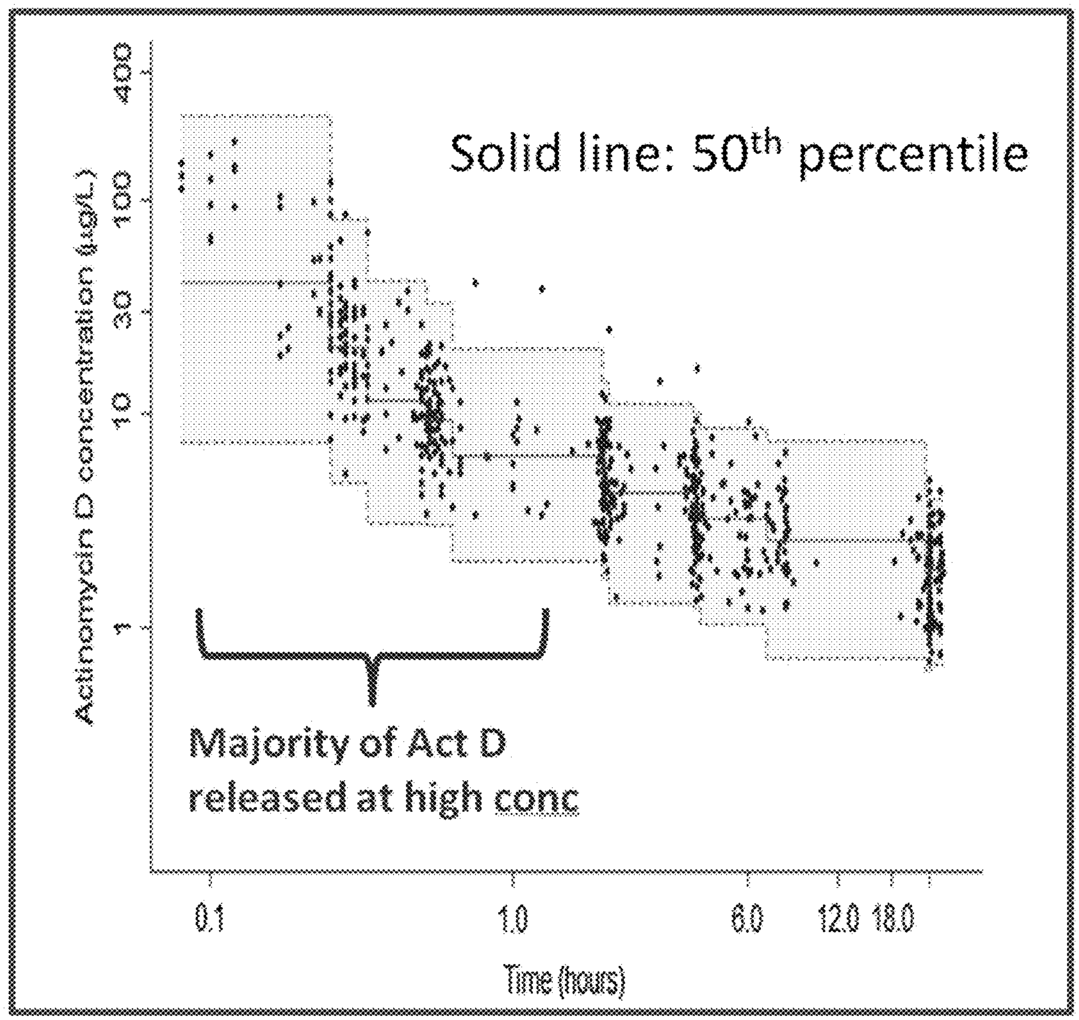
FIGS. 1A and B are each graphs demonstrating the systemic concentration of dactinomycin over time. The data in these graphs are taken from 21 patients aged 16-53 years, administered with 1 $mg/m^2$ (27 μg/kg) of dactinomycin. (See Hill, C. R. et al. Clin. Pharmacokinet. (2014) 53:741-751; and Walsh, C. et al. Br J Clin Pharmacol (2016)) 81:989-998)
Figure 1B:
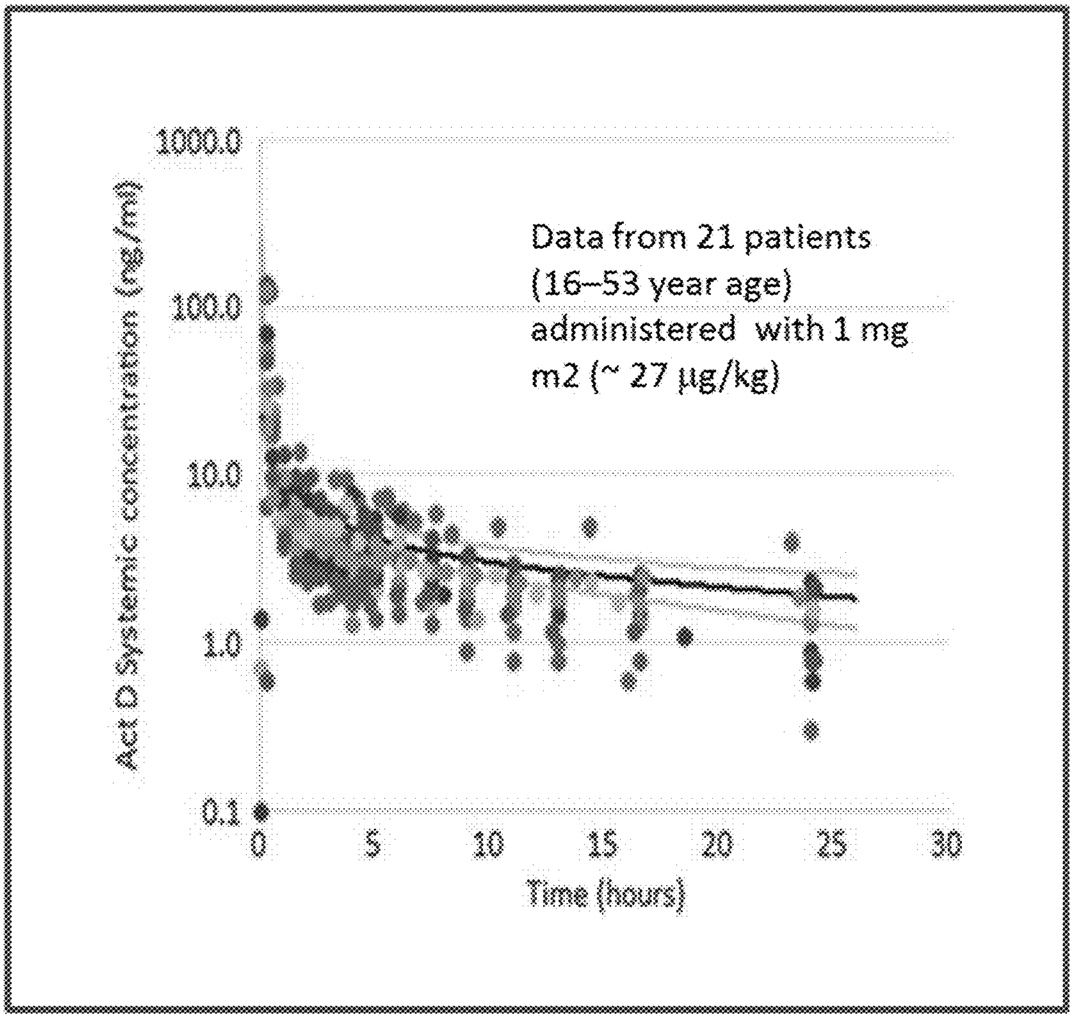

NPM1-mutated acute myeloid leukemia (AML) is a distinct leukemia entity that accounts for one third of cases of AML in adults. NPM1 is a crucial protein for normal nucleolar integrity and function. Because it contains a low level of non-mutant NPM1 (owing to haploinsufficiency and cytoplasmic retention of non-mutant NPM1 by the NPM1 mutant), the nucleolus of NPM1-mutated AML cells may be vulnerable to drugs that trigger a nucleolar stress response. The tumor suppressor p53 is often inactivated in cancer, either through downregulation of protein or loss-of-function mutations. As such, stabilization of p53 may treat those cancers carrying wild type (WT) p53. Herein, SIRT1 inhibitor Tenovin-1 and polo-like kinase 1 (Plk1) inhibitor BI2536 were used to stabilize p53. (See Chen, L et al. Cell Cycle 2016, 15(6): 840-849). Either p53-dependent or p53-independent responses to nucleolar stress have been described. Importantly, the p53-mediated nucleolar stress response is retained in NPM1-mutated AML because NPM1-mutated AML cells lack p53 mutations or deletions.

Among potentially active drugs, this disclosure focuses on dactinomycin because it induces nucleolar stress by interfering with ribosome biogenesis through inhibition of RNA polymerase I. Dactinomycin is active in Wilms' tumor and some other tumors. However, this disclosure describes the first study on dactinomycin use in AML.

This disclosure also provides methods of treating a myelodysplastic syndrome (MDS) comprising administering compositions comprising dactinomycin.

This disclosure also provides methods of treating cancer comprising administering compositions comprising dactinomycin. In certain embodiments, the cancer may be acute myeloid leukemia (AML), chronic lymphocytic leukemia (CLL), colorectal cancer, neuroendocrine cancer, esophageal cancer, or gastrointestinal stromal tumor (GIST). In certain embodiments, the cancer may be acute myeloid leukemia (AML). In certain embodiments, the AML may be NPM1-mutated AML or wild type AML. In certain embodiments, the AML may be NPM1-mutated AML.

According to methods of the disclosure, compositions of this disclosure comprising dactinomycin may be administered as a preferred, frontline therapy, for subjects having newly diagnosed and/or previously untreated cancer who are unfit for intensive chemotherapy or the elderly (i.e. subjects 60 year of age or older). Subjects who may be unfit for intensive chemotherapy include, but are not limited to, subjects who have a compromised immune system, a blood disorder, an intestinal disorder, or an infection.

In certain embodiments of the disclosure, dactinomycin compositions may be administered as a preferred, frontline therapy, for subjects having newly diagnosed and/or previously untreated AML who are unfit for intensive chemotherapy or the elderly (i.e. subjects 60 year of age or older). Subjects who may be unfit for intensive chemotherapy include, but are not limited to, subjects who have a compromised immune system, a blood disorder, an intestinal disorder, or an infection.

Acute Myeloid Leukemia (AML)

AML Acute Myeloid Leukemia (AML) is the most common name for a condition that is alternatively referred to as acute myelocytic leukemia, acute myelogenous leukemia, acute granulocytic leukemia, or acute non-lymphocytic leukemia. (See Falini, B. et al. "Cytoplasmic nucleo-phosmin in acute myelogenous leukemia with a normal karyo-type" N. Engl. J. Med. 2005; 352:254-266; Cancer Genome Atlas Research Network. "Genomic and epigenomic landscapes of adult de novo acute myeloid leukemia" N. Engl. J. Med. 2013; 368:2059-2074.)

AML initially develops in the bone marrow. However, AML cells quickly progress into the blood. Once present in the blood of a subject, the cancerous cells may spread to every part of the body, including, but not limited to, the lymph nodes, liver, spleen, central nervous system (brain and/or spinal cord), cutis and/or testicles.

As an acute form of leukemia, the cancer cells are immature blood cells with stem cell-like qualities that, under normal conditions, rapidly divide to provide a number of blood cell types. When these cells undergo an oncogenic transformation, this rapid division produces cancer cells at a faster rate than a cancer affecting a mature and/or terminally differentiated cell type.

As a myeloid form of leukemia, cancer cells transform from stem-like myeloid cells that, under normal conditions, divide to generate cells that differentiate into red blood cells, white blood cells, and the megakaryocytes that generate platelets. When these cells undergo an oncogenic transformation, immature myeloid cells divide rapidly without subsequently producing the numbers and/or proportions of red blood cells, white blood cells, and platelets that should normally populate the circulating blood. Consequently, under oncogenic conditions, myeloid cells divide and aggregate in the bones, the increased production of these cells competing for resources with and interrupting the normal function of healthy, non-cancerous, cells in the bone marrow. Moreover, under oncogenic conditions, myeloid cells produce an insufficient amount of red blood cells to carry normal levels of oxygen through the blood to one or more organs, insufficient amount of white blood cells to mount an adequate immune response to infection, and/or insufficient amount of platelets to facilitate blood clotting.

Subjects of the disclosure may present one or more risk factors for developing AML. Exemplary risk factors include, but are not limited to, personal and/or family history of cancer, increasing age, being male, prior treatment with chemotherapy and/or radiation, exposure to radiation (including survivors of nuclear reactor accidents), exposure to hazardous chemicals (including, for example, benzene), past or current smoking habit, exposure to secondhand smoke, personal history of other blood disorders (including, for example, myelodysplasia, polycythemia vera and/or thrombocythemia), genetic disorders (including, for example, Down syndrome). Although subjects of the disclosure may be any gender, subjects who are genetically male have an increased risk of developing AML compared to those subjects who are genetically female. Although subjects of the disclosure may be any age, those subjects who are at least 40, at least 50, at least 60, at least 70, at least 80, or at least 90 have a greater risk of developing AML compared to younger subjects.

Subjects of the disclosure may present one or more signs or symptoms of AML, including, but not limited to, fever, bone pain, lethargy and/or fatigue, shortness of breath, pale skin, frequent infections, easy bruising, unusual bleeding (from, for example, nose and gums, and/or diminished or insufficient blood clotting).

According to methods of the disclosure, dactinomycin may be administered as a preferred, frontline therapy, for subjects having newly diagnosed and/or previously untreated AML who are unfit for intensive chemotherapy or the elderly (i.e. subjects 60 year of age or older). Subjects who may be unfit for intensive chemotherapy include, but are not limited, to subject who have a compromised immune system, a blood disorder, an intestinal disorder, or an infection.

Subjects of the disclosure may have been treated for AML with another therapy and may have been resistant to that therapy or may not have shown any improvement as a result of that therapy. Thus, subjects of the disclosure include those individuals who have failed one or more therapies prior to treatment with dactinomycin according to the methods of the disclosure.

Treating AML can result in a partial or a complete hematological remission. A complete hematological remission is defined as a reduction of leukemic cells to <5% of bone marrow cells at morphological examination of bone marrow smears and/or sections. A partial hematological remission is defined as a reduction of leukemic cells to >5%, but less than an initial percentage of bone marrow cells, determined by a morphological examination of bone marrow smears and/or sections. The initial percentage of leukemic cells among bone marrow cells may be determined at the time of diagnosis and/or initiation of treatment. A reduction of that initial percentage may be determined at any point during or following the completion of treatment.

Moreover, treating AML can result in a decrease in size of an area or zone of cellular proliferation, and, in particular, an extramedillary leukemic mass. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating AML can result in a decrease in the number or proportion of cells having an abnormal appearance or morphology (i.e., morphological regression). Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

NPM1-Mutated Acute Myeloid Leukemia (AML)

NPM1-mutated acute myeloid leukemia (AML) is a distinct leukemia entity that accounts for one third of cases of AML in adults. NPM1 is a crucial protein for normal nucleolar integrity and function. (See Falini, B. et al. "Acute myeloid leukemia with mutated nucleophosmin (NPM1): any hope for a targeted therapy?" Blood Rev. 2011; 25:247-254.)

Chronic Lymphocytic Leukemia (CLL)

Chronic lymphocytic leukemia (CLL) is the most common type of leukemia in the elderly. It is characterized by the accumulation of CD5/CD19/CD23 positive B-lymphocytes in the blood, bone marrow, lymph nodes and spleen. The clinical course of the disease is highly variable, ranging from patients who remain asymptomatic over 10 years to others who require aggressive therapy immediately after diagnosis.

Myelodysplastic Syndrome (MDS)

As used herein, the terms "myelodysplastic syndrome (MDS)" "myelodysplastic syndromes," and/or the like refer to one or more of a group of disorders caused by poorly formed or dysfunctional blood cells in the bone marrow.

In one embodiment, myelodysplastic syndrome (MDS) are a group of diverse bone marrow disorders affecting either red blood cells, white blood cells, and platelets in bone marrow.

Progenitor stem cells that fail to mature and may accumulate in the bone marrow or have a shortened life span resulting in fewer than normal mature blood cells in the circulation MDS has an incidence of approximately 4-5 per 100,000 of the population, increasing to 20-50 per 100,000 after age 60.

MDS progresses to acute myeloid leukemia (AML) in approximately 30% of the cases.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

As used herein, the term "adverse event" or "AE" is any unfavorable and unintended sign (including an abnormal laboratory finding), symptom, or disease temporally associated with the use of a medicinal (investigational) product, which may or may not be considered related to the medical treatment or procedure. (See "Common Terminology Criteria for Adverse Events v3.0 (CTCAE)", publish date: Aug. 9, 2006.)

As used herein, the term "remission" refers to a decrease in or disappearance of signs and symptoms of cancer. In partial remission, some, but not all, signs and symptoms of cancer have disappeared. In complete remission, all signs and symptoms of cancer have disappeared, although cancer still may be in the body. In one aspect, the remission may be morphological in nature. In one aspect, the remission may be molecular in nature. In one aspect, the remission may be both morphological and molecular in nature.

As used herein, the term "cancer", refers to a disease involving abnormal cell growth with the potential to spread to other parts of the body. Non limiting examples include: haematopoietic and lymphoid malignancies (acute myeloid leukemia (AML), chronic myeloid leukemia (CML), acute lymphocytic leukemia (ALL), chronic lymphocytic leukemia (CLL)), colorectal cancer, neuroendocrine cancer, esophageal cancer (Barrett's syndrome), gastrointestinal stromal tumor (GIST), bone marrow malignancies, myelodysplastic syndromes, myeloproliferative diseases, lymph nodes and lymphatic system malignancies, Wilm's tumor, rhabdomyosarcoma, Ewing's sarcoma or any metastasis thereof.

As used herein, the term "selectively" means tending to occur at a higher frequency in one population than in another population. The compared populations can be cell populations. Preferably, dactinomycin or a dactinomycin composition of the disclosure acts selectively on a cancer or precancerous cell but not on a normal cell. Preferably, dactinomycin or a dactinomycin composition of the disclosure acts selectively to modulate one molecular target (e.g., RNA/DNA chain elongation by inhibiting ribosome biogenesis) but does not significantly modulate another molecular target (e.g., a cellular repair enzyme). Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A dactinomycin composition of the disclosure can modulate the activity of a molecular target (e.g., a ribosome). Modulating refers to stimulating or inhibiting an activity of a molecular target. Preferably, a dactinomycin composition of the disclosure modulates the activity of a molecular target if it stimulates or inhibits the activity of the molecular target by at least 2-fold relative to the activity of the molecular target under the same conditions but lacking only the presence of said compound. More preferably, a dactinomycin composition of the disclosure modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

Dactinomycin is a polypeptide antitumor antibiotic composed of two cyclic peptides attached to a phenoxazine that is derived from *Streptomyces parvullus*. Dactinomycin binds to DNA and inhibits RNA synthesis (transcription) by specifically interfering with chain elongation of mRNA transcripts. Dactinomycin binds strongly but reversibly to DNA molecules. As a result of impaired mRNA production, protein synthesis, ribosome biogenesis and cell division decline after dactinomycin therapy. Because dactinomycin inhibits cell division, it is hypothesized that dactinomycin inhibits the oncogenic cell division present with AML in the bone marrow.

Dactinomycin is currently used as a highly effective chemotherapeutic approved for rare tumor entities occurring mostly in children, such as Wilms tumor, rhabdomysarcoma, gestational trophoblastic disease, and Ewing sarcoma. (See Osathanondh, R. et al. Cancer 1975; 36:863-866; Burger K. et al. J. Biol. Chem. 2010; 285:12416-12425.) Thus, dactinomycin has a known risk profile.

Dactinomycin compositions and formulations of the disclosure could be used for the treatment of CLL high-risk patients without further delay.

Dactinomycin is extremely corrosive and may produce many adverse side effects, for example, tissue necrosis and mucositis may occur following extravasation days to weeks after administration at the infusion site. Mucositis, i.e., extremely painful blistering, inflammation, and ulceration of the mucous membranes lining the gastrointestinal tract, is an adverse effect of chemotherapy and radiotherapy treatment for cancer and/or MDS.

Mucositis may be so adverse and debilitating to the degree that subjects being treated with dactinomycin are not able to continue and complete their treatment. Mucositis which occurs in the mouth, i.e., oral mucositis, is a common and often debilitating complication of cancer and/or MDS treatment, e.g., treatment with dactinomycin.

Mucositis that is adverse of debilitating to the degree that subjects being treated with dactinomycin may not able to continue and complete their treatment is a problem in cancer treatment because, in many instances, a subject who discontinues or fails to complete dactinomycin treatment may experience a relapse of the cancer.

Development of mucositis may be dose-dependent and may be mitigated by administering dactinomycin doses in the range of 10 to 20 μg/kg/day in a controlled release manner per any of the dactinomycin nanoparticle compositions of the application, while still maintaining efficacy for treatment of MDS and/or cancers, such as, e.g., AML. In one embodiment, development of mucositis can be mitigated by concurrent treatment with anti-inflammatory agents, antioxidants, and/or growth and differentiation promoters.

Mucositis can also be mitigated by pre-treatment with anti-inflammatory agents, e.g. pentoxifylline, NSAIDs, antioxidants, e.g., vitamin C and retinoic acid (e.g., all trans-retinoic acid), and growth and differentiation promoters, e.g., glutamine.

Mucositis can also be mitigated by employing dosing regimens having "drug holidays" between dosing periods. The drug holiday period may be one, two, three, or four weeks.

In one embodiment, the dosing period of any of the dactinomycin nanoparticle compositions of the application is once or twice over a period of 1, 2, or 3 weeks In one embodiment, a representative dosing cycle comprises a mucositis pretreatment with an anti-inflammatory agent, followed by treatment with any of the nanoparticle compositions of the application once or twice over a period of days or 1, 2, or 3 weeks, followed by a drug holiday of one week, two weeks, three weeks, four weeks, five weeks, or six weeks, followed by treatment with any of the nanoparticle compositions of the application once or twice over a period of 1, 2, or 3 weeks.

Dactinomycin may also be referred to as 2-amino-N,N'-bis(hexadecahydro-2,5,9-trimethyl-6,13-bis(1-methylethyl)-1,4,7,11,14-pentaoxo-1H-pyrrolo(2,1-I)(1,4,7,10,13) oxatetra-azacyclohexadecin-10-yl)-4,6-dimethyl-3-oxo-3H-phenoxazine-1,9-dicarboxamide, ActD, actinomycin C1, actinomycin D; actinomycin iv, dactinomicina, dactomycin, dactinomycine, dactinomycinum, or meractinomycin. Dactinomycin belongs to the class of organic compounds known as cyclic depsipeptides. Cyclic depsipeptides include natural and/or non-natural (i.e., synthetic) compounds having sequences of amino and hydroxy carboxylic acid residues (usually α-amino and α-hydroxy acids) connected in a ring. Amino and hydroxy carboxylic acid residues within dactinomycin may alternate in a repeating pattern.

Pharmaceutical Compositions

The present disclosure provides compositions comprising a therapeutically effective amount of dactinomycin encapsulated in nanoparticles comprising one or more polymers. The polymers include, without limitation, poly(lactic acid) (PLA), poly(butyric acid), poly(valeric acid), poly(caprolactone) (PCL), poly(hydroxybutyrate), poly(lactide-co-caprolactone), poly(lactide-co-glycolide) (PLGA), polymethylcyanoacrylate, and polyanhydrides, poly(ortho)esters, or polyurethanes thereof, wherein the polymer optionally further comprises polyethylene glycol (PEG) or polyethylene glycol methyl ether (mPEG) and/or any combination thereof.

The present disclosure provides compositions comprising blends, i.e. mixtures of one more or polymers selected from poly(lactic acid) (PLA), poly(butyric acid), poly(valeric acid), poly(caprolactone) (PCL), poly(hydroxybutyrate), poly(lactide-co-caprolactone), poly(lactide-co-glycolide) (PLGA), polymethylcyanoacrylate, and polyanhydrides, poly(ortho)esters, or polyurethanes thereof.

The present disclosure also provides compositions comprising blends, i.e. mixtures of one more or polymers selected from poly(lactic acid) (PLA), poly(butyric acid), poly(valeric acid), poly(caprolactone) (PCL), poly(hydroxybutyrate), poly(lactide-co-caprolactone), poly(lactide-co-glycolide) (PLGA), polymethylcyanoacrylate, and polyanhydrides, poly(ortho)esters, or polyurethanes thereof, wherein the polymer further comprises polyethylene glycol (PEG), polyethylene glycol methyl ether (mPEG), and/or a combination thereof.

Those skilled in the art will recognize the that release characteristics and/or kinetics can be altered (e.g., increased or decreased) by selecting various combinations of these polymers. Determination of the appropriate polymer combinations to achieve the desired release rates is within the routine level of skill in the art.

A nanoparticle, as used herein, refers to a particle between about 1 and about 500 nanometers (nm) in size. For example, in one embodiment, between about 100 nm and about 200 nm.

In one embodiment, compositions of the disclosure include those compositions which comprise dactinomycin which is encapsulated in and/or associated with nanoparticles.

The present disclosure provides compositions comprising a therapeutically effective amount of dactinomycin encapsulated in nanoparticles comprising poly lactic acid (PLA) polymers. PLA is an amorphous (non-crystalline) biodegradable polymer that is typically a mixture of D and L enantiomeric forms of lactic acid. PLA is also available as crystalline polymer when synthesized using only a single enantiomer of lactic acid.

In one embodiment, the present disclosure provides for dactinomycin encapsulated in nanoparticles comprising PLA, where the PLA has a molecular weight ranging from about 10,000 to about 24,000 Da, and allows for a controlled release of dactinomycin.

In one embodiment, the molecular weight of the PLA is about 10,000 Da to about 18,000 Da.

In one embodiment, the molecular weight of the PLA is about 18,000 Da to about 24,000 Da.

In one embodiment, the molecular weight of the PLA is about 10,000 Da to about 14,000 Da, 11,000 Da to about 15,000 Da, 12,000 Da to about 16,000 Da, 13,000 Da to about 17,000 Da, 14,000 Da to about 18,000 Da, 15,000 Da to about 19,000 Da, 16,000 Da to about 20,000 Da, 17,000 Da to about 21,000 Da, 18,000 Da to about 22,000 Da, 19,000 Da to about 23,000 Da, or 20,000 Da to about 24,000 Da, In one embodiment, the molecular weight of the PLA is about 10,000 Da, about 11,000 Da, about 12,000 Da, about 13,000 Da, about 14,000 Da, about 15,000 Da, about 16,000 Da, about 17,000 Da, about 18,000 Da, about 19,000 Da, about 20,000 Da, about 21,000 Da, about 22,000 Da, about 23,000 Da, about 24,000 Da.

The present disclosure provides compositions comprising a therapeutically effective amount of dactinomycin encapsulated in nanoparticles comprising PLA, where the PLA is ester-terminated.

The present disclosure provides compositions comprising a therapeutically effective amount of dactinomycin encapsulated in nanoparticles comprising PLA, where the PLA is acid-terminated form. Ester-terminated forms of PLA are more hydrophobic than acid-terminated forms of PLA, which are in turn more hydrophilic.

In one embodiment, compositions comprising a therapeutically effective amount of dactinomycin encapsulated in nanoparticles comprising ester-terminated PLAs degrade slower than dactinomycin encapsulated in nanoparticles comprising acid-terminated PLAs and would provide for a slower release of dactinomycin from nanoparticles.

The present disclosure provides compositions comprising a therapeutically effective amount of dactinomycin encapsulated in nanoparticles comprising poly (lactide-co-glycolide (PLGA) polymers:

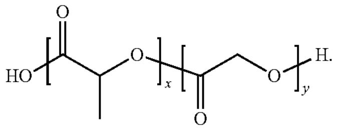

PLGA: x = number of units of lactic acid; y = number of units of glycolic acid

In aqueous environment, PLGA biodegrades by hydrolysis of its ester linkages.

The methyl side groups in PLA makes the polymer more hydrophobic than PGA. In one embodiment, lactide-rich PLGA copolymers are less hydrophilic, absorb less water and degrade more slowly compared to less lactide rich copolymers.

In one embodiment, higher molecular weight PLGAs degrade more slowly than lower molecular weight PLGAs.

In one embodiment, the present disclosure provides for dactinomycin encapsulated in nanoparticles comprising PLGA, where the PLGA has a molecular weight ranging from about 7,000 to about 54,000 Da, and allows for a controlled release of dactinomycin.

In one embodiment, the molecular weight of the PLGA is about 7,000 Da to about 17,000 Da, 17,000 Da to about 27,000 Da, 27,000 Da to about 37,000 Da, 37,000 Da to about 47,000 Da, or 47,000 Da to about 54,000 Da.

In one embodiment, the molecular weight of the PLGA is about 12,000 Da to about 22,000 Da, 22,000 Da to about 32,000 Da, 32,000 Da to about 42,000 Da, 42,000 Da to about 52,000 Da, or 44,000 Da to about 54,000 Da.

In one embodiment, the molecular weight of the PLGA is about 7,000 Da, about 8,000 Da, about 9,000 Da, about 10,000 Da, about 11,000 Da, about 12,000 Da, about 13,000 Da, about 14,000 Da, about 15,000 Da, about 16,000 Da, about 17,000 Da, about 18,000 Da, about 19,000 Da, about 20,000 Da, about 21,000 Da, about 22,000 Da, about 23,000 Da, about 24,000 Da, about 25,000 Da, about 26,000 Da, about 27,000 Da, about 28,000 Da, about 29,000 Da, about 30,000 Da, about 31,000 Da, about 32,000 Da, about 33,000 Da, about 34,000 Da, about 35,000 Da, about 36,000 Da, about 37,000 Da, about 38,000 Da, about 39,000 Da, about 40,000 Da, about 41,000 Da, about 42,000 Da, about 43,000 Da, about 44,000 Da, about 45,000 Da, about 46,000 Da, about 47,000 Da, about 48,000 Da, about 49,000 Da, about 50,000 Da, about 51,000 Da, about 52,000 Da, about 53,000 Da, or about 54,000 Da.

In one embodiment, the present disclosure provides for dactinomycin encapsulated in nanoparticles comprising PLGA, where the PLGA has a lactic acid:glycolic acid molar ratio of about 95:5, about 90:10, about 85:15, about 80:20, about. 75:25, about 70:30, about 65:35, about 60:40, about 55:45, about 50:50, about 45:55, about 40:60, about 35:65, about 30:70, about 25:75, about 20:80, about 15:85, about 10:90, or about 5:95.

In one embodiment, the present disclosure provides for dactinomycin encapsulated in nanoparticles comprising PLGA, where the PLGA has a lactic acid:glycolic acid molar ratio of about 50:50.

The present disclosure provides compositions comprising a therapeutically effective amount of dactinomycin encapsulated in nanoparticles comprising poly lactic acid (PLA) polymers, where the PLA polymers can be synthesized with polyethylene glycol (PEG) or polyethylene glycol methyl ether (mPEG) to prepare di-block copolymers (PLA-PEG and PLA-mPEG) and allow for a controlled release of dactinomycin.

In one embodiment, PLA-mPEG copolymer can be prepared according to the following scheme:

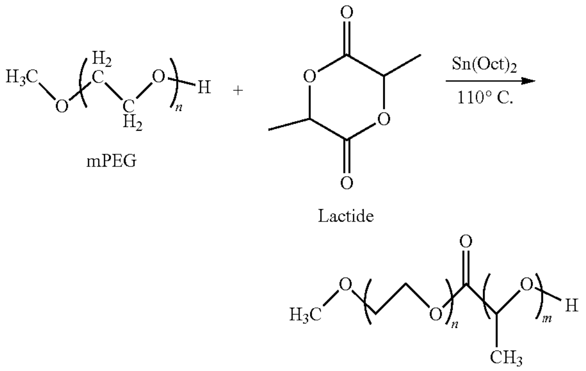

mPEG-PLA-OH

Hydrophilic PEG (and mPEG) moieties orient towards the surface of the nanoparticles and act as a barrier reducing interaction with foreign molecules by steric and hydrated repulsion. These compositions may have a longer half-life in systemic circulation compared to unmodified, nanoparticles, i.e., "non-PEG-ylated," or "non-mPEG-ylated" nanoparticles.

In one embodiment, drug release from PLA-PEG and PLA-mPEG nanoparticles occurs through diffusion. In one embodiment, drug release PLA-PEG and PLA-mPEG nanoparticles occurs through polymer degradation. In one embodiment, drug release PLA-PEG and PLA-mPEG nanoparticles occurs through diffusion and polymer degradation.

The ratio of PEG or mPEG to PLGA may influence clearance of the nanoparticles from systemic circulation.

In one embodiment, the weight percent of PEG or mPEG in the PLA-PEG or PLA-mPEG di-block copolymers is about 1% by weight, about 2% by weight, about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, about 15% by weight, about 16% by weight, about 17% by weight, about 18% by weight, about 19% by weight, about 20% by weight, about 21% by weight, about 22% by weight, about 23% by weight, about 24% by weight, about 25% by weight, about 26% by weight, about 27% by weight, about 28% by weight, about 29% by weight, about 30% by weight, about 31% by weight, about 32% by weight, about 33% by weight, about 34% by weight, about 35% by weight, about 36% by weight, about 37% by weight, about 38% by weight, about 39% by weight, about 40% by weight, about 41% by weight, about 42% by weight, about 43% by weight, about 44% by weight, about 45% by weight, about 46% by weight, about 47% by weight, about 48% by weight, about 49% by weight, about 50% by weight, about 51% by weight, about 52% by weight, about 53% by weight, about 54% by weight, about 55% by weight, about 56% by weight, about 57% by weight, about 58% by weight, about 59% by weight, about 60% by weight, about 61% by weight, about 62% by weight, about 63% by weight, about 64% by weight, about 65% by weight, about 66% by weight, about 67% by weight, about 68% by weight, about 69% by weight, about 70% by weight, about 71% by weight, about 72% by weight, about 73% by weight, about 74% by weight, about 75% by weight, about 76% by weight, about 77% by weight, about 78% by weight, about 79% by weight, about 80% by weight, about 81% by weight, about 82% by weight, about 83% by weight, about 84% by weight, about 85% by weight, about 86% by weight, about 87% by weight, about 88% by weight, about 89% by weight, about 90% by weight, about 91% by weight, about 92% by weight, about 93% by weight, about 94% by weight, about 95% by weight, about 96% by weight, about 97% by weight, about 98% by weight, or about 99% by weight.

In one embodiment, the weight percent of PEG or mPEG in the PLA-PEG or PLA-mPEG di-block copolymers is about 1% to 99%, 2% to 95%, 3% to 90%, 4% to 75%, 5% to 50%, 10% to 45%, 15% to 40%, 18% to 35%, or 20 to 30% by weight.

In one embodiment, the weight percent of PEG or mPEG in the PLA-PEG or PLA-mPEG di-block copolymers is about 25% by weight.

In one embodiment, the weight percent of mPEG in the PLA-mPEG di-block copolymer is about 25% by weight.

The present disclosure provides compositions comprising a therapeutically effective amount of dactinomycin encapsulated in nanoparticles comprising poly (lactide-co-glycolide (PLGA) polymers, where the PLGA polymers can be synthesized with polyethylene glycol (PEG) or polyethylene glycol methyl ether (mPEG) to prepare di-block copolymers (PLGA-PEG and PLGA-mPEG) and allow for a controlled release of dactinomycin. In one embodiment, PLGA-mPEG copolymer has the general structure illustrated in the scheme below:

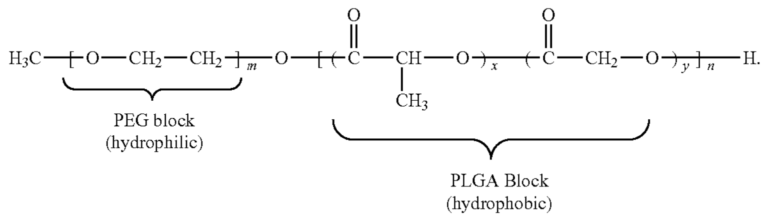

Hydrophilic PEG (and mPEG) moieties orient towards the surface of the nanoparticles and act as a barrier reducing interaction with foreign molecules by steric and hydrated repulsion. These compositions may have a longer half-life in systemic circulation compared to unmodified, nanoparticles, i.e., "non-PEG-ylated," or "non-mPEG-ylated" nanoparticles.

In one embodiment, drug release from PLGA-PEG and PLGA-mPEG nanoparticles occurs through diffusion. In one embodiment, drug release PLGA-PEG and PLGA-mPEG nanoparticles occurs through polymer degradation. In one embodiment, drug release PLGA-PEG and PLGA-mPEG nanoparticles occurs through diffusion and polymer degradation.

The ratio of PEG or mPEG to PLGA may influence clearance of the nanoparticles from systemic circulation.

In one embodiment, the weight percent of PEG or mPEG in the PLGA-PEG or PLGA-mPEG di-block copolymers is about 1% by weight, about 2% by weight, about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, about 15% by weight, about 16% by weight, about 17% by weight, about 18% by weight, about 19% by weight, about 20% by weight, about 21% by weight, about 22% by weight, about 23% by weight, about 24% by weight, about 25% by weight, about 26% by weight, about 27% by weight, about 28% by weight, about 29% by weight, about 30% by weight, about 31% by weight, about 32% by weight, about 33% by weight, about 34% by weight, about 35% by weight, about 36% by weight, about 37% by weight, about 38% by weight, about 39% by weight, about 40% by weight, about 41% by weight, about 42% by weight, about 43% by weight, about 44% by weight, about 45% by weight, about 46% by weight, about 47% by weight, about 48% by weight, about 49% by weight, about 50% by weight, about 51% by weight, about 52% by weight, about 53% by weight, about 54% by weight, about 55% by weight, about 56% by weight, about 57% by weight, about 58% by weight, about 59% by weight, about 60% by weight, about 61% by weight, about 62% by weight, about 63% by weight, about 64% by weight, about 65% by weight, about 66% by weight, about 67% by weight, about 68% by weight, about 69% by weight, about 70% by weight, about 71% by weight, about 72% by weight, about 73% by weight, about 74% by weight, about 75% by weight, about 76% by weight, about 77% by weight, about 78% by weight, about 79% by weight, about 80% by weight, about 81% by weight, about 82% by weight, about 83% by weight, about 84% by weight, about 85% by weight, about 86% by weight, about 87% by weight, about 88% by weight, about 89% by weight, about 90% by weight, about 91% by weight, about 92% by weight, about 93% by weight, about 94% by weight, about 95% by weight, about 96% by weight, about 97% by weight, about 98% by weight, or about 99% by weight.

In one embodiment, the weight percent of PEG or mPEG in the PLGA-PEG or PLGA-mPEG di-block copolymers is about 1% to 99%, 2% to 95%, 3% to 90%, 4% to 75%, 5% to 50%, 10% to 47%, 15% to 45%, 20% to 42%, or 25 to 45% by weight.

In one embodiment, the weight percent of PEG or mPEG in the PLGA-PEG or PLGA-mPEG di-block copolymers is about 35% by weight.

In one embodiment, the weight percent of mPEG in the PLGA-mPEG di-block copolymer is about 35% by weight.

The present disclosure also provides any of the compositions disclosed herein which comprise a therapeutically effective amount of dactinomycin encapsulated in nanoparticles comprising one or more polymers, where the nanoparticles have an average size of about 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, 120 nm, 121 nm, 122 nm, 123 nm, 124 nm, 125 nm, 126 nm, 127 nm, 128 nm, 129 nm, 130 nm, 131 nm, 132 nm, 133 nm, 134 nm, 135 nm, 136 nm, 137 nm, 138 nm, 139 nm, 140 nm, 141 nm, 142 nm, 143 nm, 144 nm, 145 nm, 146 nm, 147 nm, 148 nm, 149 nm, 150 nm, 151 nm, 152 nm, 153 nm, 154 nm, 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, or 200 nm.

The present disclosure also provides any of the compositions disclosed herein which comprise a therapeutically effective amount of dactinomycin encapsulated in nanoparticles comprising one or more polymers, where the nanoparticles have an average size of about 100 nm to about 110 nm, about 105 nm to about 115 nm, about 110 nm to about 120 nm, about 115 nm to about 125 nm, about 120 nm to about 130 nm, about 125 nm to about 135 nm, about 130 nm to about 140 nm, about 135 nm to about 145 nm, about 130 nm to about 140 nm, about 135 nm to about 145 nm, about 140 nm to about 150 nm, about 145 nm to about 155 nm, about 150 nm to about 160 nm, about 155 nm to about 165 nm, about 160 nm to about 170 nm, about 165 nm to about 175 nm, about 170 nm to about 180 nm, about 175 nm to about 185 nm, about 180 nm to about 190 nm, about 185 nm to about 195 nm, or about 190 nm to about 200 nm.

In one embodiment, nanoparticle size may be determined using methods known in the art, for example, using a Malvern Nano-ZS zeta sizer.

The present disclosure also provides any of the compositions disclosed herein which comprise a therapeutically effective amount of dactinomycin encapsulated in nanoparticles comprising one or more polymers, where the composition further comprises a surfactant.

In one embodiment, the surfactant comprises about 0.01% to about 10.0% by weight of each nanoparticle. In one embodiment, the surfactant comprises about 0.1% to about 5.0% by weight of each nanoparticle. For example, the surfactant comprises about 0.2% to about 4.0% by weight of each nanoparticle, about 0.5% to about 3.0% by weight of each nanoparticle, about 1.0% to about 2.5% by weight of each nanoparticle.

In one embodiment, the surfactant comprises about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 14.7%, about 4.8%, about 4.9%, or about 5.0% by weight of each nanoparticle.

In one embodiment, the surfactant comprises less than 2.0% by weight of each nanoparticle.

The present disclosure also provides any of the compositions disclosed herein which comprise a therapeutically effective amount of dactinomycin encapsulated in nanoparticles comprising one or more polymers, wherein the composition further comprises a surfactant, wherein the surfactant is polyvinyl alcohol, Tween® 20, Tween® 80, vitamin E TPGS, sodium cholate, bile salts (e.g., sodium taurodexoycholate), polyethylene glycol, (e.g., PEG 600, PEG, PEG 4500, Brij® (e.g., 20, 35, 58, and the like), and/or poloxamers (e.g., polaxamer 188, polaxmer 407. In one embodiment, the surfactant is polyvinyl alcohol. In one embodiment, the surfactant is polyvinyl alcohol where the polyvinyl alcohol is 80% hydrolyzed and has a molecular weight of about 9,000 to about 10,000 Da.

The present disclosure also provides any of the compositions disclosed herein which comprise a therapeutically effective amount of dactinomycin encapsulated in nanoparticles comprising one or more polymers, wherein the composition further comprises about 1% by weight to about 50% by weight dactinomycin.

The present disclosure also provides any of the compositions disclosed herein which comprise a therapeutically effective amount of dactinomycin encapsulated in nanoparticles comprising one or more polymers, wherein the composition further comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%2, 24%, 25%, 26%2, 27%, 28%, 29%, 30%, 31%, 32%, 33%, 34%, 35%, 36%, 37%, 38%, 39% 40%, 41%, 42%, 43%, 44%, 45%, 46%, 47%, 48%, 49%, or 50% by weight dactinomycin.

The present disclosure also provides any of the compositions disclosed herein which comprise a therapeutically effective amount of dactinomycin encapsulated in nanoparticles comprising one or more polymers, wherein the composition further comprises about 5% by weight to about 15% by weight dactinomycin.

The present disclosure also provides compositions comprising a therapeutically effective amount of dactinomycin encapsulated in nanoparticles comprising phospholipids, which function as a liquid surfactant which enables the formation of liquid crystals, further comprising purified water, a buffering agent (e.g., glycine), an oil component (e.g., D,L-alpha-tocopherol, and a surfactant (e.g., sodium deoxycholate or polyvinyl alcohol). Examples of phospholipids for these compositions include, without limitation, phosphatidylcholine with negatively charged phospholipids (Phospholipon® 80), lecithin fraction enriched with phosphatidylcholine (Phospholipon® 85G), and phosphatidylcholine stabilized with 0.1% ascorbyl palmitate (Phospholipon® 90G). (See, e.g., U.S. Pat. No. 7,713,440; Particle Sciences Technical Brief, 2012, Vol. 4; and Anderson, D. et al. CRC Concise Encyclopedia of Nanotechnology, Taylor & Francis Group, LLC, 2016, 5 pages, all of which are incorporated herein by reference in their entireties).

In one embodiment, a composition comprising a therapeutically effective amount of dactinomycin encapsulated in nanoparticles comprising phospholipids may be prepared by using any methods know in the art. For example, mixing a blank phospholipid composition (e.g., 25 mL of a phosolipid composition comprising Phospholipon® 90G, purified water, glycine, D,L-alpha-tocopherol, sodium decarboyxlate) with dactinomycin (e.g., 375 mg) by vigorous stirring for several hours (e.g., 5 hours), followed by filtration using a 0.45 um CA (cellulose acetate) filter.

The present disclosure provides compositions comprising dactinomycin encapsulated in nanoparticles in combination with at least one pharmaceutically acceptable excipient or carrier.

As used herein, the terms "encapsulation," "encapsulated," and the like mean that the dactinomycin and/or other drug or agent are encapsulated within the nanoparticles (e.g., fully or partially), associated with the nanoparticles, and/or adsorped on or onto the nanoparticles.

A "composition" is any formulation containing a dactinomycin nanoparticle composition as described herein in a form suitable for administration to a subject. In one embodiment, the composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. Although compositions of the disclosure may be administered by any route, preferred routes of administration include intravenous injection or infusion. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The present disclosure also provides compositions disclosed herein which comprise a therapeutically effective amount of dactinomycin encapsulated in nanoparticles comprising one or more polymers, further comprising one or more other chemotherapeutic drugs in addition to dactinomycin. The other chemotherapeutic drugs can be encapsulated in the nanoparticle along with dactinomycin, and/or not encapsulated in the same nanoparticle as dactinomycin.

In one embodiment, the other chemotherapeutic drug includes, without limitation, topoisomerase inhibitors, (e.g., etoposide, irinotecan, topotecan, camptothecin, lamerallarin D, teniposide, mitoxantrone, amsacrine, ellipticines, aurintricaboxylic acid, HU-331), platinum-based therapies (e.g., cisplatin, carboplatin, oxaliplatin, nedaplatin, triplatin tetranitrate, picoplatin, satraplatin), anthracycline antibiotics (e.g., daunorubicin, doxorubicin, epirubicin, idarubicin), taxanes (e.g., paclitaxel, docetaxel, baccatin III, 10-deacetylbaccatin), tyrosine kinase inhibitors (e.g., imatinib, enzastaurin, dasatinib, erlotinib, gefitinib, lapatinib, nilotinib, sorafenib, sunitinib, everolimus, sirolimus, temsirolimus), nucleoside analogs (e.g., cytarabine, gemcitabine, capecitabine), FLT3 inhibitors (e.g., Rydapt® (midostaurin), sorafenib, lestaurtinib, quizartinib, ponatinib, crenolanib, and gliteritinib), and hyper methylation inhibitors (e.g., azacitidine, decitabine, and zebularine).

The term "antioxidant", as used herein, includes, without limitation, vitamin C, retinoic acid (e.g., all trans-retinoic acid), amifostine, and N-acetyl cysteine.

The term "anti-inflammatory agent", as used herein, includes, without limitation, pentoxifylline and nonsteroidal anti-inflammatory drugs (NSAIDs), e.g., ibuprofen.

The term "growth and differentiation promoters", includes, without limitation, glutamine.

A dactinomycin composition encapsulated in nanoparticles of the disclosure is formulated to be compatible with its intended route of administration. Examples of routes of administration include intravenous administration. Solutions or suspensions used for intravenous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A dactinomycin composition encapsulated in nanoparticles of the disclosure can be administered to a subject in need thereof by one or more routes commonly used for chemotherapeutic treatments. For example, a dactinomycin composition encapsulated in nanoparticles of the disclosure may be injected or infused into the blood stream of a subject (e.g. administered intravenously). The dose chosen should be sufficient to constitute effective treatment but not as high as to cause unacceptable side effects (e.g., mucositis). The state of the disease condition (e.g., cancer, precancer, and the like) and the health of the patient should preferably be closely monitored during and for a reasonable period after treatment.

The term "therapeutically effective amount", as used herein, refers to an amount of a dactinomycin composition encapsulated in nanoparticles to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one aspect, the disease or condition to be treated is MDS. In a one aspect, the disease or condition to be treated is cancer. In another aspect, the disease or condition to be treated is AML.

The term "drug holiday", as used herein, refers to an amount of time in between administrations of any of the dactinomycin composition encapsulated in nanoparticles of the disclosure for the treatment of MDS and/or cancer. In one aspect, the drug holiday is 1 week, 2 weeks, 3 weeks, 4 weeks, or any amount of time in between. For example, the cancer to be treated is AML.

For any composition of the disclosure, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting compositions may be administered every 3 to 4 days, every week, or once every two weeks depending on half-life and clearance rate of the particular formulation.

The dactinomycin composition encapsulated in nanoparticles of the disclosure may be manufactured by conventional means, e.g., in a manner as disclosed in McCall, R. L. et al. J. Vis. Exp. (82), e51015.

Any of the dactinomycin compositions encapsulated in nanoparticles disclosed herein can be prepared according to the following general procedure:

A. A stock solution of dactinomycin (25 mg/mL) is prepared in an organic solvent.
B. A stock solution of the polymer (e.g. 25 mg/mL when using PLA polymers such as Resomer® R 202S and R 203H, or a 50 mg/mL when using Resomer® D5050 DLG mPEG 5000 (35 wt %, PEG) and 100 DL mPEG 5000 (25 wt %, PEG)) is prepared in an organic solvent.
C. The dactinomycin solution is added into polymer solution until the amount of the polymer to API reaches 10:1 ratio (w/w).
D. The final solution is vortexed until homogeneous.
E. A surfactant solution in water (a water phase) is prepared.
F. Formation of a dactinomycin nanoparticle emulsion is accomplished by adding the polymer/dactinomycin solution into small amount of water phase while the water phase is on high vortex until the entire polymer solution is added to reach an organic:water phase ratio of about 1:7 by volume.
G. Continued vortexing followed by transferring the mixture to an ultrasonicator at about 0° C. and sonication for several minutes until desired nanoparticle size is achieved (e.g., about 100 nm to about 200 nm).
H. Pouring into stirring bulk water phase of surfactant in solution and vigorous stirring at room temperature until complete evaporation of the organic solvent is completed.

The encapsulation efficiency of this procedure is about 1-50%, e.g., 30%, For example, if the procedure is performed using 100 mg of free dactinomycin, about 1-50 mg (e.g., about 30 mg) of the dactinomycin will be encapsulated in nanoparticles.

In one embodiment, any of the dactinomycin compositions encapsulated in nanoparticles disclosed herein can be purified by centrifuging hardened or cured nanoparticles, removing the supernatant, washing the dactinomycin nanoparticles with $ddH_2O$, followed by further centrifuging for several minutes to provide a pellet.

In one embodiment, any of the dactinomycin compositions encapsulated in nanoparticles disclosed herein can be purified to remove free dactinomycin by centrifuging hardened or cured nanoparticles, removing the supernatant, washing the dactinomycin nanoparticles with $ddH_2O$, followed by further centrifuging for several minutes to provide a pellet.

In one embodiment, any of the dactinomycin compositions encapsulated in nanoparticles disclosed herein can be purified to remove 95%, 96%, 97%, 98%, 99%, or more of the free (non-encapsulated) dactinomycin remaining in the composition. Thus, in any of the compositions or formulations described herein, the amount of free dactinomycin is less than about 5% (i.e., less than 5%, less than 4%, less than 3%, less than 2%, less than 1%, less than 0.5%, less than 0.1%) by weight of the amount of dactinomycin encapsulated in nanoparticles. In one embodiment, larger nanoparticle removal from any of the dactinomycin compositions encapsulated in nanoparticles disclosed herein is accomplished by resuspending the pellet in $ddH_2O$ and centrifuging for several minutes, followed by collecting the supernatant and then concentrating using a centrifugal filter, and centrifuging for several additional minutes at 14,000× rpm to remove free dactinomycin.

In one embodiment, the dactinomycin compositions encapsulated in nanoparticles prepared in this manner can be used directly.

In one embodiment, any of the dactinomycin compositions encapsulated in nanoparticles disclosed herein may be stored at 4° C. for up to several weeks.

In one embodiment, the dactinomycin compositions encapsulated in nanoparticles disclosed herein may be lyo- and cryo-protected with sucrose (10-30%) prior to storage and lyophilized prior to use. Any other suitable cryo-preservation agent known in the art may also be used.

Drug loading dactinomycin compositions encapsulated in nanoparticles disclosed herein was tested using HPLC.

Further guidance on the preparation of ActD nanoparticle formulation can be found in the Examples section as well as in McCall, R. L. et al. J. Vis. Exp. (82), e51015, which is incorporated by reference in its entirety.

The dactinomycin compositions encapsulated in nanoparticles of the disclosure may be manufactured on a larger scale. To facilitate this process, a high pressure homogenizer may be used instead of ultrasonification to make the nanoparticles. Further, tangential flow filtration/diafiltration may be used to remove free dactinomycin and concentrate the nanoparticles instead of centrifugation. Also, the addition of lyoprotectant excipients, e.g., sucrose, trehalose, mannitol, and the like may be added to the nanoparticles upon storage, and then lyophilized before use.

Compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the dactinomycin nanoparticle compositions in the required amount in an appropriate solvent with one or a combination of ingredients enumerated above, as required, followed by filtered sterilization. Generally, dispersions are prepared by incorporating the active dactinomycin compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

The active compounds, e.g., dactinomycin and dactinomycin encapsulated in nanoparticles, can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation, Evonik, and Nova Pharmaceuticals, Inc., among others.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the dactinomycin nanoparticle compositions used in accordance with the disclosure vary depending on the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the MDS and/or cancer. Dosages can range from about 1 μg/kg per day to about 30 μg/kg per day in a single, a divided, or a continuous dose (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The compositions can be included in a container, pack, or dispenser together with instructions for administration.

Dactinomycin may be capable of forming salts. All of these salt forms are also contemplated within the scope of the disclosure.

As used herein, "pharmaceutically acceptable salts" refer to derivatives of the compounds of the disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, meglumine, and the like.

It should be understood that all references to pharmaceutically acceptable salts include solvent addition forms (solvates) or crystal forms (polymorphs) as defined herein, of the same salt.

Dactinomycin may also be prepared as an ester, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

Dactinomycin may also be prepared as prodrugs, for example, pharmaceutically acceptable prodrugs. The terms "pro-drug" and "prodrug" are used interchangeably herein and refer to any compound which releases an active parent drug in vivo. Prodrugs enhance numerous desirable qualities of pharmaceuticals (e.g., solubility, bioavailability, manufacturing, etc.). Accordingly, the compounds of the disclosure may be delivered in prodrug form. Thus, the disclosure is intended to cover prodrugs of the presently claimed compounds, methods of delivering the same and compositions containing the same. "Prodrugs" are intended to include any covalently bonded carriers that release an active parent drug of the disclosure in vivo when such prodrug is administered to a subject. Prodrugs in the disclosure are prepared by modifying functional groups present in the compound in such a way that the modifications are cleaved, either in routine manipulation or in vivo, to the parent compound. Prodrugs include compounds of the disclosure wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the disclosure, and the like, See Bundegaard, H., *Design of Prodrugs, p* 1-92, Elsevier, New York-Oxford (1985).

Compositions of the disclosure may be administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

Compositions of the disclosure formulated for oral administration include compositions which comprise granulated materials using traditional pharmaceutical methods or adsorbed onto pharmaceutically acceptable excipients, e.g. microcrystalline cellulose, mannitol, sorbitol, starch, ion exchange resins, etc., and compressed into a tablet or loaded into a capsule. The tablet or capsule may optionally be enteric coated to target delivery to the small intestine or colon.

Nanoparticle formulations of dactinomycin disclosed in the application may improve the oral bioavailability of dactinomycin via particle uptake pathway across the intestinal mucosa.

The nanoparticle compositions of the application may also be incorporated into a controlled release tablet or matrix to further regulate release of dactinomycin while maintaining efficacy The nanoparticle compositions of the application may alternately be formulated as a pellet or bead manufactured using extrusion-spheronization or drug-layered onto nonpareils using fluid bed Wurster coating. The beads may be coated with controlled release or enteric polymers to further regulate drug release.

Dactinomycin beads may be combined with beads of other chemotherapeutic drugs in defined ratios and loaded into capsules to provide efficacious dosing.

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

The dosage regimen can be daily administration (e.g. every 24 hours) of a compound of the disclosure. The dosage regimen can be daily administration for consecutive days, for example, at least two, at least three, at least four, at least five, at least six or at least seven consecutive days. Dosing can be more than one time daily, for example, twice, three times or four times daily (per a 24 hour period). The dosing regimen can be a daily administration followed by at least one day, at least two days, at least three days, at least four days, at least five days, or at least six days, without administration. For example, a compound of the disclosure is administered at least once in a 24 hour period, then a compound of the disclosure is not administered for at least six days, then a compound of the disclosure is administered to a subject in need.

Techniques for formulation and administration of the disclosed compounds of the disclosure can be found in *Remington: the Science and Practice of Pharmacy,* 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such compositions in amounts sufficient to provide the desired dosage amount in the range described herein.

Combination Therapies

Dactinomycin compositions of the disclosure may be administered with one or more other chemotherapeutics, e.g., a topoisomerase inhibitor, a platinum-based therapy, an anthracycline antibiotic, a taxane, a tyrosine kinase inhibitor, and a nucleoside analog, a FLT3 inhibitor, or a hyper methylation inhibitor.

In one aspect, the dactinomycin nanoparticle and the other chemotherapeutic may be administered simultaneously.

In one aspect, the dactinomycin and the other chemotherapeutic may be administered simultaneously, with both the dactinomycin and the other chemotherapeutic encapsulated in the same nanoparticle.

In one aspect, the dactinomycin and the other chemotherapeutic may be administered simultaneously or sequentially, but in encapsulated in different nanoparticles.

In one aspect, the dactinomycin and the other chemotherapeutic may be administered simultaneously or sequentially, with the dactinomycin encapsulated in nanoparticles and the other chemotherapeutic not encapsulated in a nanoparticle.

In one aspect, the dactinomycin nanoparticle and the other chemotherapeutic may be administered separately, i.e., sequentially. For example, the dactinomycin nanoparticle may be administered before the other chemotherapeutic. Alternatively, the dactinomycin nanoparticle may be administered after the other chemotherapeutic.

In one aspect, the duration between administration of the dactinomycin nanoparticle and the other chemotherapeutic may be on the order of minutes, hour, or days. For example, the duration between administration of the dactinomycin nanoparticle and the other chemotherapeutic is 5 minutes, 15 minutes, 30 minutes, 45 minutes, 1 hour, 1.5 hours, 2 hours, 4 hours, 6 hours, 8 hours, 10 hours, 12 hours, 18 hours, 1 day, 1.5 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In one aspect, the duration between administration of the dactinomycin nanoparticle and the other chemotherapeutic is longer than 1 month.

Examples of topoisomerase inhibitors include, without limitation, irinotecan, topotecan, camptothecin, lamellarin D, etoposide, teniposide, mitoxantrone, amsacrine, ellipticines, aurintricaboxylic acid, and HU-331.

Examples of platinum-based therapies include, without limitation, cisplatin, carboplatin, oxaliplatin, nedaplatin, triplatin tetranitrate, picoplatin, and satraplatin.

Examples of anthracycline antibiotics include, without limitation, daunorubicin, doxorubicin, epirubicin, or idarubicin.

Examples of taxanes include, without limitation, paclitaxel, docetaxel, baccatin III, and 10-deacetylbaccatin.

Examples of tyrosine kinase inhibitors include, without limitation, imatinib, enzastaurin, dasatinib, erlotinib, gefitinib, lapatinib, nilotinib, sorafenib, sunitinib, everolimus, sirolimus, and temsirolimus.

Examples of nucleoside analogs include, without limitation, cytarabine, gemcitabine, capecitabine, didanosine, vidarbine, BCX4430, emtricitabine, lamivudine, zalcitabine, abacavir, aciclovir, entecavir, stavudine, telbivudine, zidovudine, idoxuridine, and trifluridine.

Examples of FLT3 inhibitors include, without limitation, Rydapt® (midostaurin), sorafenib, lestaurtinib, quizartinib, ponatinib, crenolanib, and gliteritinib. (Fathi, A. T. et al. Eur. J. Haematol. 2017, 98: 330-336.)

Examples of drugs inhibiting hyper methylation include, without limitation, azacitidine, decitabine, and zebularine. (Flotho, C. et al. Leukemia (2009) 23, 1019-1028 and Figueroa, M. E. et al. Blood (2009) 114(16), 3448-3458.)

Dactinomycin compositions of the disclosure may be administered with FLT3 inhibitors. Results of clinical trials showed efficacy of dactinomycin in about 60% of the patients treated. Subset analysis showed that the non-responders to dactinomycin tested positive for the FLT3 mutation which is present in approximately 30% of AML patients tested. There are two types of FLT3 mutations: internal tandem duplications (ITD) near the juxtamembrane domain of the receptor and point mutations in the activation loop of the tyrosine kinase domain (TKD mutations). TKD mutations comprise approximately 7% of patients, while ITD mutations are less prevalent in pediatrics and AML patients who were previously categorized as having MDS. (Fathi, A. T. et al. Eur. J. Haematol. 2017, 98: 330-336.)

Combinations of the dactinomycin compositions of the disclosure with FLT3 inhibitors, e.g., Rydapt® (midostaurin), sorafenib, lestaurtinib, quizartinib, ponatinib, crenolanib, and gliteritinib, may provide greater efficacy in the treatment of AML patients.

Dactinomycin compositions of the disclosure may be administered with drugs inhibiting hyper methylation. Examples of drugs inhibiting hyper methylation include, without limitation, azacitidine, decitabine, and zebularine. (Flotho, C. et al. Leukemia (2009) 23, 1019-1028 and Figueroa, M. E. et al. Blood (2009) 114(16), 3448-3458.)

For any of the methods comprising the administration of one or more other chemotherapeutic drugs in addition to dactinomycin, i.e., dactinomycin encapsulated in nanoparticles, including topoisomerase inhibitors, platinum-based therapies, anthracycline antibiotics, taxanes, tyrosine kinase inhibitors, nucleoside analogs, FLT3 inhibitors, and hyper methylation inhibitors, the determination of the appropriate therapeutically effective amounts of the other chemotherapeutic drug is within the routine skill level of a person of ordinary skill in the art. Any commonly used therapeutically effective amounts of these additional chemotherapeutic drugs can be employed.

Methods of the disclosure may be combined with further administration of additional agents, including, without limitation, retinoic acid (e.g., all trans-retinoic acid), valproic acid, histone deacteylase inhibitors, proteasome inhibitors, farnesyltransferase inhibitors, p53 stabilizers, any combinations thereof.

In one aspect, the dactinomycin nanoparticle and the additional agents may be administered separately, i.e., sequentially. For example, the dactinomycin nanoparticle may be administered before the additional agents. Alternatively, the dactinomycin nanoparticle may be administered after the additional agents.

In one aspect, the duration between administration of the dactinomycin nanoparticle and the additional agents may be on the order of minutes, hour, or days. For example, the duration between administration of the dactinomycin nanoparticle and the other chemotherapeutic is 5 minutes, 15 minutes, 30 minutes, 45 minutes, 1 hour, 1.5 hours, 2 hours, 4 hours, 6 hours, 8 hours, 10 hours, 12 hours, 18 hours, 1 day, 1.5 days, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In one aspect, the duration between administration of the dactinomycin nanoparticle and the additional agents is longer than 1 month.

Histone deacteylase inhibitors include, without limitation, Class I inhibitors (HDAC-1, -2, -3, and -8), Class II inhibitors (HDAC-4, -5, -6, -7, -9, and -10), Class II inhibitors (sirtuins), and Class IV inhibitors (HDAC-11). For example, the histone deacetylase inhibitor is vorinostat, romidepsin, chidamide, panobinostat, belinostat, valproic derivatives, e.g., Mg valproate, mocetinostat, abexinostat, entinostat, SB939, resminostat, givinostat, quisinostat, HBI-8000, Kevetrin, CUDC-101, AR-42, CHR-2845, CHR-3996, 4SC-202, CG200745, ACY-1215, ME-344, or sulforaphane.

Proteasome inhibitors include, without limitation, lactacystin, disulfiram, epigallocatechin-3-gallate, merixomib (salinosporamide A), oprozomib, delanzomib, epoxomicin, MG132, beta-hydroxy beta-methylbutyrate, bortexomib, carfilzomib, and ixazomib.

Farnesyltransferase inhibitors include, without limitation, tipifarnib, lonafarnib, chaetomellic acid A, clavaric acid, FPT inhibitor I (sc-221625), FPT inhibitor II (sc-221626), FPT inhibitor III (sc-221627), FPTase inhibitor I (sc-221632), FPTase inhibitor II (sc-221633), FTI-277 trifluoroacetate salt, CGTI-297, L-744,832 dihydrochloride, manumycin A, gingerol, gliotoxin, and alpha-hydroxyl farnesyl phosphonic acid.

p53 stabilizers include, without limitation, Tenovin-1, BI2536, CP-31398, RbBP6 isoform 3, CBS9106 (Chen, L et al. Cell Cycle 2016, 15(6): 840-849; Journal of Clinical Oncology, 2009 ASCO Annual Meeting Proceedings (Post-Meeting Edition). Vol 27, No 155, 2009: 8601; Dlamini, Z. et al. Proceedings: AACR 101st Annual Meeting 2010 Apr. 17-21, 2010).

As used herein in other contexts, the term "about," unless indicated otherwise, refers to the recited value, e.g., amount, molecular weight, dose, temperature, time, percentage, etc., +/−10%, +/−9%, +/−8%, +/−7%, +/−6%, +/−5%, +/−4%, +/−3%, +/−2%, or +/−1%.

All percentages and ratios used herein, unless otherwise indicated, are by weight. Other features and advantages of the disclosure are apparent from the different examples. The provided examples illustrate different components and methodology useful in practicing the disclosure. The examples do not limit the claimed invention. Based on the present disclosure the skilled artisan can identify and employ other components and methodology useful for practicing the disclosure.

EXAMPLES

In order that the disclosure disclosed herein may be more efficiently understood, examples are provided below. It should be understood that these examples are for illustrative purposes only and are not to be construed as limiting the disclosure in any manner.

Example 1: Pharmacokinetics of Dactinomycin

FIGS. 1A and B are each graphs demonstrating the systemic concentration of dactinomycin over time. The data in these graphs are taken from 21 patients aged 16-53 years, administered with 1 mg/m$^2$ (27 μg/kg) of dactinomycin. These data indicate that the majority of dactinomycin is released at high concentration with the first hour after administration to the subject. The initial high release may contribute with the toxicities and adverse events associated with dactinomycin administration.

Figure 2:
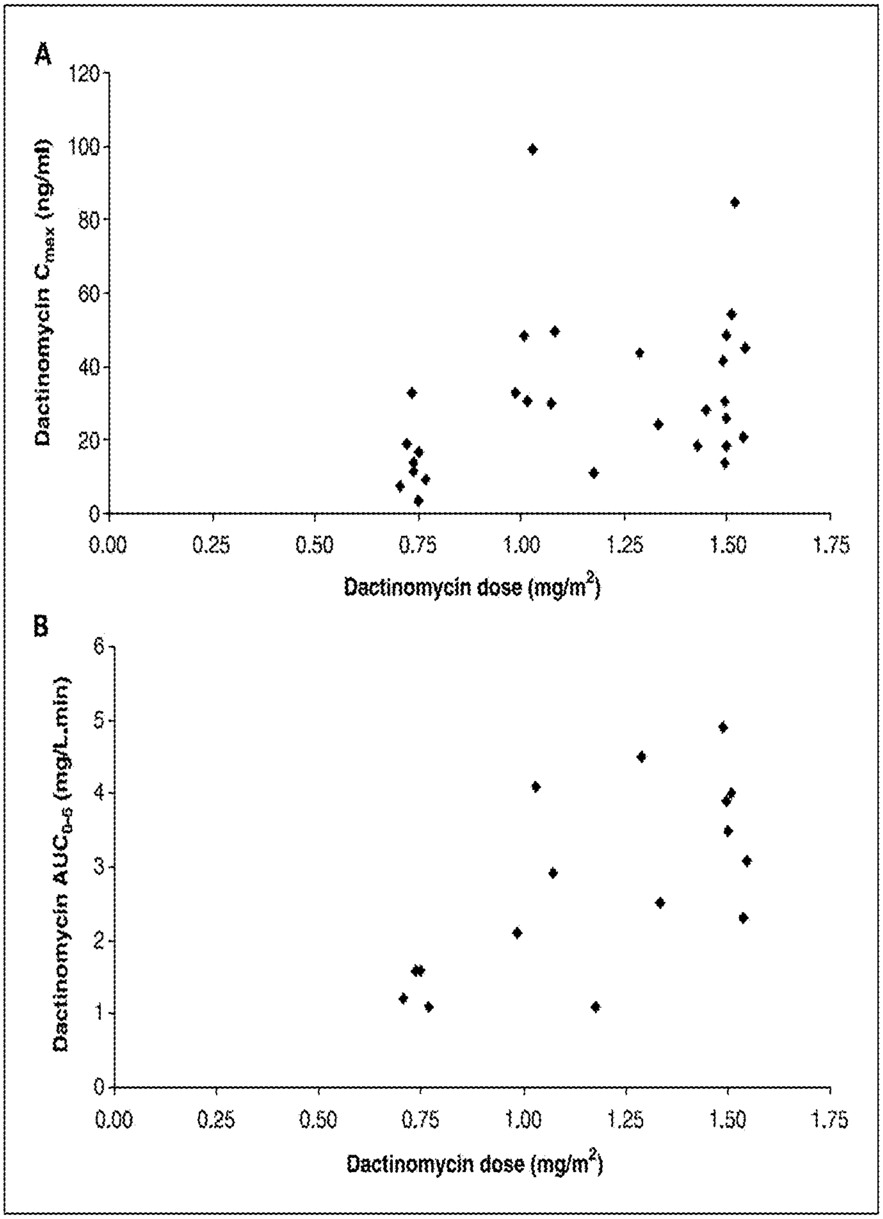
FIG. 2 is a pair of graphs demonstrating the $C_{max}$ (ng/mL) (graph A) and $AUC_{0\text{-}6\ hrs}$ (mg/L*min) (graph B) as a function of dactinomycin dose ($mg/m^2$).
Figure 3:
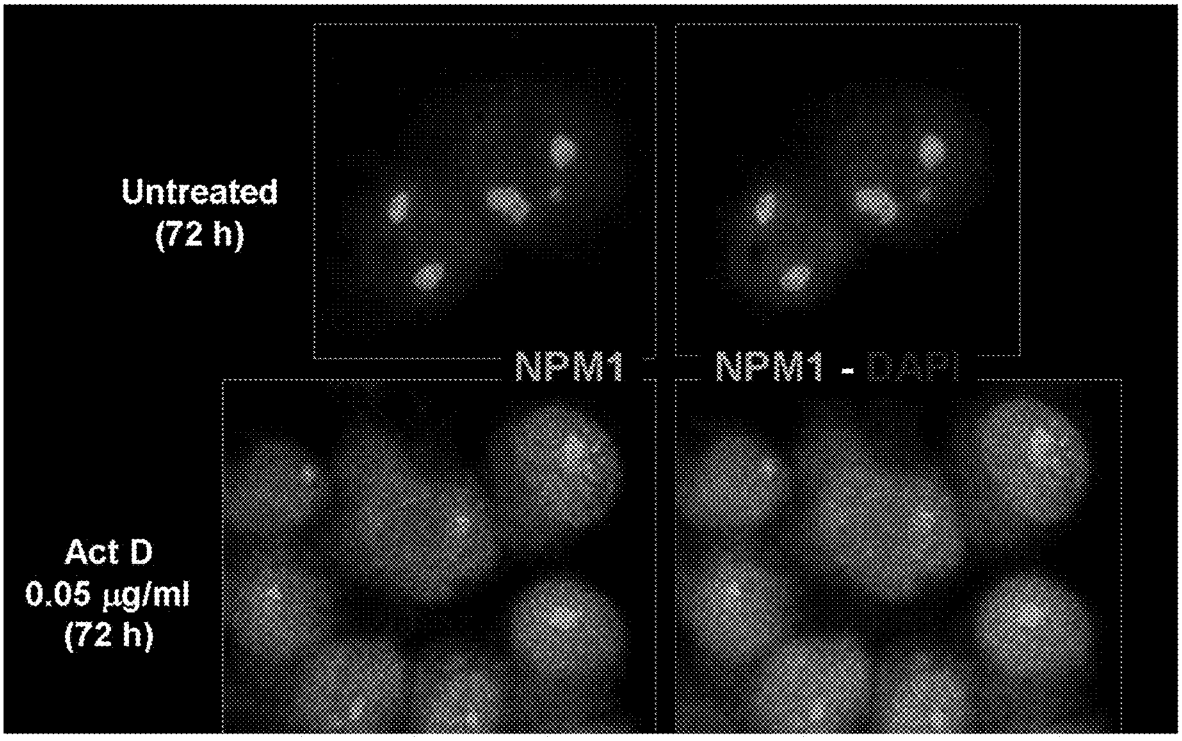
FIG. 3 is a series of photographs demonstrating Act-D induced nucleolar disintegration and apoptosis in NPM1-mutated cell line OCI/AML3. NPM1=Nucleophosmin and DAPI=4',6-diamidino-2-phenylindole—a fluorescent stain that binds strongly to A-T rich regions in DNA.
Figure 4:
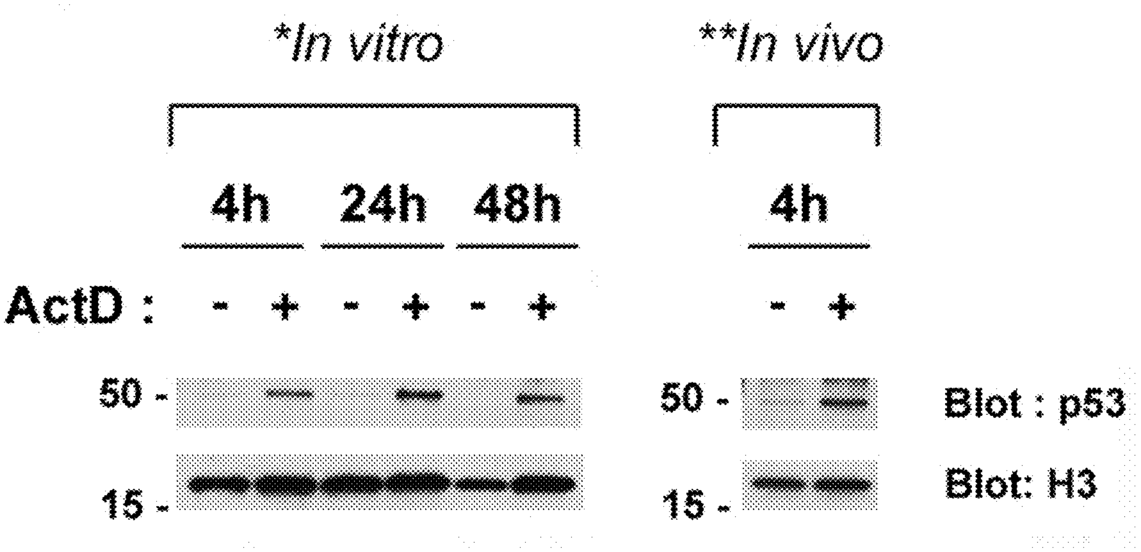
FIG. 4 is a series of photographs of Western blots demonstrating p53 activation upon administration of dactinomycin to NPM1-mutated AML tumor cells contacted in vitro or in vivo (cells biopsied following treatment) of patient M.M. (60 year old woman with pancyopenia, massive blasts infiltration of bone marrow, diagnosed with NPM1-mutated AML, unfit for chemotherapy due to low left ventricular ejection fraction due to previous myocardial infarction, treated initially with Azacitidine but experienced disease progression, so treated with actinomycin D (because it is not cardiotoxic) for 2 cycles of 5 consecutive days each at 12.5 μg/kg).
Figure 6A:
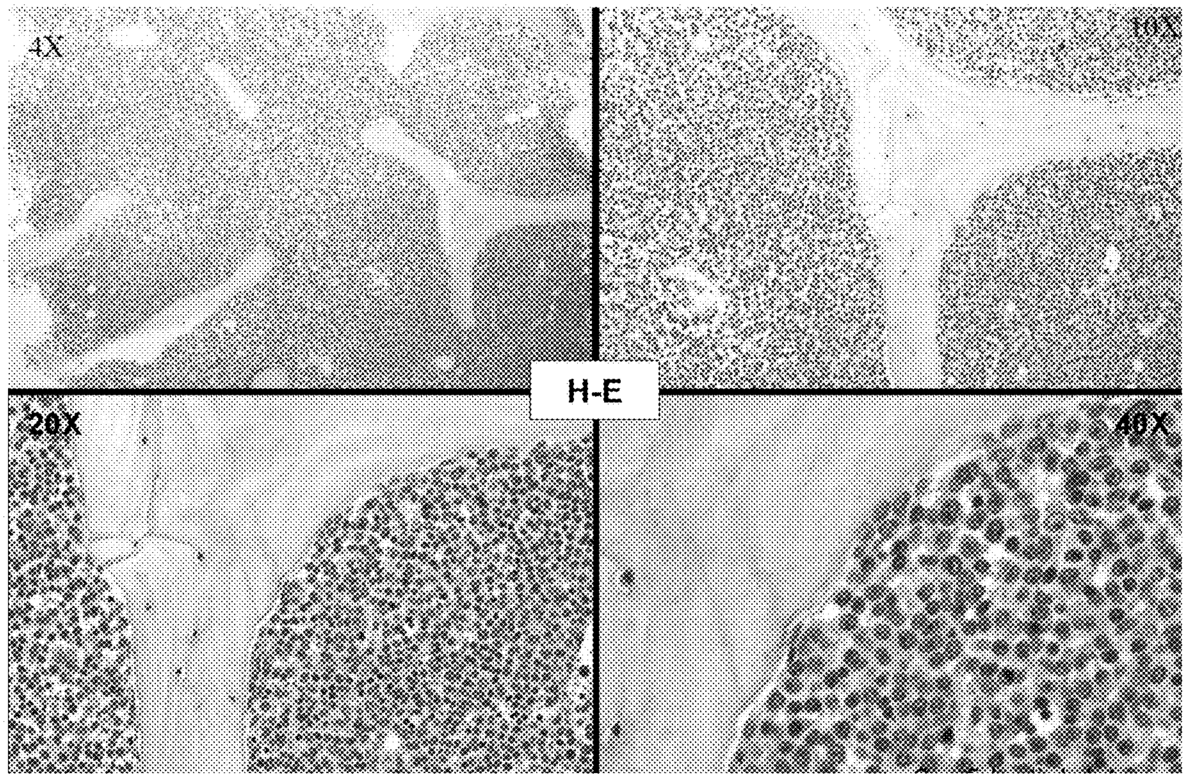
FIGS. 6A and B are a series of photographs showing Hematoxylin and Eosin stain (H-E stains) of bone marrow biopsies at Relapse, pre-dactinomycin treatment. PGM1=Phosphoglucomutase 1 and MPO=Myeloperoxidase.
Figure 6B:
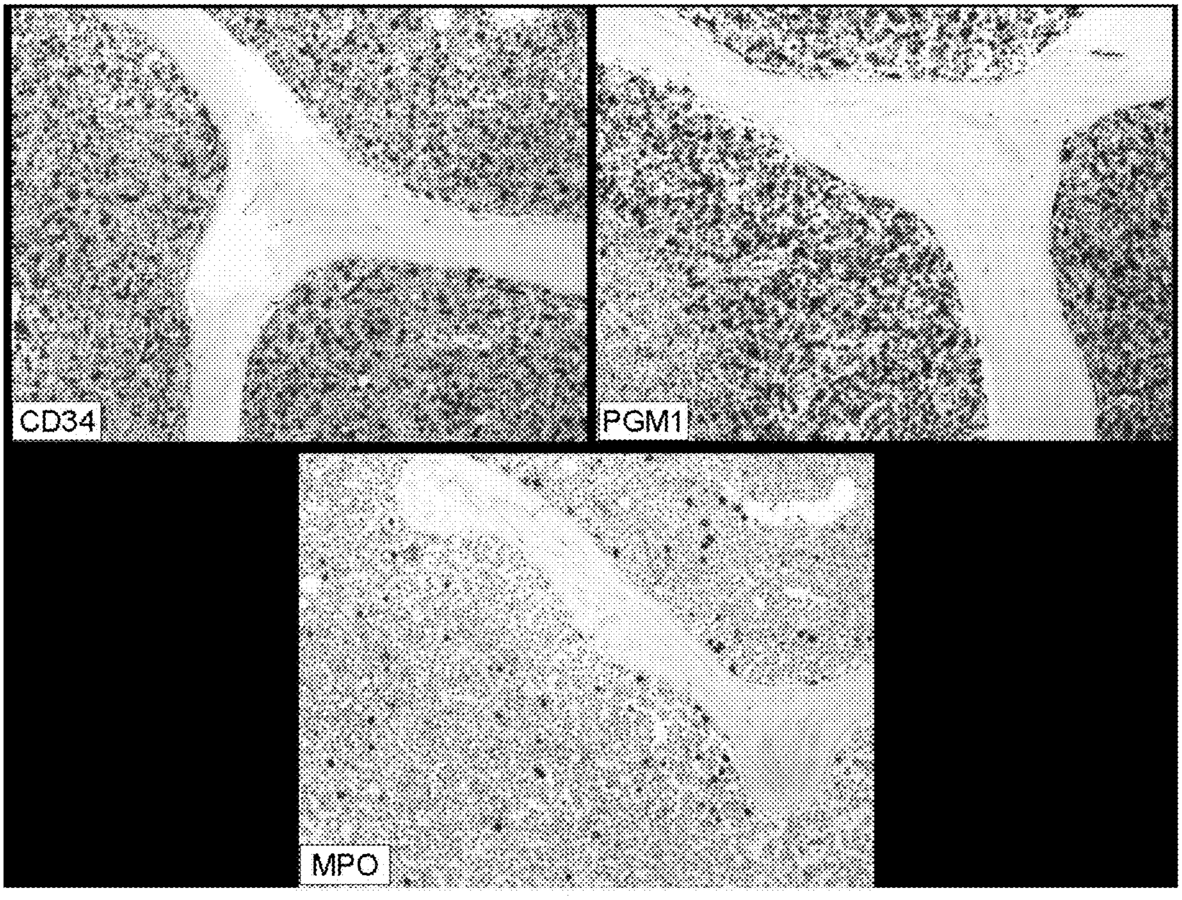
Figure 7:
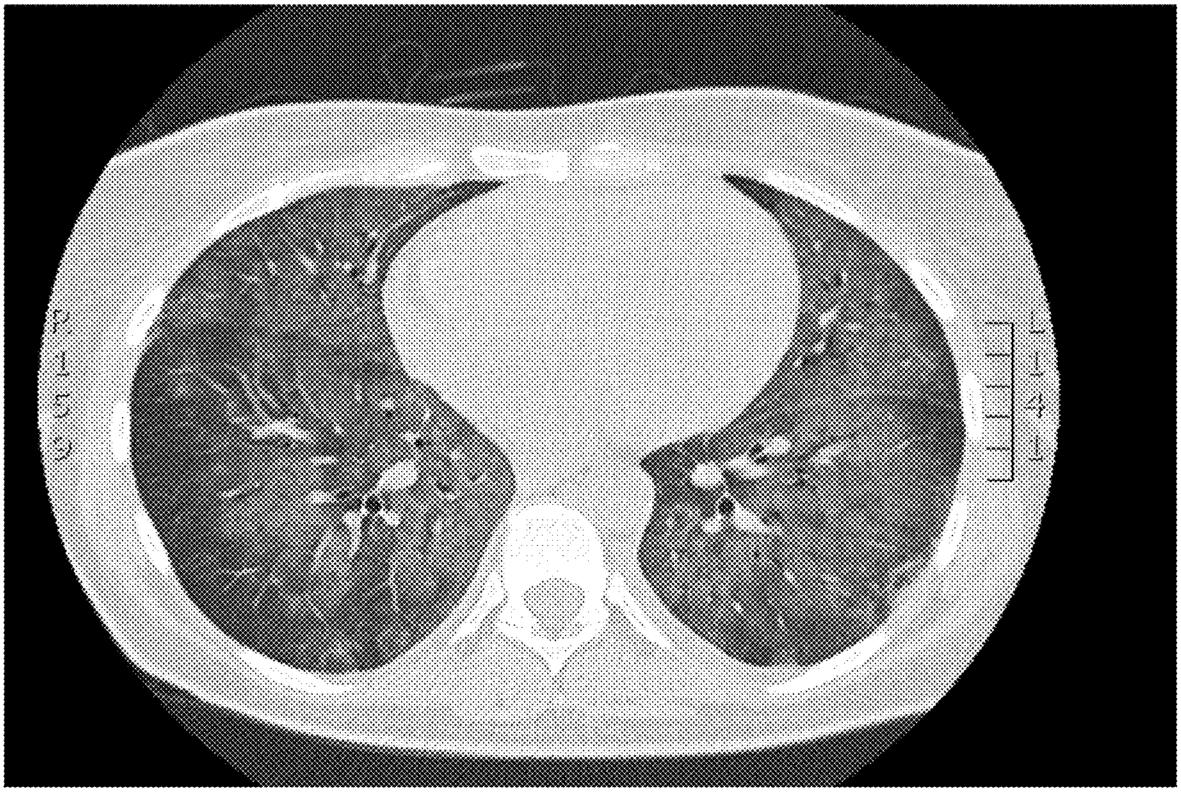
FIG. 7 is a photograph of a computerized tomography (CT) scan showing pneumonitis in a subject administered dactinomycin at 15 μg/kg for 5 days.
Figure 9A:
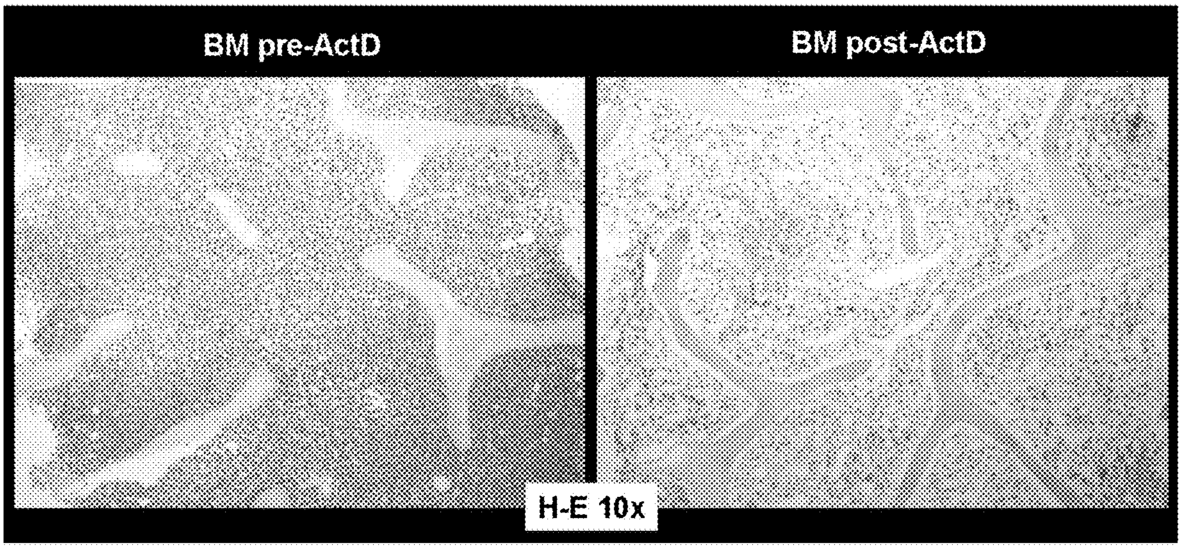
FIGS. 9A and B are a pair of photographs depicting a bone marrow (BM) examination before and after therapy with dactinomycin alone. BM examination after therapy with ActD showed marked reduction of leukemic blast infiltration with partial normal hematopoietic recovery.
Figure 9B:
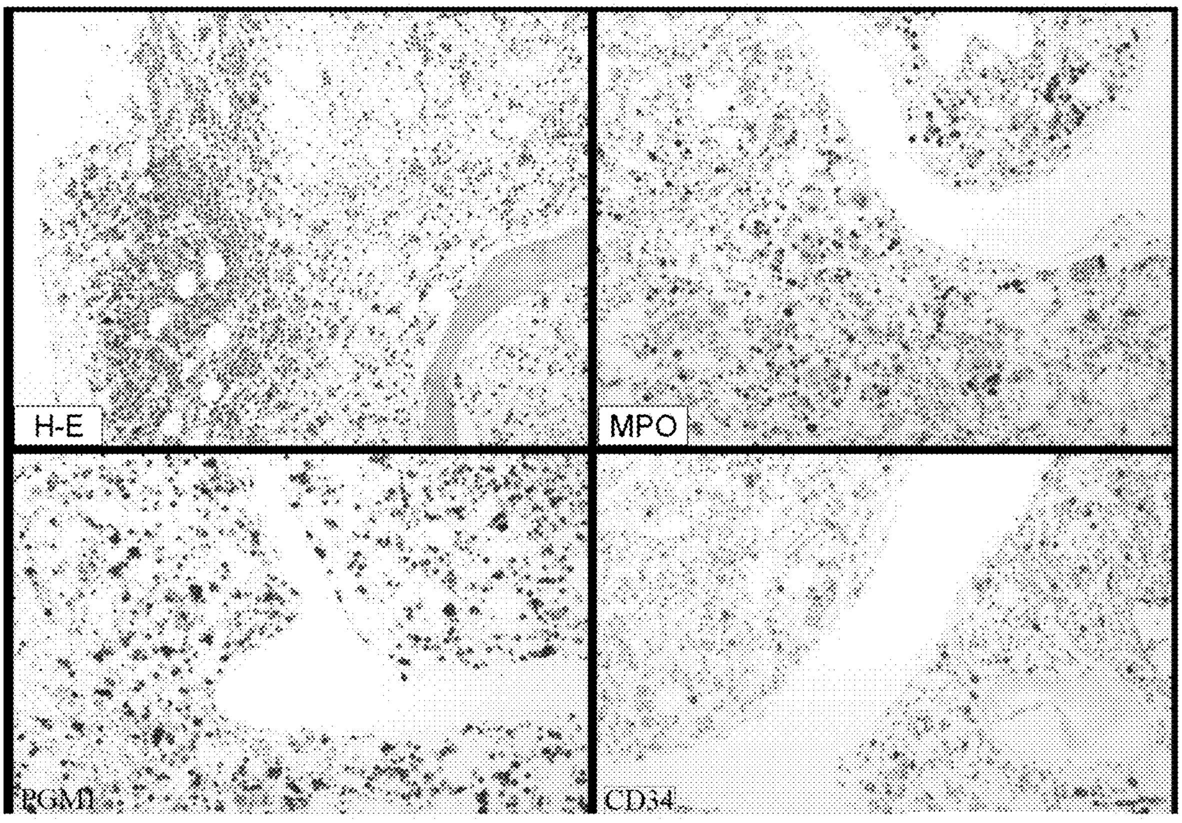
Figure 10:
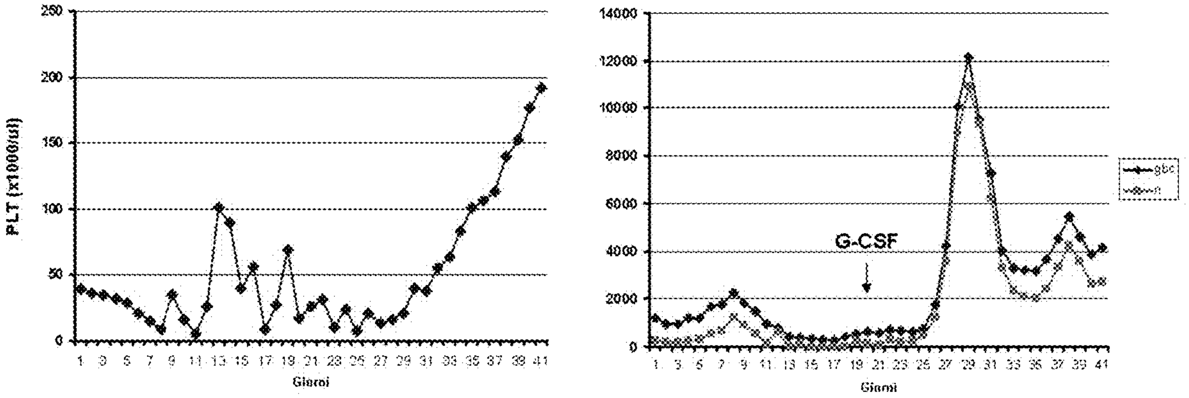
FIG. 10 is a pair of graphs demonstrating homological recovery upon treatment with dactinomycin+low-dose cytarabine (LDAC). Complete blood count (CBC) d=46, white blood cell 4130/$mm^3$, neutrophil percent (N=66%), hemoglobin (Hb)=7.7 g/dL, platelet (PLT) count 192.000/$mm^3$. Erythropoietin (EPO) dosage=17.8 mUl/ml (inappropriate response). Patient started on Darbopoetina.
Figure 11:
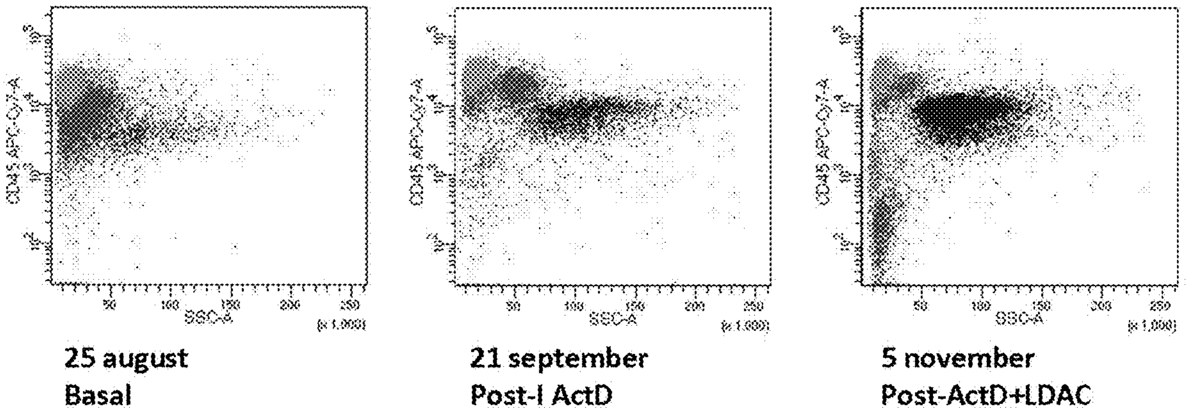
FIG. 11 is series of flow cytometry plots demonstrating clearance of leukemic blasts.
Figure 12:
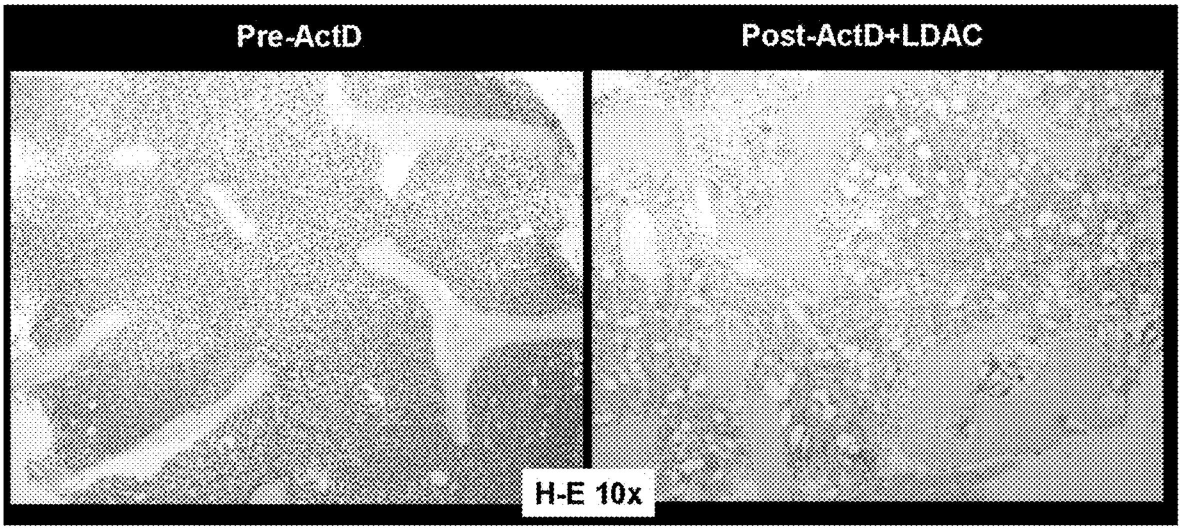
FIG. 12 is a pair of photographs depicting a bone marrow (BM) examination before and after therapy with dactinomycin+LDAC (right), showing complete hematological remission with normal trilinear hematopoietic recovery.
Figure 13:
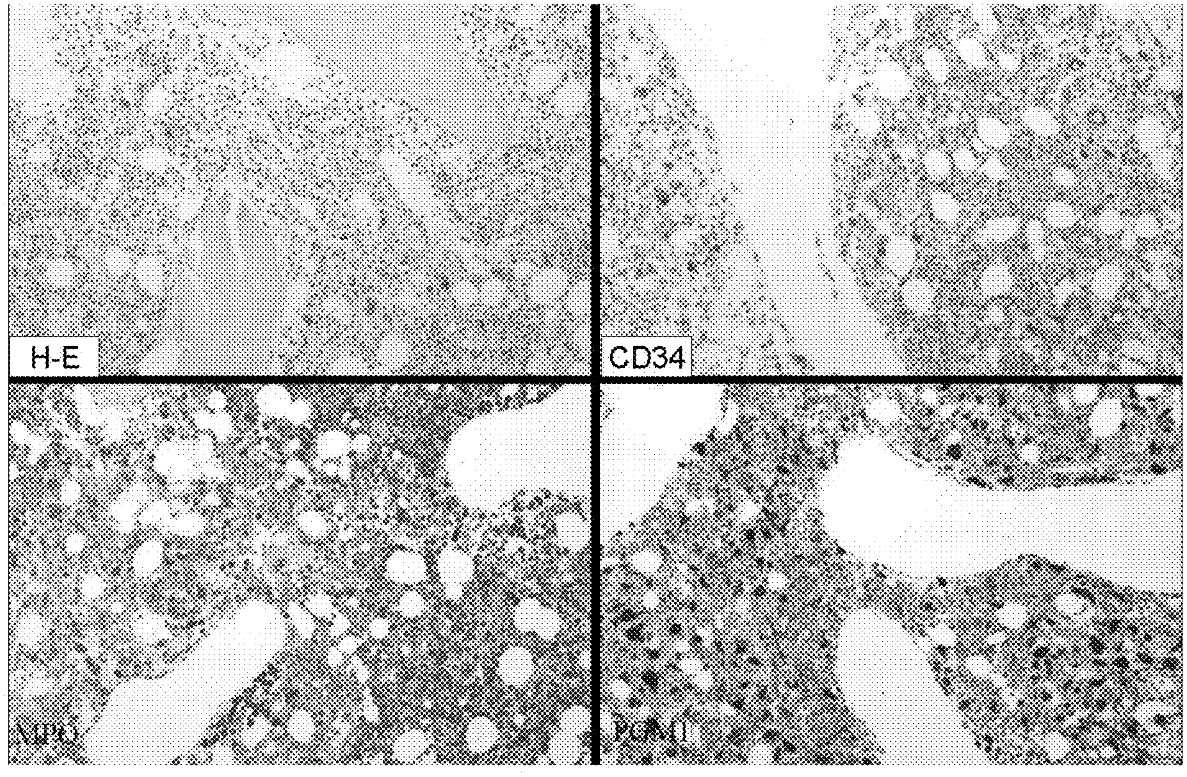
FIG. 13 is a series of photographs depicting a bone marrow biopsy post-dactinomycin+LDAC.
Figure 14:
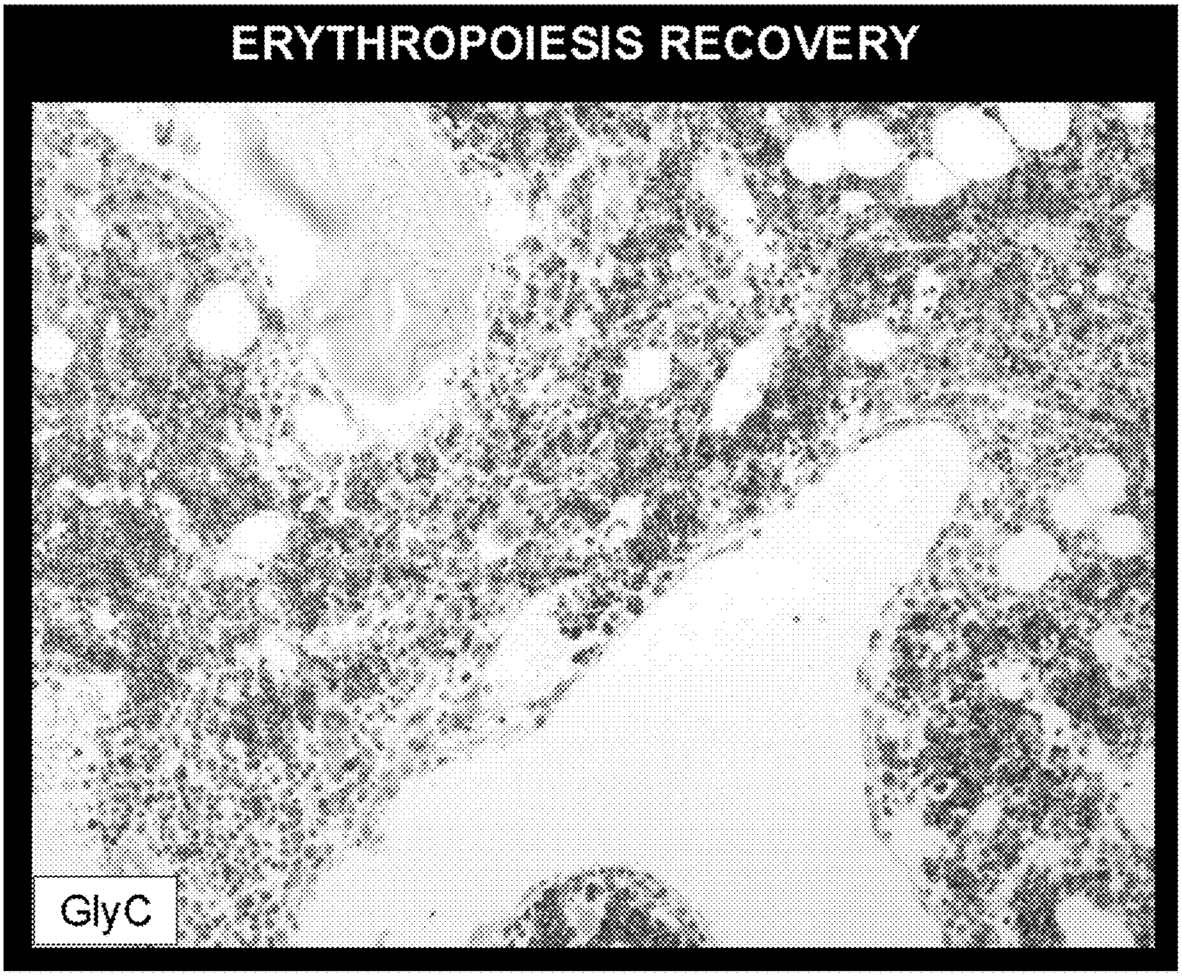
FIG. 14 is a photograph depicting erythropoiesis recovery. GlyC=Serine hydroxymethyltransferase, cytosolic.

FIG. 2 is a pair of graphs demonstrating the $C_{max}$ (ng/mL) (graph A) and $AUC_{0-6}$ hrs (mg/L*min) (graph B) as a function of dactinomycin dose (mg/m$^2$). The IV dose for subjects younger than 30 years old is 1 mg/m$^2$ (27 μg/kg) and 1.5 mg/m$^2$ (40 μg/kg) for subjects 30 years and older. Subjects with $AUC_{0-6}$ hrs showed more adverse events. $AUC_{0-6}$ hrs in patients showing adverse events were 1.46 times higher (4 mg/L*min) than those subjects no showing adverse events (2.67 mg/L*min).

Example 2: Preparation of Actinomycin D Encapsulated Nanoparticles

Actinomycin D was dissolved in dichloromethane (DCM) as a 25 mg/mL stock solution ("API solution"). Resomer R 202S and R 203H were prepared at the same concentration in DCM, Resomer D5050 DLG mPEG 5000 (35 wt %, PEG) and 100 DL mPEG 5000 (25 wt %, PEG) were prepared at 50 mg/mL in DCM. The API solution was added into polymer solution until the amount of the polymer to API reached 10:1 ratio (w/w). The final solution was vortexed until homogeneous before use. 2% Poly (vinyl alcohol), PVA (MW 9,000-10,000 Da, 80% hydrolyzed), was prepared as water phase with surfactant. To make nanoparticle emulsion, the polymer/Actinomycin D solution was added dropwise into small amount of water phase while the water phase was on high vortex. After the entire polymer solution was added (organic:water phase ratio was about 1:7 by volume, the formed emulsion was vortexed thoroughly for an additional 20 seconds. The mixture was immediately transferred to the ultrasonicator (Fisher Scientific Sonic Dismembrator Model 500). The emulsion was immersed in an ice water bath (0° C.) and sonicated for 5-8 minutes (65% amplitude, 20 seconds on, 8 seconds off) until desired particle size was reached (below 200 nm). Nanoparticle size was checked periodically using Malvern Nano-ZS zeta sizer. The emulsion was then poured into stirring bulk water phase (2% PVA) solution and stirred (500 rpm) at room temperature for at least 3 hours until DCM evaporated completed.

For nanoparticle purification, hardened or cured nanoparticles were centrifuged in a fixed-angle rotor (Eppendorf Centrifuge 5415C) for 30 minutes at 14,000× rpm. The supernatant was discarded and nanoparticles were washed with dd$H_2O$ and centrifuged at 14,000× rpm for another 30 minutes. To remove the bigger particles, pellet was resuspended in dd$H_2O$ and centrifuged at 3,500× rpm for 5 minutes. Collected supernatant was then concentrated by an Amicon® Ultra Centrifugal filter (50 kD cut-off) and centrifuged for 10 minutes at 14,000× rpm to remove free drug. The purified nanoparticles can be used freshly, stored at 4° C. for up to weeks or lyophilized after lyo- and cryo-protection with sucrose (10-30%). Drug loading was tested using HPLC.

Further guidance on the preparation of ActD nanoparticle formulation can be found in McCall, R. L. et al. J. Vis. Exp. (82), e51015, which is incorporated by reference in its entirety.

Example 3: Representative ActD Nanoparticle Formulations

The following ActD nanoparticle formulation were prepared according to the previous example.

| Polymer type/ description | Polymer M.W. | Viscosity | End Group | Tm | Tg | Half Life | Surfactant | NP Size Z-Ave (d.nm) | PdI |
|---|---|---|---|---|---|---|---|---|---|
| A | 10,000-18,000 | 0.16-0.24 dL/g | ester terminated | | 38-42° C. | <6 months | 2% PVA | 176.3 | 0.060 |
| B | 18,000-24,000 | 0.25-0.35 dL/g | acid terminated | | 48-52° C. | <6 months | 2% PVA | 187.0 | 0.066 |
| C | 30,000 | 0.33-0.45 dL/g | | 48° C. | 9° C. | | 2% PVA | 158.4 | 0.170 |
| D | 22,000 | 0.33 dL/g | | 50° C. | −5° C. | | 2% PVA | 140.5 | 0.077 |

A: Resomer ® R 202 S (Poly(D,L-lactide))
B: Resomer ® R 203 H (Poly(D,L-lactide))
C: Resomer Select 100DL mPEG 5000 (25% PEG) GMP (Poly(D,L-lactide)-b-poly(ethylene glycol) methyl ether 5000)
D: Resomer Select 5050 DLG mPEG 5000 (35% PEG) (lactide:glycolide ~50:50 PEG: 35 wt %)

Figure 15:
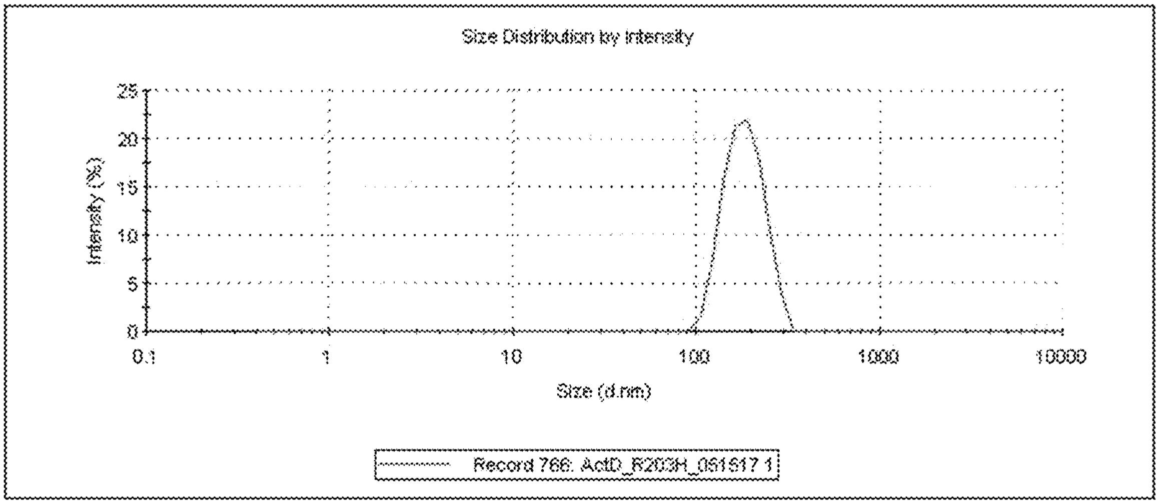
FIG. 15 is a graph shows the nanoparticle size distribution of a composition prepared with dactinomycin and Resomer® R 203 H (PLA).

For example, dactinomycin encapsulated nanoparticles comprising Resomer® R 203 H, were determined to have a purity of 96.3%, with nanoparticles having an average size of 176.9 nm. (FIG. 15). Zeta potential: −23.63+/−0.49.

| Assay (mg/mL) | Purity (%) |
|---|---|
| 1.011 | 96.3 |

Figure 16:
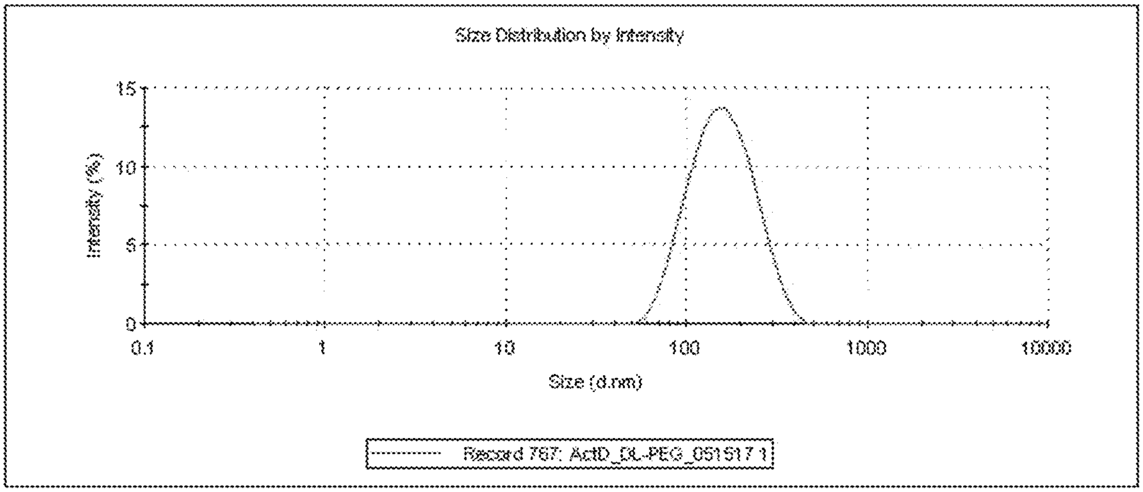
FIG. 16 is a graph shows the nanoparticle size distribution of a composition prepared with dactinomycin and Resomer® 100 DL mPEG 5000 (25% mPEG) (PLA-mPEG).

For example, dactinomycin encapsulated nanoparticles comprising Resomer® 100 DL mPEG 5000 (25% mPEG), were determined to have a purity of 96.7%, with nanoparticles having an average size of 143.5 nm. (FIG. 16). Zeta potential: −45.93+/−2.54.

| Assay (mg/mL) | Purity (%) |
|---|---|
| 0.534 | 96.7 |

Figure 17:
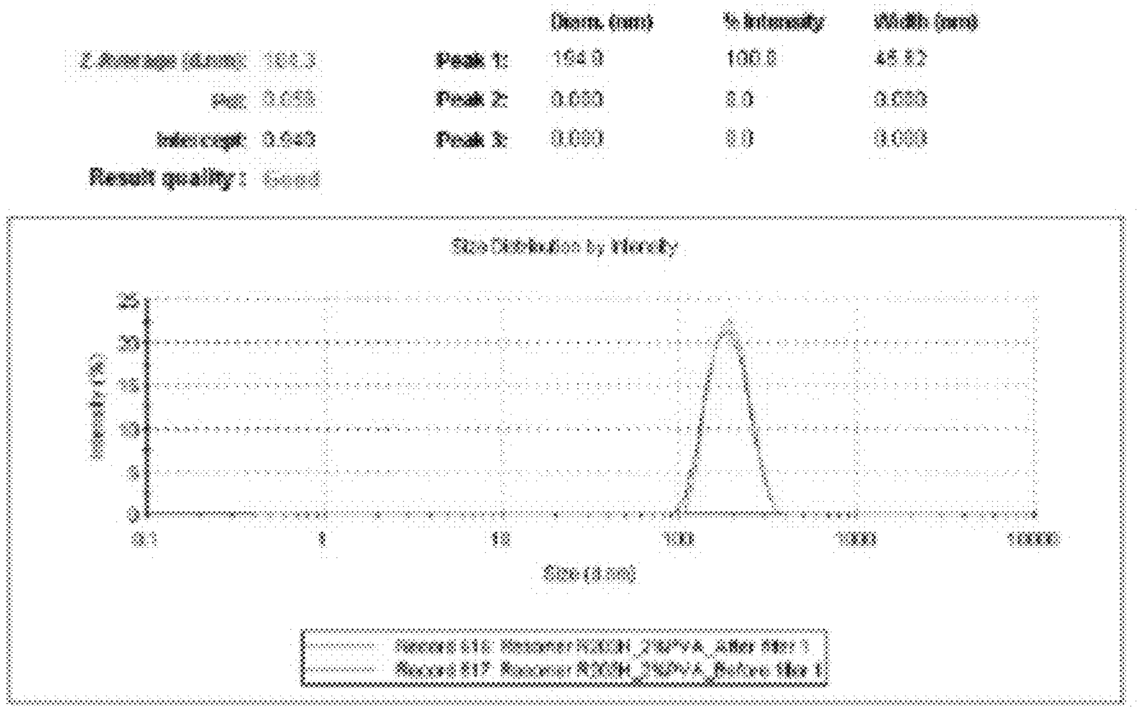
FIG. 17 is a graph that shows the nanoparticle size distribution of a composition prepared with dactinomycin and Resomer® R 203 H (PLA), after the composition was passed through a 200 nm surfactant free cellulose acetate membrane filter (bottom line).
Figure 18:
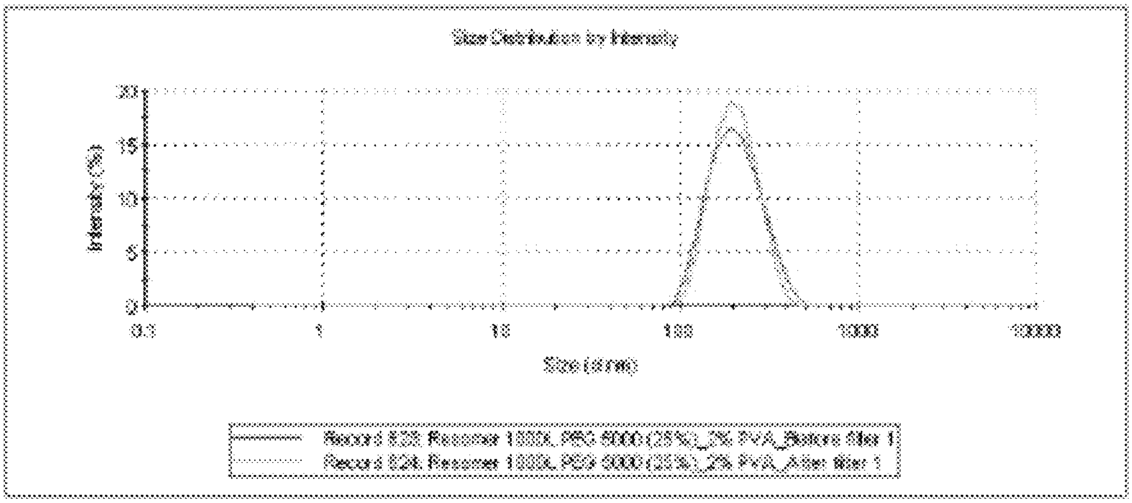
FIG. 18 is a graph that shows the nanoparticle size distribution of a composition prepared with dactinomycin and Resomer® 100 DL mPEG 5000 (25% mPEG) (PLA-mPEG), after the composition was passed through a 200 nm surfactant free cellulose acetate membrane filter (top line).

The above two dactinomycin encapsulated nanoparticles examples (Resomer® R 203 H (FIG. 17) and Resomer® 100 DL mPEG 5000 (25% mPEG) (FIG. 18)) were passed through 200 nm surfactant free cellulose acetate membrane filter. Recovery rates: 79.3% (Resomer® R 203 H); 55.2% (Resomer® 100 DL mPEG 5000 (25% mPEG)).

Example 4: Stability of ActD Nanoparticle Formulations

All four of the above dactinomycin encapsulated nanoparticles were found to be stable for 1 month in purified water at −20° C., 4° C., and 25° C.

Figure 19:
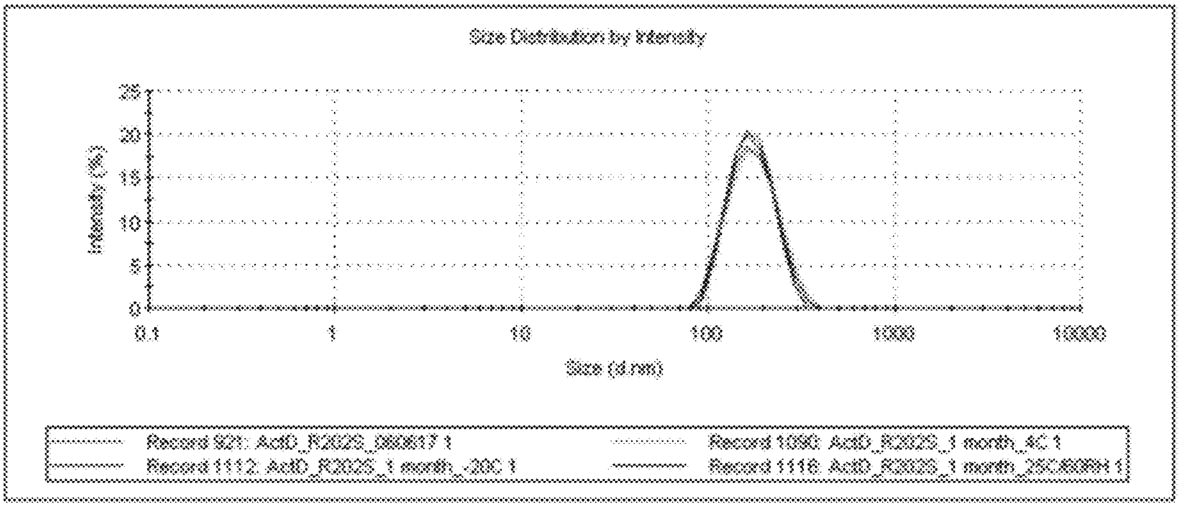
FIG. 19 is a graph that shows the nanoparticle size distribution of a composition prepared with dactinomycin and Resomer® R 202 S, after assessing the stability of the composition in various conditions. (T0=

For example, dactinomycin encapsulated nanoparticles comprising Resomer® R 202 S, retained purity of greater than 94% for 1 month under all of these conditions. Zeta potential: −11.90+/−2.18 mV (1 month at −20° C.); −5.77+/−0.98 mV (1 month at 4° C.); −14.37+/−0.47 mV (1 month at 25 C/60RH). Storage conditions: 30% sucrose (−20° C.); purified water (4° C. and 25° C./60RH). (FIG. 19)

| | Purity (%) |
|---|---|
| T 0 | 96.49 |
| 1 month at −20° C. | 96.81 |
| 1 month at 4° C. | 95.93 |
| 1 month at 25° C./60RH | 94.47 |

Figure 20:
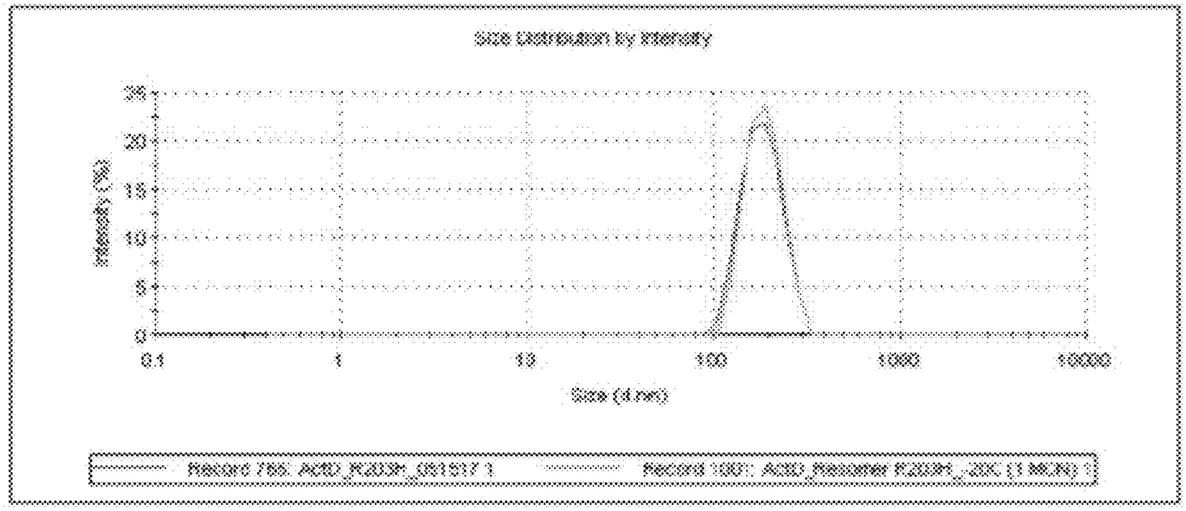
FIGS. 20 and 21 are graphs that show the nanoparticle size distribution of a composition prepared with dactinomycin and Resomer® R 203 H, after assessing the stability of the composition in various conditions.
Figure 21:
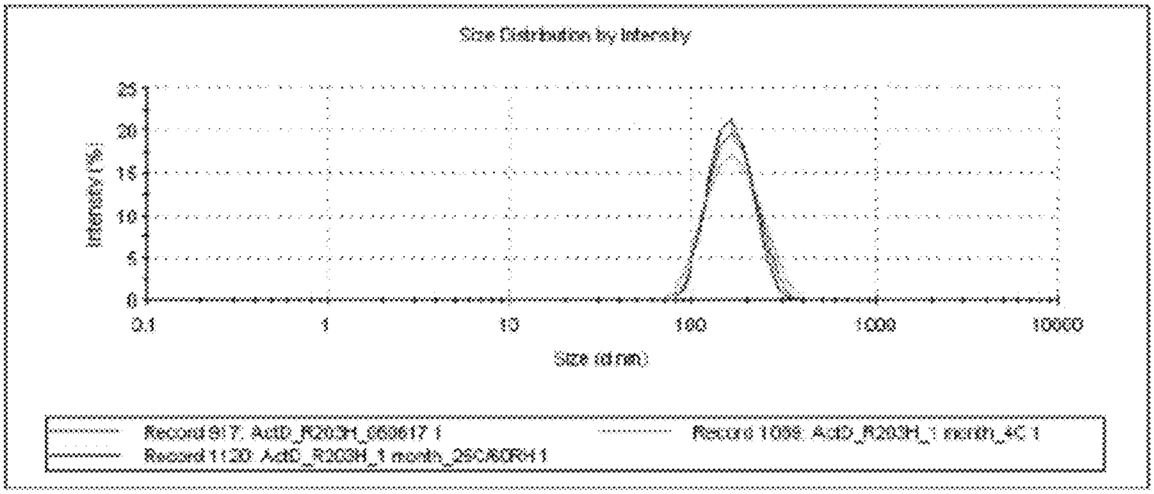

For example, dactinomycin encapsulated nanoparticles comprising Resomer® R 203 H, retained purity of greater than 95% at for 1 month under all of these conditions. Zeta potential: −23.63+/−0.49 mV ($T_0$); −0.59+/−3.07 mV (1 month at −20° C.); −9.06+/−1.37 mV (1 month at 4° C.); −13.76+/−0.51 mV (1 month at 25° C./60RH). Storage conditions: 30% sucrose (−20° C.); purified water (4 C and 25° C./60RH). (20° C.: FIG. 20. 4° C. and 25° C./60RH: FIG. 21)

| | Purity (%) | | Purity (%) |
|---|---|---|---|
| T 0 | 96.3 | T 0 | 97.0 |
| 1 month at −20° C. | 95.9 | 1 month at 4° C. | 96.5 |
| | | 1 month at 25° C./60RH | 95.1 |

Figure 22:
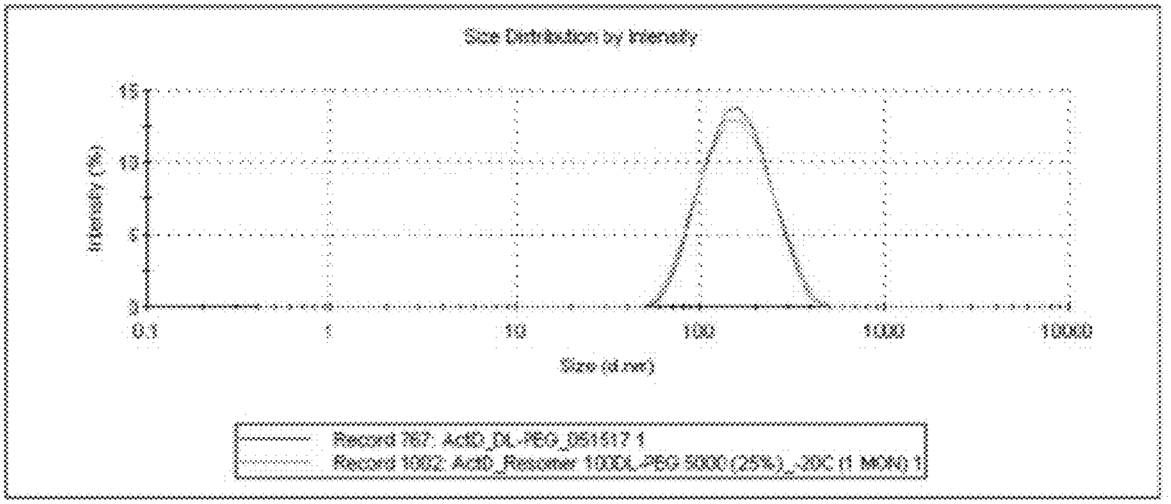
FIGS. 22 and 23 are graphs that show the nanoparticle size distribution of a composition prepared with dactinomycin and Resomer® 100DL mPEG 5000 (25%), after assessing the stability of the composition in various conditions.
Figure 23:
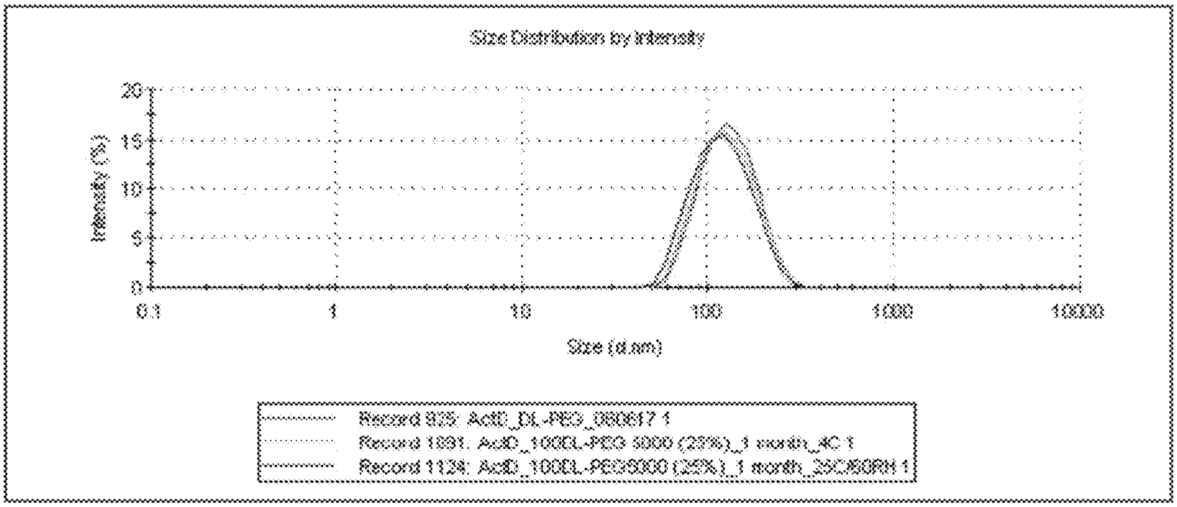

For example, dactinomycin encapsulated nanoparticles comprising Resomer® 100DL mPEG 5000 (25%), retained purity of greater than 95% at for 1 month under all of these conditions. Zeta potential: −45.93+/−2.54 mV ($T_0$); −8.74+/−0.56 mV (1 month at −20° C.); −11.07+/−0.23 mV (1 month at 4° C.); −9.89+/−0.71 mV (1 month at 25° C./60RH). Storage conditions: 30% sucrose (−20° C.); purified water (4° C. and 25° C./60RH). (−20° C.: FIG. 22. 4° C. and 25° C./60RH: FIG. 23.)

| | Purity (%) | | Purity (%) |
|---|---|---|---|
| T 0 | 96.7 | T 0 | 97.1 |
| 1 month at −20° C. | 95.9 | 1 month at 4° C. | 95.7 |
| | | 1 month at 25° C./60RH | 95.2 |

For example, dactinomycin encapsulated nanoparticles comprising Resomer® 5050DLG mPEG 5000 (35%), retained purity of greater than 94% at for 1 month under all of these conditions. Zeta potential: −45.93+/−2.54 mV ($T_0$); −3.83+/−0.61 mV (1 month at −20° C.); −9.74+/−0.95 mV (1 month at 4° C.); −17.63+/−1.06 mV (1 month at 25° C./60RH). Storage conditions: 30% sucrose (−20° C.); purified water (4° C. and 25° C./60RH).

Figure 24:
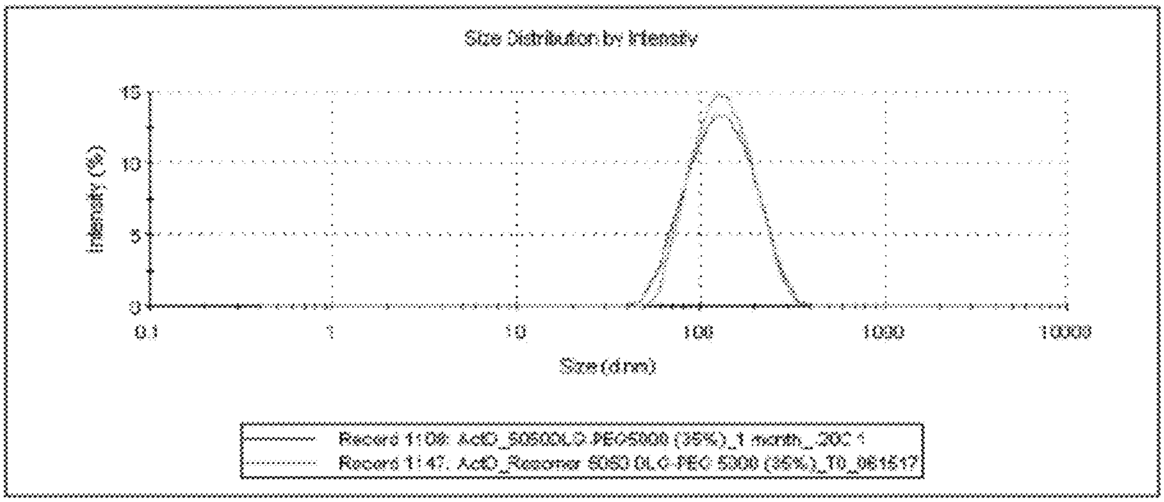
FIGS. 24 and 25 are graphs that show the nanoparticle size distribution of a composition prepared with dactinomycin and Resomer® 5050DLG mPEG 5000 (35%), after assessing the stability of the composition in various conditions.
Figure 25:
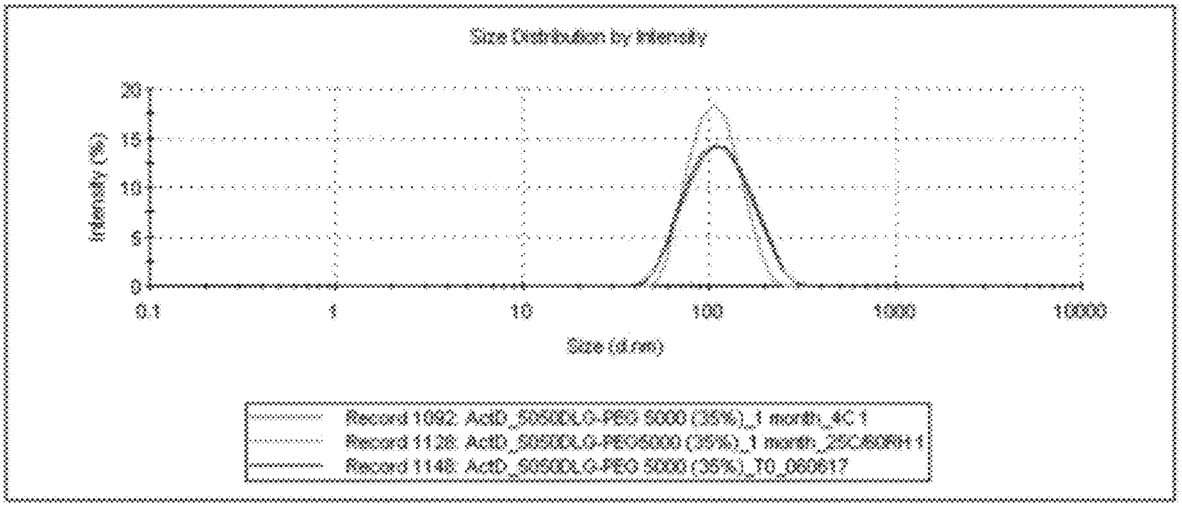

(−20° C.: FIG. 24. 4° C. and 25° C./60RH: FIG. 25.)

| | Purity (%) |
|---|---|
| T 0 | 96.8 |
| 1 month at −20° C. | 95.2 |
| T 0 | 96.8 |
| 1 month at 4° C. | 95.4 |
| 1 month at 25° C./60RH | 94.8 |

Figure 26:
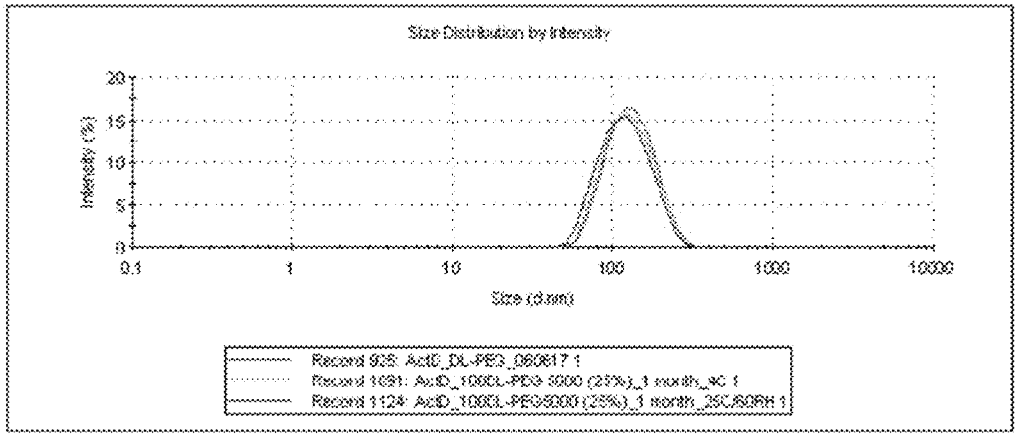
FIG. 26 is a graph that shows the nanoparticle size distribution of a composition prepared with dactinomycin and PEG-ylated poly, D,L lactide, after assessing the stability of the composition in various conditions.

For example, dactinomycin encapsulated nanoparticles comprising PEG-ylated poly, D,L lactide retained purity of greater than 95% at for 1 month under all of these conditions. Zeta potential: −11.07+/−0.23 mV (1 month at 4° C.); −9.89+/−0.71 mV (1 month at 25° C./60RH). (FIG. 26.)

| | Purity (%) |
|---|---|
| T 0 | 97.1 |
| 1 month at 4° C. | 95.7 |
| 1 month at 25° C./60RH | 95.2 |

Example 5: In Vitro of Release of Dactinomycin Encapsulated Nanoparticles—Comparison of mPEGylated and Non-mPEGylated Nanoparticles The four prototype dactinomycin encapsulated nanoparticles compositions demonstrated 3-10 days extended release in vitro.

Non-PEGylated polymer (R203H) exhibited slow and sustained release of dactinomycin over 12 days compared to mPEGylated (100 DL-PEG and 50:50 DLG PEG) polymers.

Figure 27:
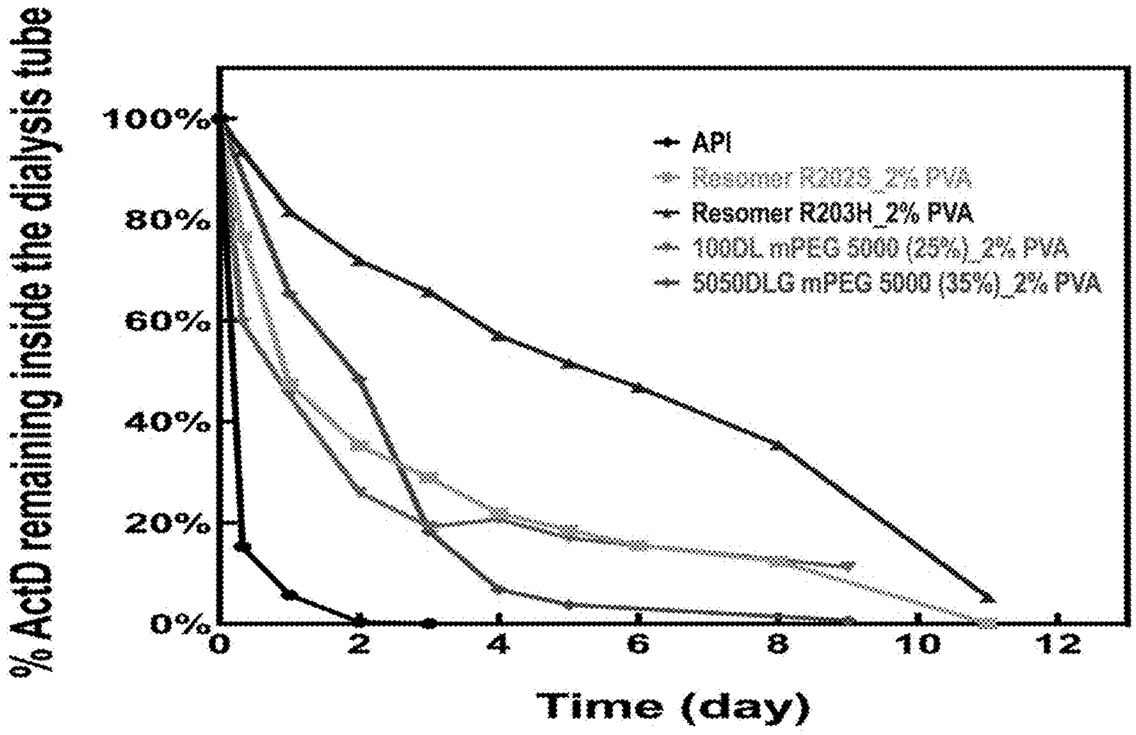
FIG. 27 is a series of graphs showing the in vitro release of free dactinomycin compared to four compositions prepared with dactinomycin and Resomer® R 202 S, Resomer® R 203 H, Resomer® 100DL mPEG 5000 (25%), and Resomer® 5050DLG mPEG 5000 (35%).
Figure 28A:
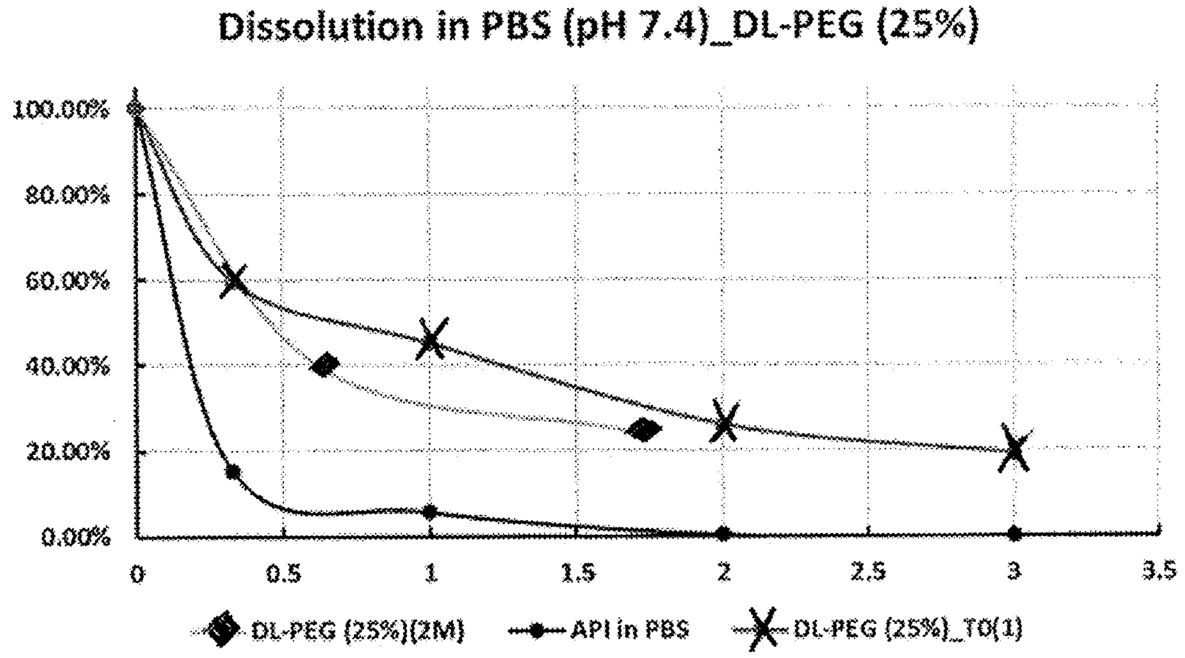
FIGS. 28A-D are a series of graphs showing the in vitro release of dactinomycin from four compositions of the application after storage of the compositions at 4 C for 2 months.
Figure 28B:
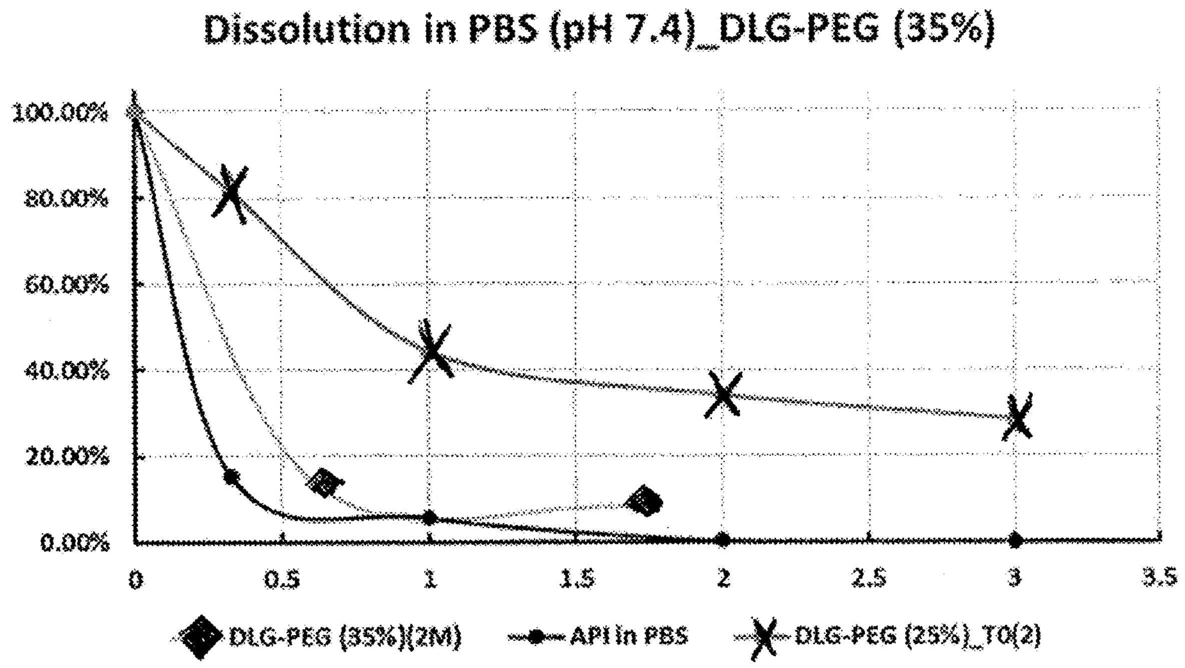
Figure 28C:
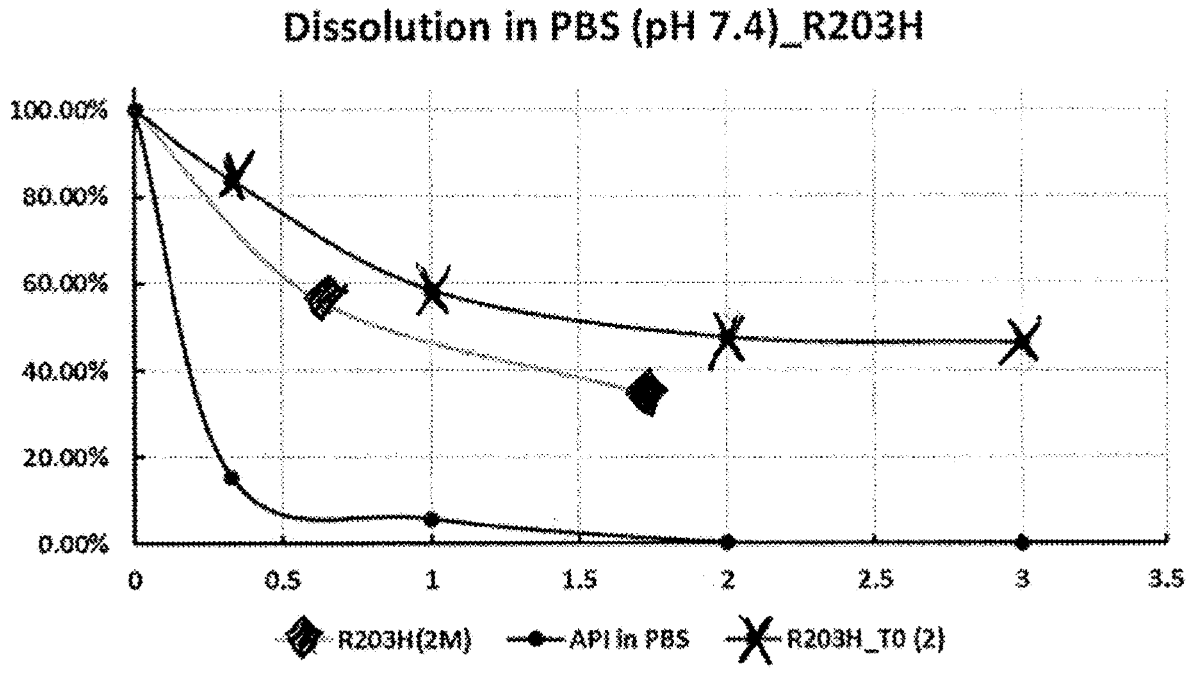
Figure 28D:
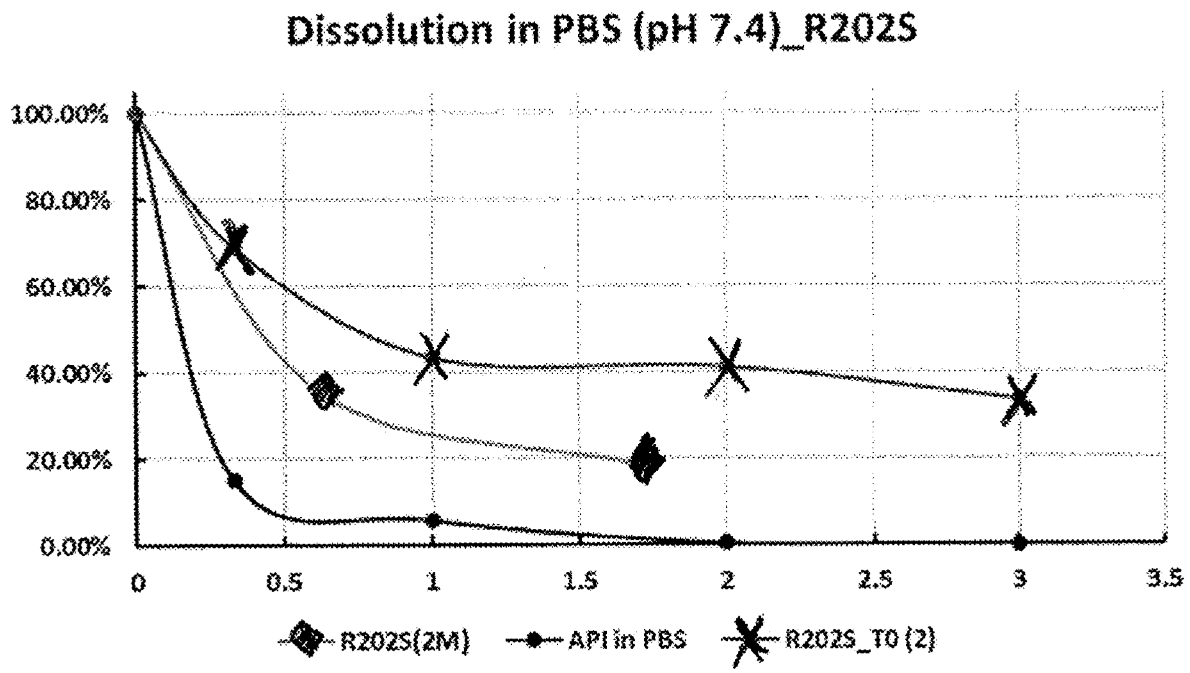

Under in vivo conditions API from non-mPEGylated polymers were cleared faster than mPEGylated polymers. (FIG. 27.)

In another experiment, the in vitro of release of dactinomycin encapsulated nanoparticles in mPEGylated and non-mPEGylated nanoparticles was evaluated after 2 months of storage at 4° C. (FIG. 28.)

Slow and sustained release of dactinomycin was observed from PEGylated poly D,L-lactide nanoparticle following 2 months of storage at 4° C. (A). Dactinomycin release from PEGylated DLG nanoparticles (B) was comparable to that observed for unformulated API, which suggests that these nanoparticles are not stable at 2 months at 4° C.

Example 6: Tolerability of Free Actinomycin D and Encapsulated Actinomycin D with mPEG-Ylated and Non-mPEG-Ylated Nanoparticles in Rats Free and formulated actinomycin D (0.5 mg/kg) was administered via IV A significant decrease in body weight observed in rats administered free API with gradual recovery over 7 days post treatment.

Comparatively less weight loss recorded for animals administered encapsulated dactinomycin with PEGylated poly D,L-lactide (DL-PEG 25%) and non-PEGylated poly D,L-lactide (R203H).

Significant increase in weight observed on day 4 in rats administered DL-PEG (25%) as compared to free actinomycin returning to normal levels by day 7.

Rats administered R203H also exhibited body weight gain by day 7.

Pharmacokinetic evaluation of processed dactinomycin concentration in systemic circulation: $C_{MAX}$ for total plasma samples extracted in mixture of methanol and formic acid to determine total (free and encapsulated dactinomycin corresponding to PEGylated polymers was significantly higher than that observed for unformulated or non-PEGylated polymers. Substantial levels of dactinomycin encapsulated in PEGylated polymers was still in circulation at 6 hr. sampling in contrast to non-PEGylated polymers or unformulated API.

In another experiment, rats were also administered a single dose (0.5 mg/kg) of free and formulated Act D via IV (intravenous) injection.

Figure 29:
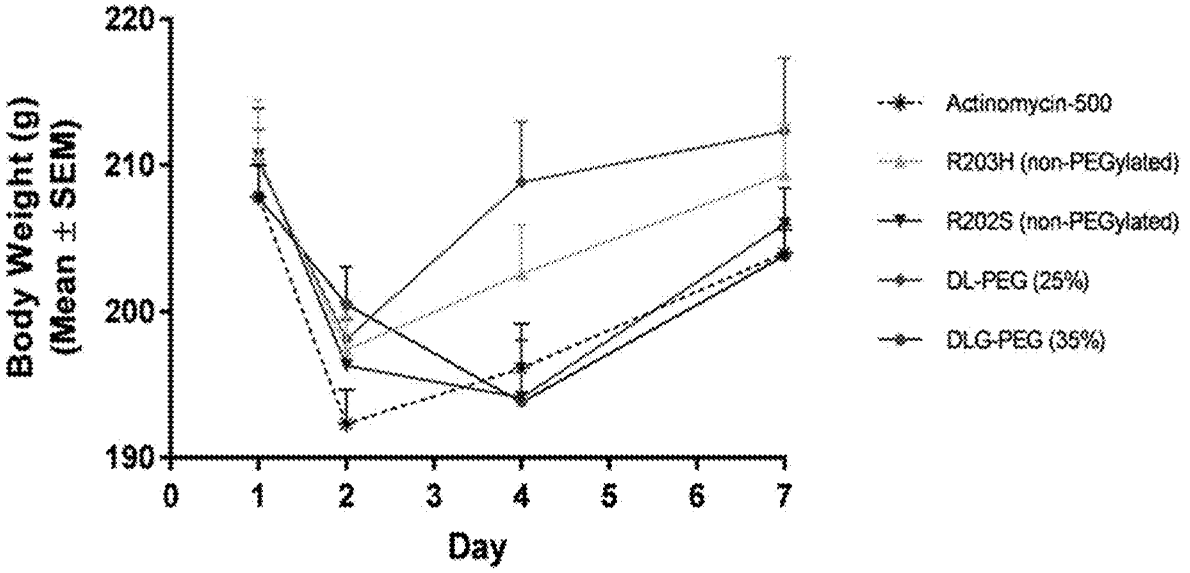
FIG. 29 is a series of graphs showing the effect on rat body weight over time after in vivo treatment of free dactinomycin compared to four compositions of the application (Resomer® R 202 S, Resomer® R 203 H, Resomer® 100DL mPEG 5000 (25%), and Resomer® 5050DLG mPEG 5000 (35%)).

A significant decrease in body weight observed in rat following administration of free dactinomycin with gradual recovery over 7 days post treatment. (FIG. 29)

Comparatively less weight loss recorded for PEGylated poly D,L-lactide nanoparticle (DL-PEG 25%) and non-PEGylated poly D,L-lactide nanoparticle (R203H) administered rats. (FIG. 29)

Significant increase in weight observed on day 4 in rats administered DL-PEG (25%) as compared to free dactinomycin returning to normal levels by day 7. (FIG. 29)

Figure 30:
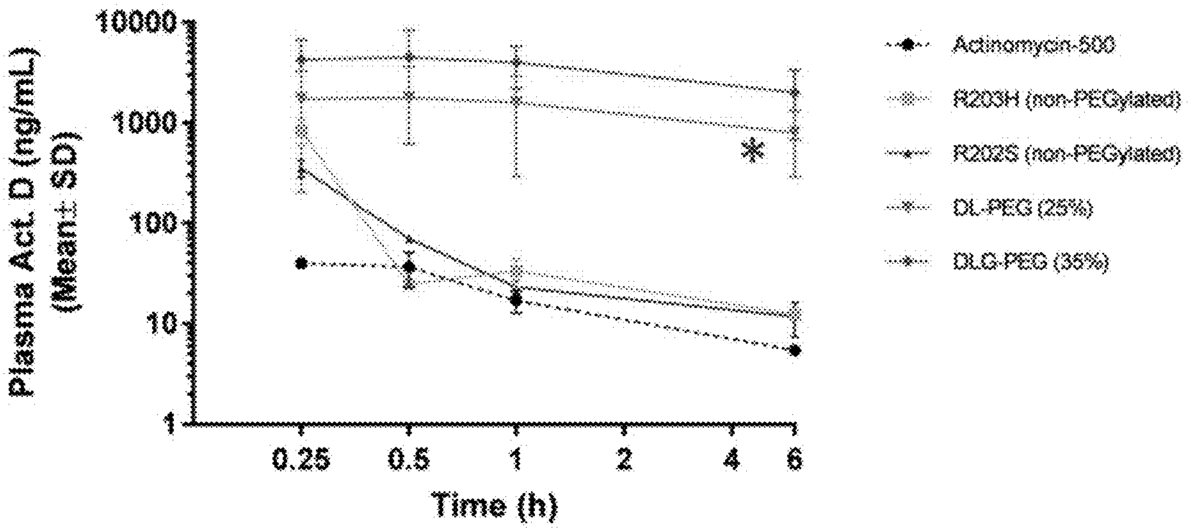
FIG. 30 is a series of graphs showing the effect on $C_{MAX}$ over time after in vivo treatment of free dactinomycin compared to four compositions of the application (Resomer® R 202 S, Resomer® R 203 H, Resomer® 100DL mPEG 5000 (25%), and Resomer® 5050DLG mPEG 5000 (35%)).

$C_{MAX}$ for Act D encapsulated in PEGylated polymers significantly higher than unformulated and free API. (FIG. 30)

Although the observed $C_{MAX}$ for unformulated API is lower, it is associated with adverse effect on body weight.

Six hours after administration, substantial Act D encapsulated in PEGylated polymers retained in plasma as compared to that in non-PEGylated polymers. (FIG. 30)

DL-PEG 25% nanoparticles exhibit high systemic API levels with minimal adverse effects.

Figure 31:
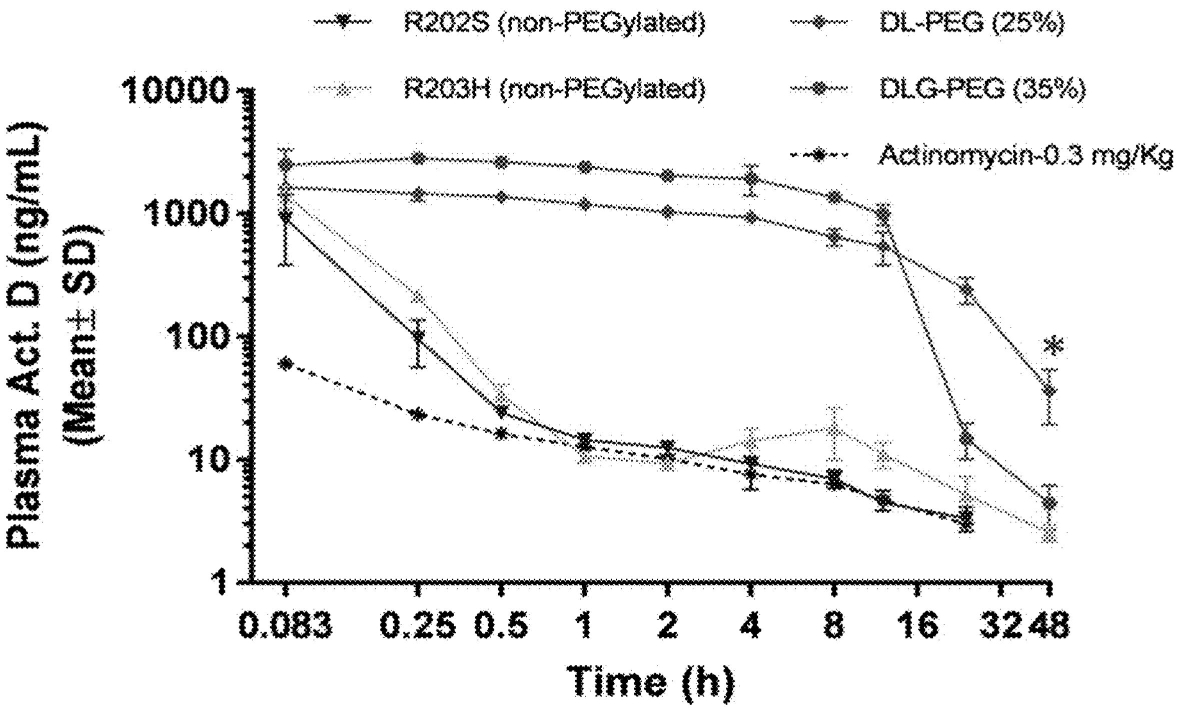
FIG. 31 is a series of graphs showing the effect on $C_{MAX}$ over time after in vivo treatment of free dactinomycin compared to four compositions of the application (Resomer® R 202 S, Resomer® R 203 H, Resomer® 100DL mPEG 5000 (25%), and Resomer® 5050DLG mPEG 5000 (35%)).

Example 7: Pharmacokinetics of Free Actinomycin D and Encapsulated Actinomycin D with mPEG-Ylated and Non-mPEG-Ylated Nanoparticles in Rats Rats administered single dose (0.3 mg/kg) of unformulated and formulated Actinomycin D via IV injection. (FIG. 31)

Processed plasma samples at indicated times extracted in mixture of methanol and formic acid to determine total (free and encapsulated) API in systemic circulation.

PEGylated polymer formulated API (DL-PEG 25% and DLG-PEG 35%) are in systemic circulation up to 48 h as compared to that observed with non-PEGylated polymers (R202S and R203H).

PK profile similar to that observed in rat tolerability study (previous example).

Of the four formulated prototypes, DL-PEG (25%) exhibits the best PK profile with minimal adverse effects.

From these experiments, human equivalent doses (HED) AND Cmax Values for Free Actinomycin D and Nanoparticle Formulations were determined to be as follows:

| Test Article | HED* (mg/kg) | $C_{max}$ in Rats (ng/mL) | Theoretical $C_{max}$ in Humans (ng/ml) |
|---|---|---|---|
| Actinomycin D (free) | 0.05 | 60 | 7.5 |
| DL PLA (R202S) | | 907 | 114 |
| PLGA 50:50 (R203H) | | 1400 | 176 |
| DL PLA (25% MPEG) | | 1650 | 208 |
| PLGA 50:50 (35% MPEG) | | 2500 | 315 |

Example 8: Single Dose Intravenous Administration of Free Actinomycin D or Nanoparticle-Encapsulated Actinomycin D in Rats A side by side comparison of the tolerability of free actinomycin D (i.e., not in a nanoparticle) and four compositions comprising actinomycin D nanoparticles (NP-ActD) formulations in rats when dosed by intravenous administration.

Female Sprague Dawley rats (HSd:SD), 6-8 weeks and 150-175 g at dosing were used for these studies. This is a single dose study with observations for 14 days post-dose. On day 1 of the study, each animal received either 900 µg/kg of the free actinomycin D or a NP-ActD formulations (900 µg/kg of the active) in a fixed volume of 1 mL/kg according to the study design in the Table below.

| Group | Treatment via IV Administration | Dose Level (µg/kg) As Active Act D | Number of Rats (Females) |
|---|---|---|---|
| 1 | Nanoparticle Formulation of Act D-R203H | 900 | 6 |
| 2 | Nanoparticle Formulation of Act D-R202S | 900 | 6 |
| 3 | Nanoparticle Formulation of Act D-DL-PEG(25%) | 900 | 6 |
| 4 | Nanoparticle Formulation of Act D-DLG-PEG (35%) | 900 | 6 |
| 5 | Free Actinomycin D | 900 | 6 |

The following parameters were monitored: clinical observations daily, mortality, body weights, and food consumption. A full necropsy will be conducted on Day 14 post-dose, at which time organ weights and macroscopic findings will be determined. The organs will be preserved for future histology and the lungs, liver, pancreas, spleen, brain and kidneys will be frozen in liquid nitrogen for measurement of actinomycin D/NP-ActD accumulation.

Blood was collected for pharmacokinetic evaluation following dosing on Day 1 at 0.083, 0.25, 0.5, 1, 2, 6, and 24 hours post dose. Serum samples will be collected for clinical chemistry and whole blood samples for hematology.

Figure 32:
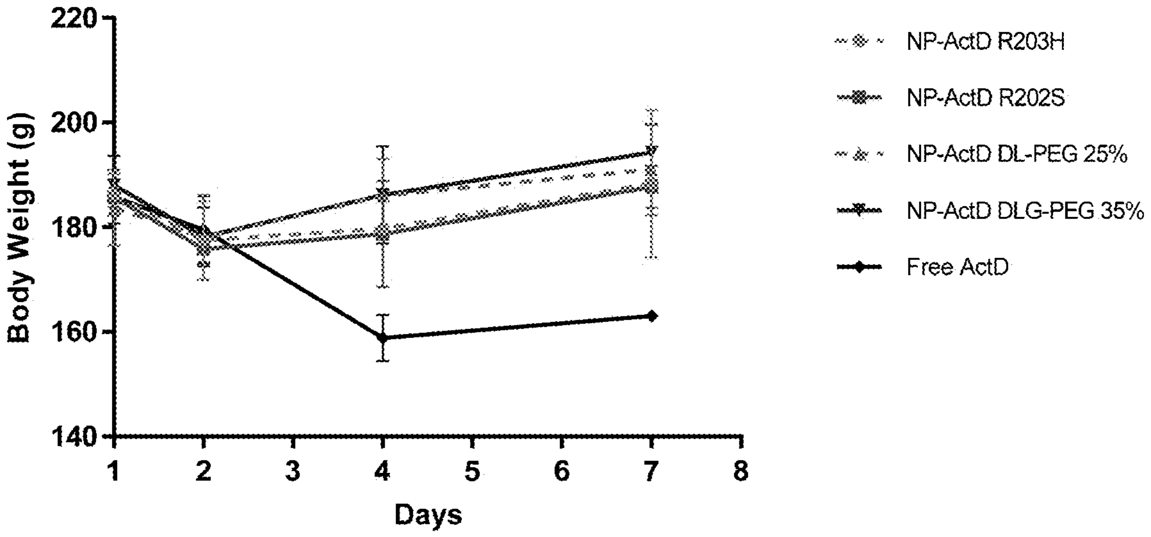
FIG. 32 is a series of graphs showing the effect on rat body weight over time after in vivo treatment of free dactinomycin compared to four compositions of the application (Resomer® R 202 S, Resomer® R 203 H, Resomer® 100DL mPEG 5000 (25%), and Resomer® 5050DLG mPEG 5000 (35%)).

Analysis of Body Weights (FIG. 32). Following intravenous dosing of Act D and NP-ActD ((900 µg/kg), animals dosed with free act D showed consistently decreased body weights and unable to recover even 7 days post-dose. In contrast, animals dosed with the four NP-ActD formulations did not show drug related body weight loss. Thus, a clear separation in the extent of body weight loss was observed between the free ActD animals and NP-ActD dosed animals.

Animals in the free Act D group exhibited toxicity 3 days post-dose such as piloerection, decreased activity, bleeding at the nares, and hunched posture which became worse with time.

In comparison, animals dosed with nanoparticle-Act D formulations, appeared normal without any signs of toxicity. However, at day 7 post-dose 2-3 animals in each of the groups dosed with the NP-ActD R202S and NP-ActD DLG-PEG 35% formulations showed injection site scabbing and slight decreased activity but not serious and was not progressive.

Figure 33:
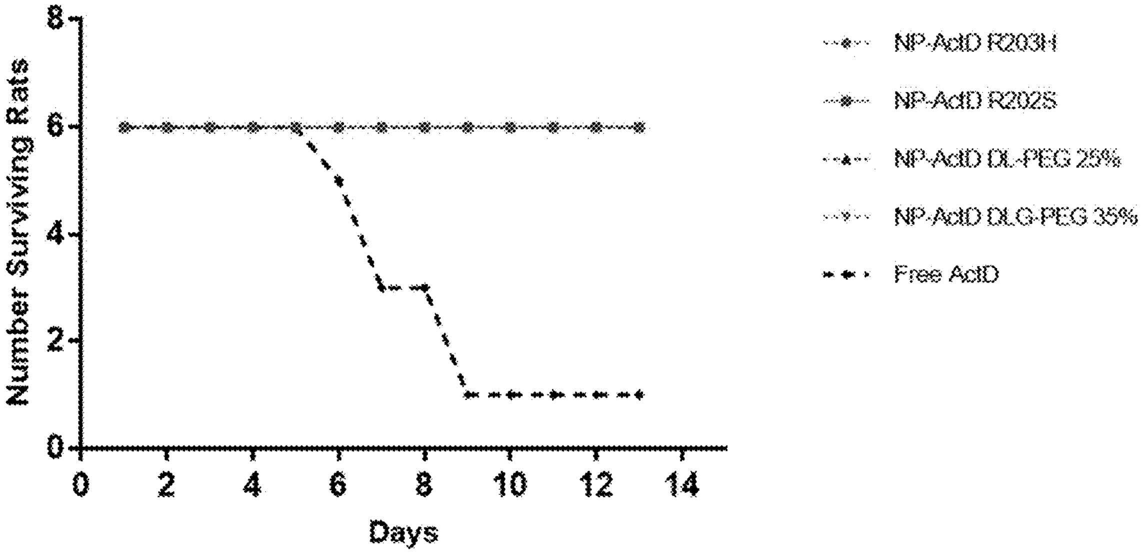
FIG. 33 is a series of graphs showing the survival rate over time after in vivo treatment of free dactinomycin compared to four compositions of the application (Resomer® R 202 S, Resomer® R 203 H, Resomer® 100DL mPEG 5000 (25%), and Resomer® 5050DLG mPEG 5000 (35%)).

Mortality (FIG. 33). At day 6 post-dose, 1 animal in the free ActD group was moribund and euthanized (according to the IACUC regulations to ease pain and suffering). On Day 7 post dose, two additional animals in the free Act D group had to be euthanized due to extremely poor health.

On Day 9, two more animals in the free ActD group were euthanized due to poorer and failing health.

Thus, after thirteen days post-dose in the free ActD group, only 1/6 animals remained, but the animal continued to show signs of toxicity such as piloerection and discolored urine.

After 13 days post-dose in the ActD group, only one animal remained, and still exhibited poor health conditions (ongoing study). Thus, the mortality rate in the ActD group is about 80%. In contrast, all animals in the NP-ActD formulation groups have survived (100% survival) with minimal toxicity such as injection site inflammation and piloerection likely, due to slow release of free ActD from the nanoparticles but had no effect on body weight gains. Since free actinomycin D is toxic in vivo, these results demonstrate the effectiveness of the nanoparticle ActD formulations as a method to reduce host toxicity.

The application can be embodied in other specific forms without departing from the spirit or essential characteristics thereof. The foregoing embodiments are therefore to be considered in all respects illustrative rather than limiting on the application described herein. Scope of the application is thus indicated by the appended claims rather than by the foregoing description, and all changes that come within the meaning and range of equivalency of the claims are intended to be embraced therein.

What is claimed is:

1. A method for treating a myelodysplastic syndrome (MDS) in a subject in need thereof comprising administering to the subject a therapeutically effective amount of a composition comprising a therapeutically effective amount of dactinomycin encapsulated in nanoparticles comprising PLA-mPEG, wherein: the PLA-mPEG comprises about 25% mPEG by weight; the molecular weight of the PLA-mPEG is about 30,000 Da; and the nanoparticles have an average size of about 100 nm to about 200 nm; wherein the therapeutically effective amount of the composition, upon administration to the subject, results in a $C_{max}$ of dactinomycin in the subject of about 1 ng/mL to about 20 ng/mL.

2. The method of claim 1, wherein the composition further comprises a surfactant.

3. The method of claim 2, wherein the surfactant is polyvinyl alcohol.

4. The method of claim 1, wherein the composition comprises about 5% by weight to about 15% by weight dactinomycin.

5. The method of claim 1, wherein the composition further comprises a therapeutically effective amount of at least one chemotherapeutic drug selected from the group consisting of a topoisomerase inhibitor, a platinum-based therapy, an anthracycline antibiotic, a taxane, a tyrosine kinase inhibitor, a nucleoside analog, a FLT3 inhibitor, and a hyper methylation inhibitor, wherein the molar ratio of the topoisomerase inhibitor, platinum-based therapy, anthracycline antibiotic, taxane, tyrosine kinase inhibitor, nucleoside analog, FLT3 inhibitor, or hyper methylation inhibitor to dactinomycin is 7:1, 6:1, 5:1, 4:1, 3:1, 2:1, 1:1, <1:1, or any ratio in between.

* * * * *